(12) United States Patent
Green et al.

(10) Patent No.: US 9,884,118 B2
(45) Date of Patent: Feb. 6, 2018

(54) MULTICOMPONENT DEGRADABLE CATIONIC POLYMERS

(71) Applicant: THE JOHNS HOPKINS UNIVERSITY, Baltimore, MD (US)

(72) Inventors: Jordan J. Green, Columbia, MD (US); Joel C. Sunshine, Baltimore, MD (US); Nupura S. Bhise, Baltimore, MD (US); Ron B. Shmueli, Baltimore, MD (US); Stephany Y. Tzeng, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/644,397

(22) Filed: Mar. 11, 2015

(65) Prior Publication Data
US 2015/0250881 A1    Sep. 10, 2015

Related U.S. Application Data

(62) Division of application No. 13/320,621, filed as application No. PCT/US2010/035127 on May 17, 2010, now Pat. No. 8,992,991.

(60) Provisional application No. 61/178,611, filed on May 15, 2009.

(51) Int. Cl.
| | | |
|---|---|---|
| A61K 47/20 | (2006.01) | |
| C08F 222/10 | (2006.01) | |
| A61K 38/02 | (2006.01) | |
| C07C 323/25 | (2006.01) | |
| A61K 31/713 | (2006.01) | |
| A61K 9/107 | (2006.01) | |
| C07C 229/12 | (2006.01) | |
| C08G 73/02 | (2006.01) | |
| C12N 15/88 | (2006.01) | |
| A61K 48/00 | (2006.01) | |

(52) U.S. Cl.
CPC ............ *A61K 47/20* (2013.01); *A61K 9/1075* (2013.01); *A61K 31/713* (2013.01); *A61K 38/02* (2013.01); *C07C 229/12* (2013.01); *C07C 323/25* (2013.01); *C08F 222/1006* (2013.01); *C08G 73/028* (2013.01); *C12N 15/88* (2013.01); *A61K 48/00* (2013.01); *C08F 2222/1013* (2013.01)

(58) Field of Classification Search
None
See application file for complete search history.

(56) References Cited

U.S. PATENT DOCUMENTS

| 6,998,115 | B2 | 2/2006 | Langer et al. |
| 7,427,394 | B2 | 9/2008 | Anderson et al. |
| 2005/0265961 | A1 | 12/2005 | Langer et al. |
| 2010/0036084 | A1 | 2/2010 | Langer et al. |

OTHER PUBLICATIONS

Kim et al., "Arginine-grafted bioreducible poly(disulfide amine) for gene delivery systems", Biomaterials,30, 2009, pp. 658-664.*
Sunshine, J. et al., Small-Molecule End-Groups of Linear Polymer Determine Cell-type Gene-Delivery Efficacy, Advanced Materials (Weinheim, Germany) (Dec. 2009), 21(48), pp. 4947-4951, ISSN: 0935-9648, See Figures 1-3 and Experimental.
Lee, J.-S. et al., Gold, Poly(beta-amino ester) Nanoparticles for Small Interfering RNA Deliery, Nano Letters (May 7, 2009), 9(6), pp. 2402-2406, ISSN: 1530-6984, See the abstract and Figures 1-5.
Green, J.J. et al., Combinatorial modification of degradable polymers enables transfection of human cells comparable to adenovirus, Advanced Materials (Weinheim, Germany) (2007), 19(19), pp. 2836-2842, ISSN: 0935-9648, See Figures 1-4 and Experimental.
Zugates, G.T. et al., Gene Delivery Properties of End-Modified Poly(beta-amino ester), Bioconjugate Chemistry (2007), 18(6), pp. 1887-1896, ISSN: 1043-1802, See the abstract, Introduction, Experimental Section and Figures 1-4.
Anderson, D.G., et al., Semi-Automated Synthesis and Screening of a Large Library of Degradable Cationic Polymers for Gene Delivery, Angew. Chem. Intl. Ed. 2003 Wiley-VCH Verlag GmbH & Co. KGaA, Weinheim, Germany, 42, pp. 3153-3158.
Anderson, D.G., et al., Structure/Property Studies of Polymeric Gene Delivery Using a Library of Poly (beta-amino esters), Molecular Therapy vol. 11, No. 3, Dec. 2004, pp. 426-434.
Shmueli, R.B. et al., Electrostatic surface modifications to improve gene delivery, Expert Opinion Drug Delivery Review Article 2010, 7(4): 535-550, 2010 Informa UK Ltd ISSN 1742-5247.
Green, J.J. et al., A Combinatorial Polymer Library Approach Yields Insight Into Nonviral Gene Delivery, Accounts of Chemical Research, vol. 41, No. 6, Jun. 2008, pp. 749-759, 2008 American Chemical Society.
Sunshine, J. et al., Degradable Polymers for Gene Delivery, 31st Annual International Conference of the IEEE EMBS, Minneapolis, Minnesota, Sep. 2-6, 2009, pp. 2412-2415, 2009 IEEE.
Lin et al., "Disulfide-containing poly(beta-amino ester)s for gene delivery", Journal of controlled release : official journal of the Controlled Release Society Volume, 116(2), 2006, pp. e79-e81.
International Search Report, dated Jan. 28, 2011 for PCT/US2010/035127.

* cited by examiner

*Primary Examiner* — Melissa Fisher
(74) *Attorney, Agent, or Firm* — Morgan, Lewis & Bockius LLP

(57) ABSTRACT

Degradable polymers were synthesized that self-assemble with DNA to form particles that are effective for gene delivery. Small changes to polymer synthesis conditions, particle formulation conditions, and polymer structure provides significant changes to efficacy in a cell-type dependent manner. Polymers presented here are more effective than commercially available materials, such as LIPO-FECTAMINE 2000™, FUGENE®, or polyethylenimine (PEI), for gene delivery to cancerous fibroblasts or human primary fibroblasts. The presently disclosed materials may be useful for cancer therapeutics and regenerative medicine.

17 Claims, 25 Drawing Sheets

RNA:
——— =20 w/w
- - - - =40 w/w
·········· =80 w/w

MULTICOMPONENT DEGRADABLE CATIONIC POLYMERS

CROSS-REFERENCE TO RELATED APPLICATIONS

This application is a divisional application of U.S. patent application Ser. No. 13/320,621, which is a 35 U.S.C. §371 U.S. national entry of International Application PCT/US2010/035127 having an international filing date of May 17, 2010, which claims the benefit of U.S. Provisional Application No. 61/178,611, filed May 15, 2009, the contents of each of the aforementioned applications is incorporated herein by reference in its entirety.

BACKGROUND

Gene delivery has great potential, both as a therapeutic to treat disease on the genetic level and as a technology to facilitate regenerative medicine. One challenge to gene delivery is finding a safe and effective delivery system. Because viral gene therapy can have serious safety concerns, many recent efforts have focused on non-viral gene delivery methods that use biomaterials. Many biomaterials, including cationic lipids, sugars, peptides, and polymers, have been shown to be effective for delivering genes in vitro. See T. G. Park, et al., *Adv. Drug Del. Rev.* 58:467-486 (2006); D. W. Pack, et al., *Nat. Rev. Drug Discovery* 4:581-593 (2005); and M. C. Pedroso de Lima, et al., *Adv. Drug Del. Rev.* 47:277-94 (2001).

One of the lead polymers for gene delivery is polyethylenimine (PEI), which, due its cationic structure, can be very effective for binding DNA and forming gene delivery particles. See O. Boussif, et al., *Proc. Natl. Acad. Sci. USA* 92:7297-301 (1995). PEI also is particularly effective at promoting endosomal escape of PEI/DNA particles through the proton sponge mechanism. See N. D. Sonawane, et al., *J. Biol. Chem.* 278:44826-44831 (2003); A. Akinc, et al., *J. Gene Med.* 7:657-663 (2005). This mechanism is critical in preventing lysosomal degradation of the DNA and to enable efficient delivery of the DNA to the cytoplasm. This endosomal escape mechanism has been used in the design of other synthetic gene delivery polymers, including polylysine-based polymers that contain an imidazole group in the side chain. See D. Putnam, et al., *Proc. Natl. Acad. Sci. USA* 98:1200-5 (2001). Although PEI shows promise compared to other biomaterials, it also leads to significant cytotoxicity, see S. M. Moghimi, et al., *Mol. Ther.* 11:990-5 (2005), and has lower effectiveness than viral methods.

One newer group of polymers used for gene delivery are poly(beta-amino ester)s, see J. J. Green, et al., *Acc. Chem. Res.* 41:749-759 (2007), which are useful due to their ability to bind DNA, promote cellular uptake, facilitate escape from the endosome, and allow for DNA release in the cytoplasm. See D. M. Lynn and R. Langer, *J. Am. Chem. Soc.* 122:10761-10768 (2000); D. G. Anderson, et al., *Mol. Ther.* 11:426-34 (2005); and A. Akinc, et al., *J. Am. Chem. Soc.* 125:5316-23 (2003). Unlike PEI, poly(beta-amino ester)s are readily biodegradable due to their ester linkages, which reduces cytotoxicity. D. M. Lynn and R. Langer, supra, J. J. Green, et al., *Bioconjugate Chem.* 17:1162-1169 (2006). It has been shown that within this class, acrylate-terminated polymers have low gene delivery, whereas amine monomer-terminated polymers have higher delivery. See A. Akinc, et al., *Bioconjugate Chem.* 14:979-988 (2003). Recently, end-modification with diamine monomers has shown that some of these polymers can rival adenovirus for gene delivery in vitro and also are effective in vivo. See J. J. Green, et al., *Adv. Mater.* 19:2836-2842 (2007); G. T. Zugates, et al., *Mol. Ther.* 15:1306-1312 (2007).

Another approach to increase gene delivery effectiveness while reducing cytotoxicity involves adding bioreducible linkages to polymers. Disulfide linkages have been added to PEI to produce bioreducible versions with lower cytotoxicity than high molecular weight versions of the parent polymer. M. A Gosselin, et al., *Bioconjugate Chem.* 12:989-994 (2001); M. L. Forrest, et al., *Bioconjug Chem.* 14:934-40 (2003). Other researchers have shown that bioreducible poly(amido amines) can have higher efficacy than PEI while also having reduced cytotoxicity. See L. V. Christensen, et al., *Bioconjugate Chem.* 17:1233-40 (2006); C. Lin, et al., *J. Controlled Release* 126:166-74 (2008).

Further, it was recently demonstrated that IMR-90 human primary fibroblasts can be reprogrammed to induced pluripotent stem cells with integrating viruses. See J. Yu, et al., *Science* 318:1917-20 (2007). Reprogramming human differentiated cells into undifferentiated, pluripotent cells could potentially allow a patient to receive a customized cell therapy that is a perfect genetic match.

SUMMARY

In some aspects, the presently disclosed subject matter includes a compound of formula (I):

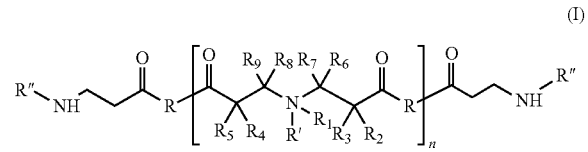

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and at least one of R, R', and R" comprise a reducible or degradable linkage, and wherein each R, R', or R" can independently be the same or different;

under the proviso that when at least one R group comprises an ester linkage of the formula —C(=O)—O— and the compound of formula I comprises a poly(beta-amino ester), then the compound of formula (I) must also comprise one or more of the following characteristics:

(a) each R group is different;
(b) each R" group is different;
(c) each R" group is not the same as any of R', $R_1$, $R_2$, $R_3$, $R_4$, $R_5$, $R_6$, $R_7$, $R_8$, and $R_9$;
(d) the R" groups degrade through a different mechanism than the ester-containing R groups, wherein the degradation of the R" group is selected from the group consisting of a bioreducible mechanism or an enzymatically degradable mechanism; and/or
(e) the compound of formula (I) comprises a substructure of a larger cross-linked polymer, wherein the larger cross-linked polymer comprises different properties from compound of formula (I);

and pharmaceutically acceptable salts thereof.

In some aspects, the presently disclosed compounds of formula (I) are useful for delivering a therapeutic agent to a cell, a specific cell line, a tissue, or an organism. The therapeutic agent can include a gene, DNA, RNA, siRNA, miRNA, isRNA, agRNA, smRNA, a nucleic acid, a peptide, a protein, a chemotherapeutic agent, a hydrophobic drug, and a small molecule drug.

In other aspects, the presently disclosed subject matter provides a method of treating a disease or condition, the method comprising administering to a subject in need of treatment thereof, a compound of formula (I) further comprising a therapeutic agent effective for treating the disease or condition. Diseases that can be treated by the presently disclosed methods include, but are not limited to, a cancer, including brain cancer (including Glioblastoma Multiforme), lung cancer, breast cancer, prostate cancer, colorectal cancer, and other cancers; cardiovascular diseases; infectious diseases; ophthalmic diseases, including age-related macular degeneration.

In further aspects, the presently disclosed subject matter includes an in vitro kit comprising a compound of formula (I). In yet further aspects, the presently disclosed subject matter includes a biomedical device, such as a stent or a stent-like device, comprising a compound of formula (I) or an article coated with one or more compounds of formula (I) alone or in combination with one or more commercially available and/or FDA-approved polyelectrolyte.

In yet further aspects, the presently disclosed subject matter provides a method of forming a tissue scaffolding structure, the method comprising implanting into a subject a polymeric matrix comprising a compound of formula (I). The implant can include one or more cells selected from the group consisting of hepatocytes, pancreatic islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, epithelial cells, kidney tubular cells, kidney basement cells, kidney tubular cells, kidney basement membrane cells, nerve cells, blood vessel cells, cells forming bone and cartilage, smooth and skeletal muscle cells, cells from the retina and other parts of the eye, stem cells, induced pluripotent stem cells, and three-dimensional organoids.

In additional aspects, the presently disclosed subject matter provides a nanoparticle or microparticle comprising a compound of formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1A:
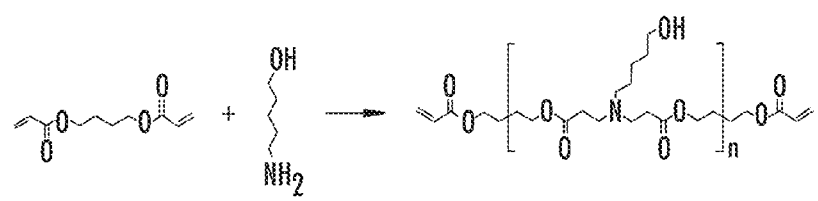
Figure 1B:
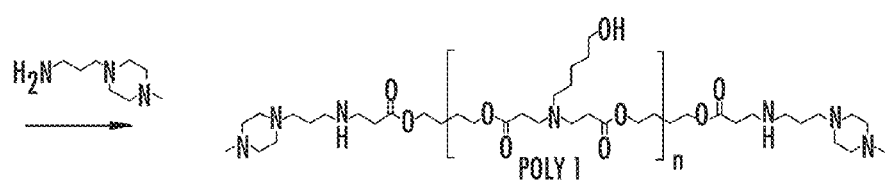
Figure 1C:
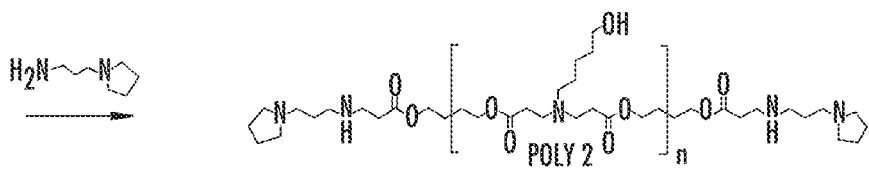
Figure 1D:
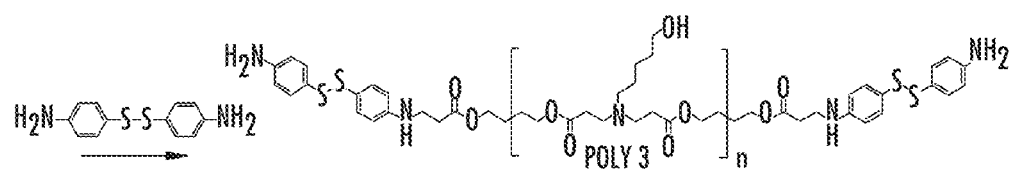
Figure 2:
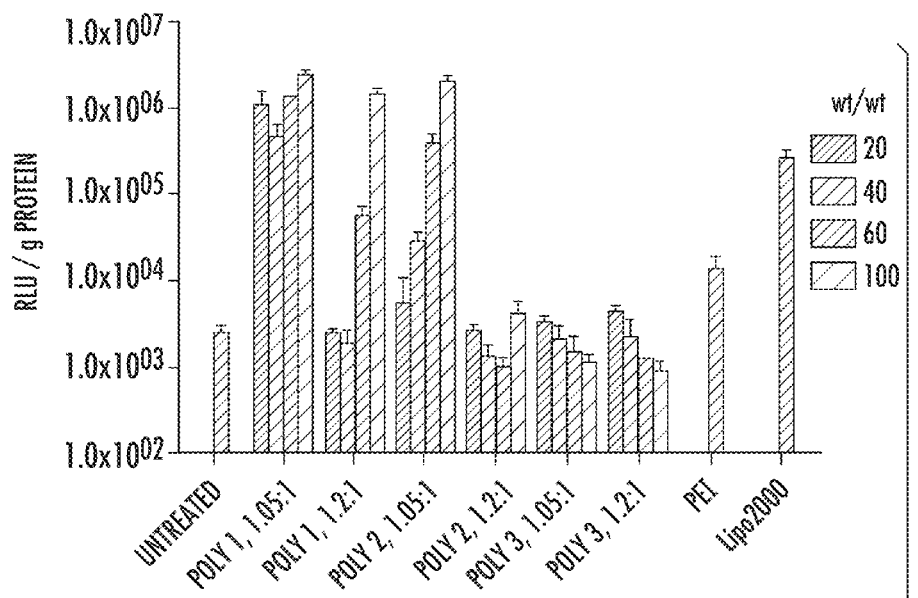
Figure 2:
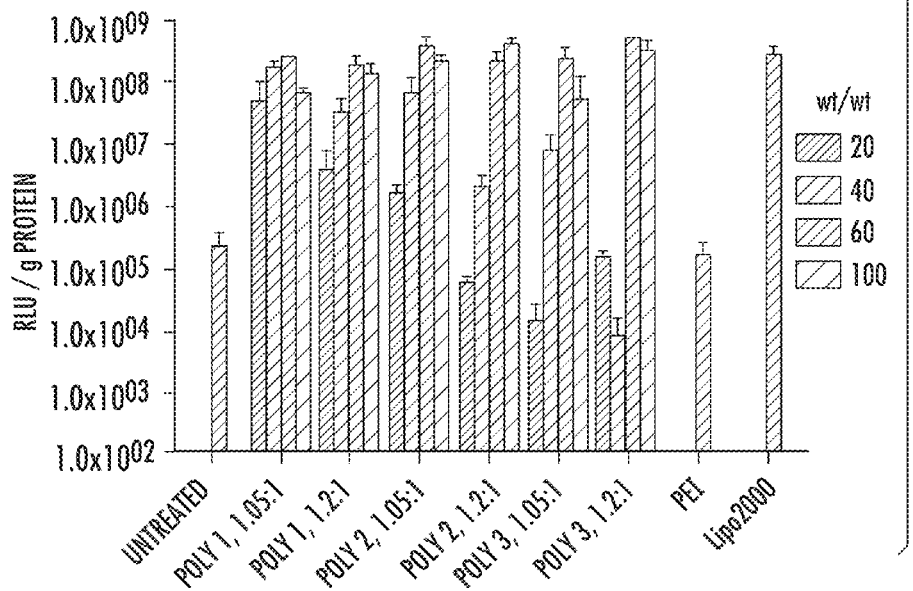
Figure 3:
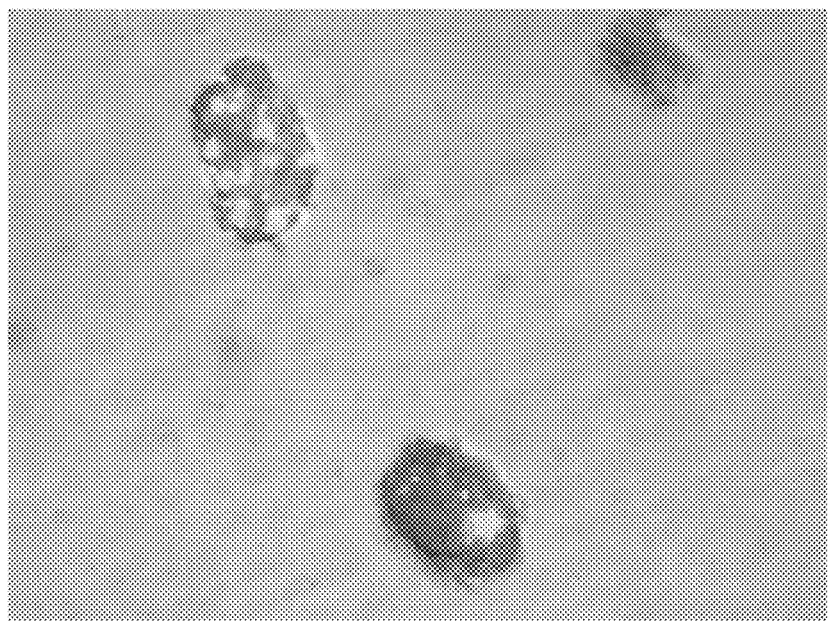
Figure 4:
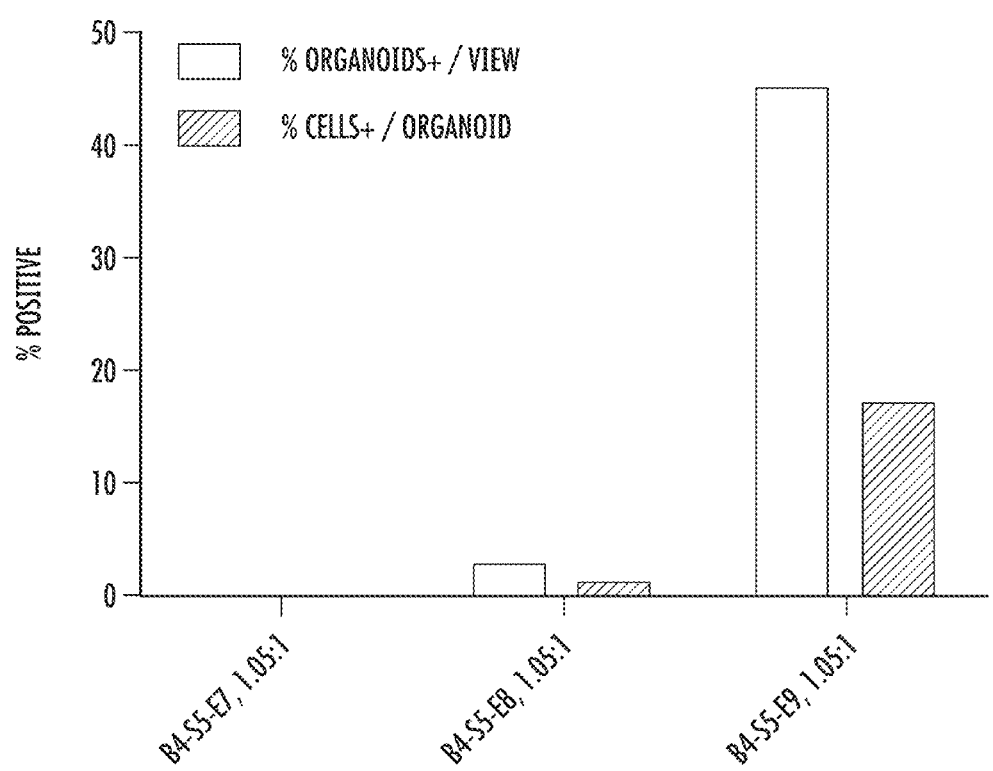
Figure 5:
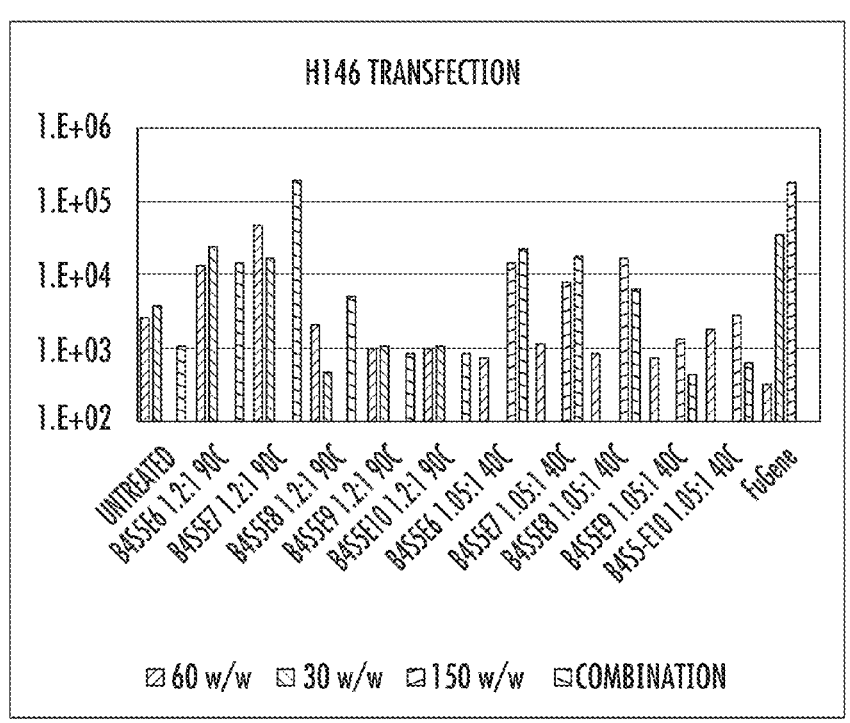
Figure 5:
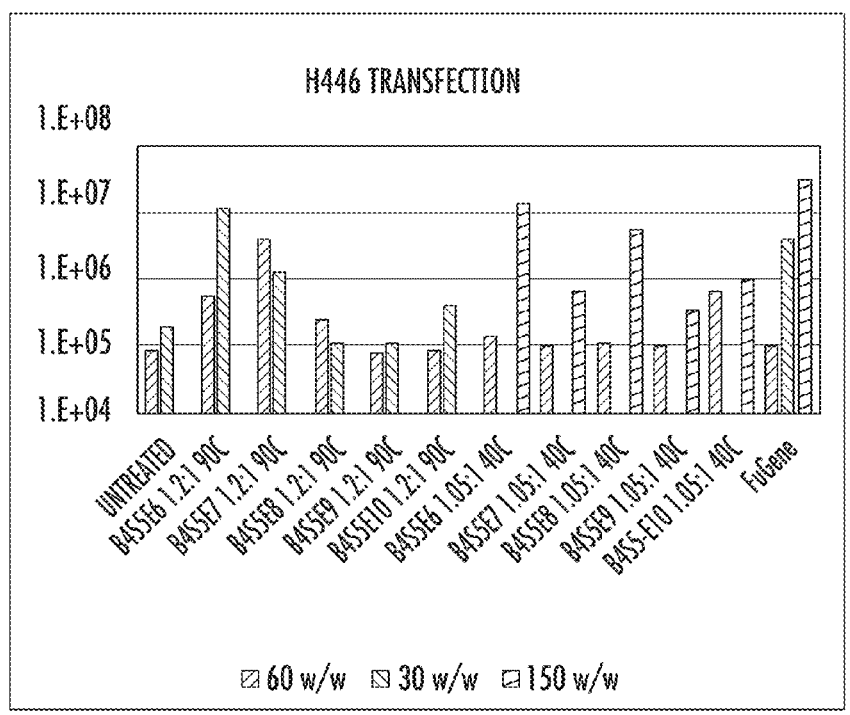
Figure 6:
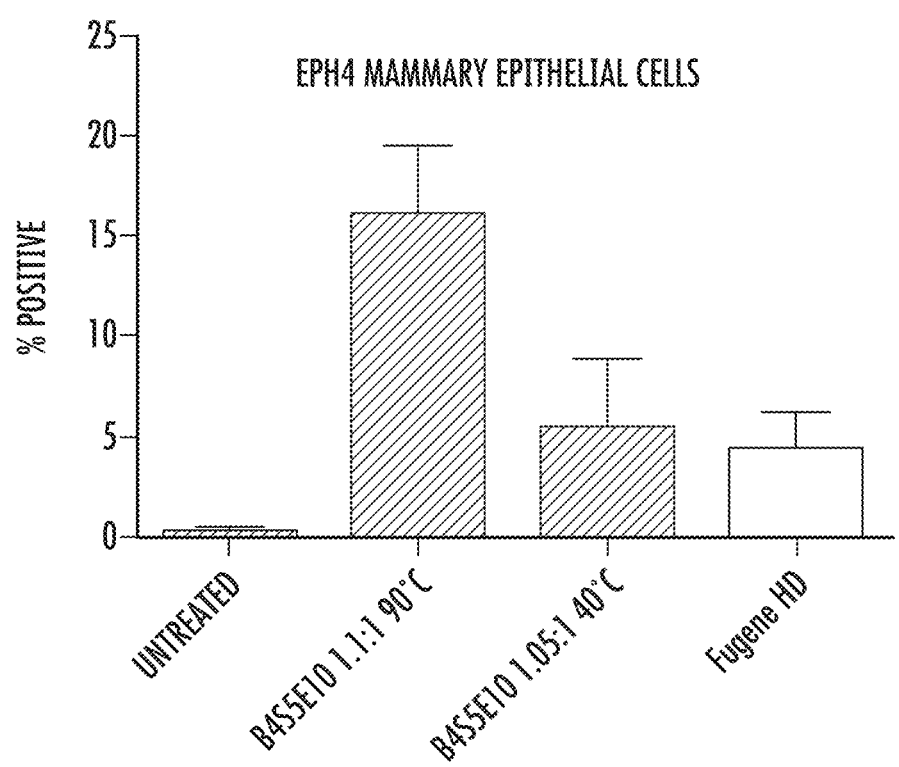
Figure 7:
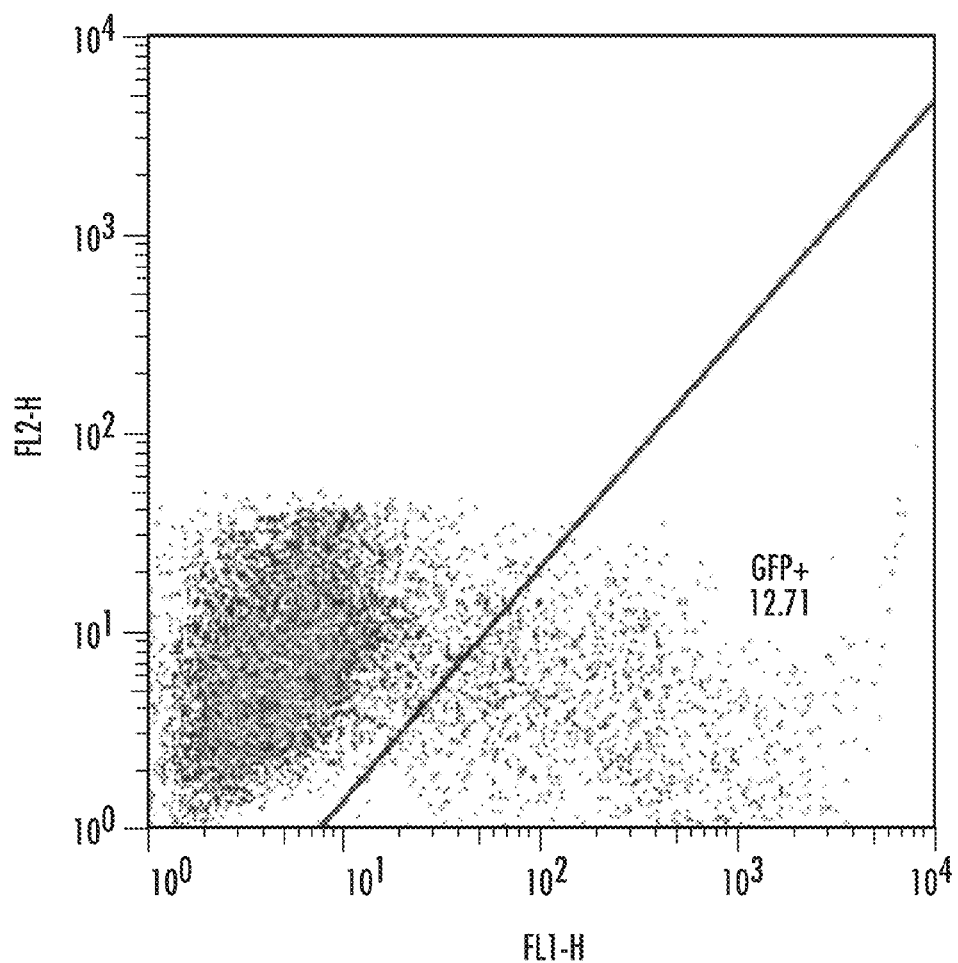

Having thus described the presently disclosed subject matter in general terms, reference will now be made to the accompanying Drawings, which are not necessarily drawn to scale, and wherein:

FIGS. 1a-1d are representative synthesis schemes of representative embodiments of the presently disclosed degradable gene delivery polymers: (a) 1,4-butanediol diacrylate reacts with 1-amino-5-pentanol to form an acrylate-terminated poly(beta-amino ester) precursor. This precursor reacts with: (b) 1-(3-aminopropyl)-4-methylpiperazine to form Poly 1; (c) 1-(3-aminopropyl)pyrrolidine to form Poly 2; or (d) 4-aminophenyl disulfide to form Poly 3;

FIG. 2 shows the gene delivery efficacy of Poly 1, Poly 2, Poly 3, compared to commercial reagents PEI and LIPOFECTAMINE 2000™ to COS-7 cells (above) and IMR-90 cells (below). Luciferase-encoding DNA is delivered and expression is measured as relative light units per gram protein. Polymer to DNA weight ratio (w/w) tunes gene delivery efficacy. Delivery is high even in the presence of serum proteins. The ratios 1.05:1 and 1.2:1 refer to polymerization conditions as described herein and wt/wt is the weight ratio of polymer to DNA. Graphs show mean+SD, n~4;

FIG. 3 demonstrates that genes encoding green fluorescent protein are delivered to primary cells in three-dimensional mammary epithelial organoids by the presently disclosed polymer designated B4-S5-E9 (also referred to herein as Poly 3);

FIG. 4 shows that the disulfide end-group, designated herein as E9, makes biphasic polymer designated B4-S5-E9 more effective than polymers designated B4-S5-E7 or B4-S5-E8, which have difference end groups designated E7 and E8 herein, at transfecting primary cells in three-dimensional organoids (shown in FIG. 3);

FIG. 5 shows gene delivery with a series of presently disclosed polymers comparable to FUGENE HD® in (top) H146 and (bottom) H446 lung cancer cells;

FIG. 6 shows gene delivery of presently disclosed polymers designated as B4-S5-E10 to EPH4 mammary epithelial cells as compared to commercially available reagent FUGENE HD® (% GFP positive as determined by FACS);

FIG. 7 demonstrates the ability of a presently disclosed polymer designated B4-S5-E10 (60 w/w) for transfecting Glioblastoma Multiforme (GBM) cells as measured by flow cytometry and Green Fluorescent Protein (GFP) expression.

Figure 8:
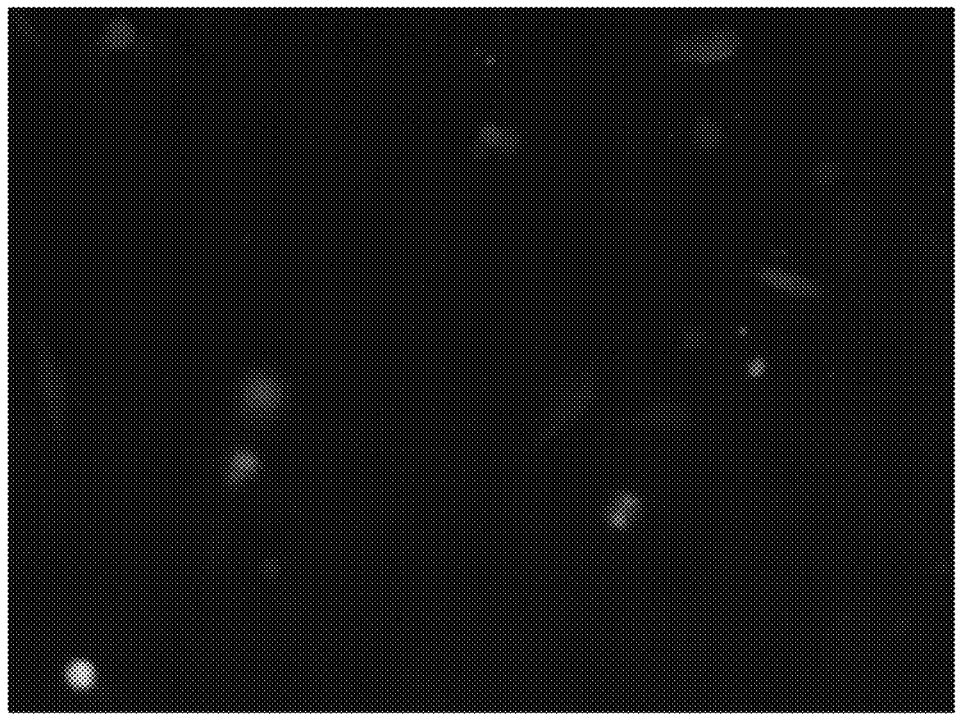
Figure 9:
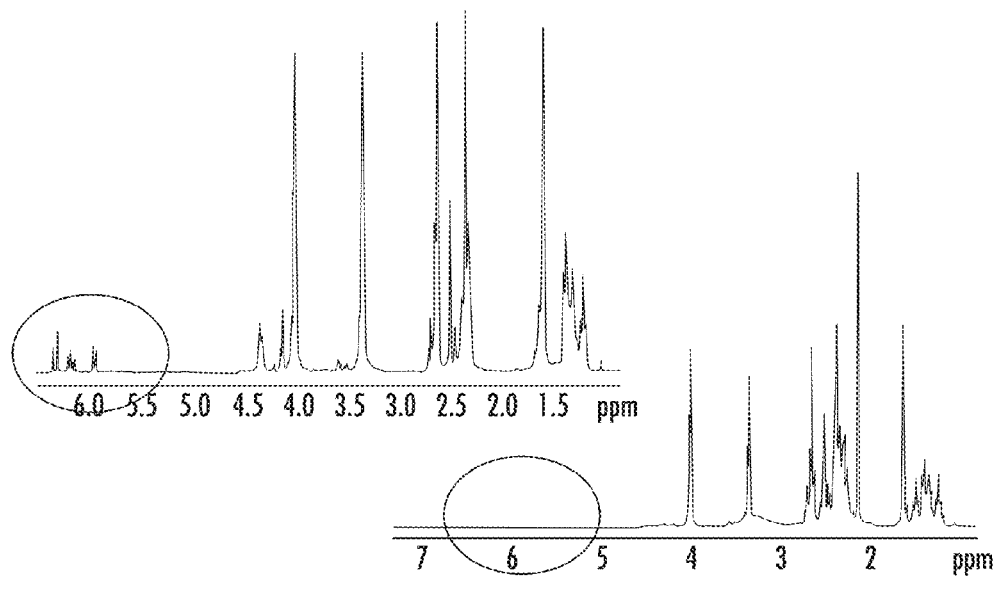
Figure 9:
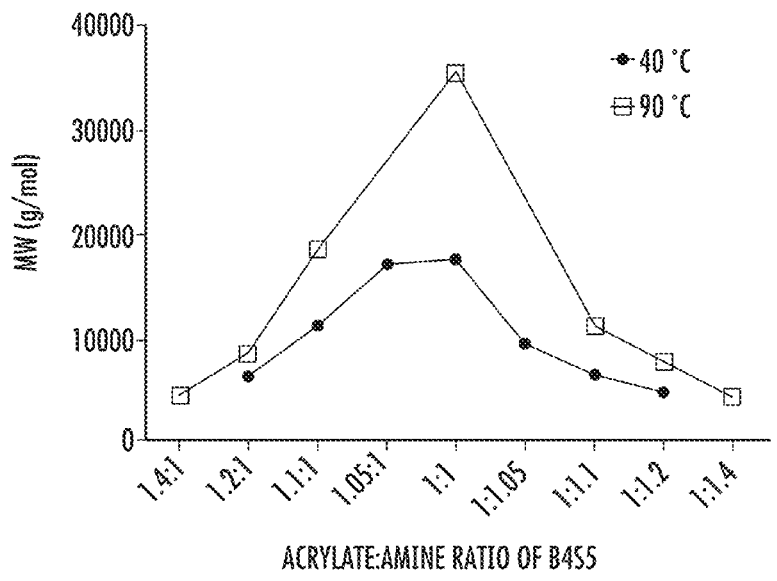
Figure 10:
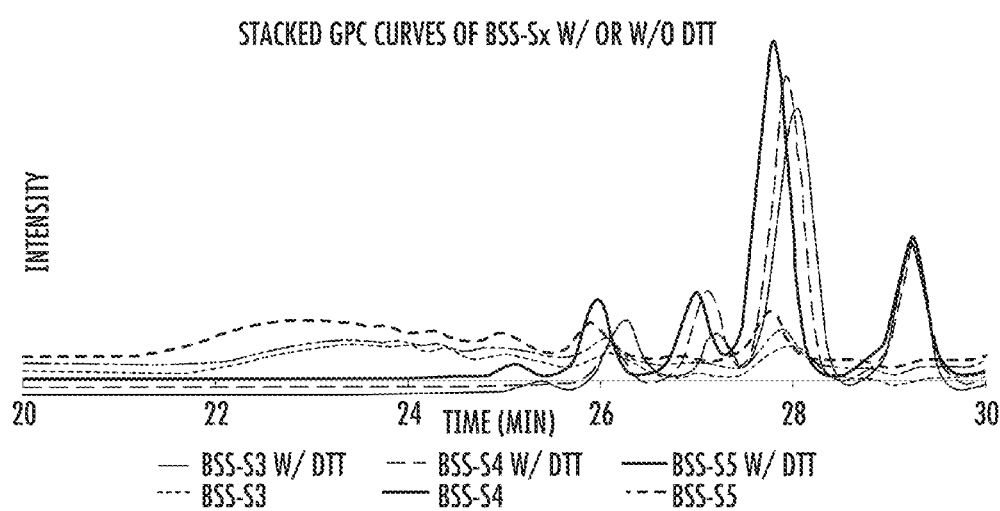
Figure 11:
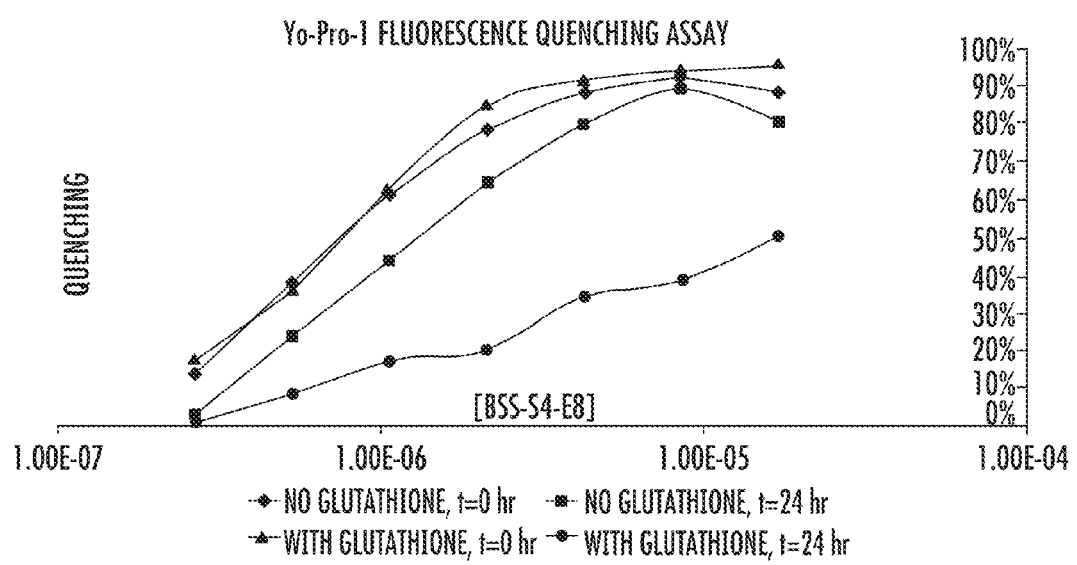
Figure 12:
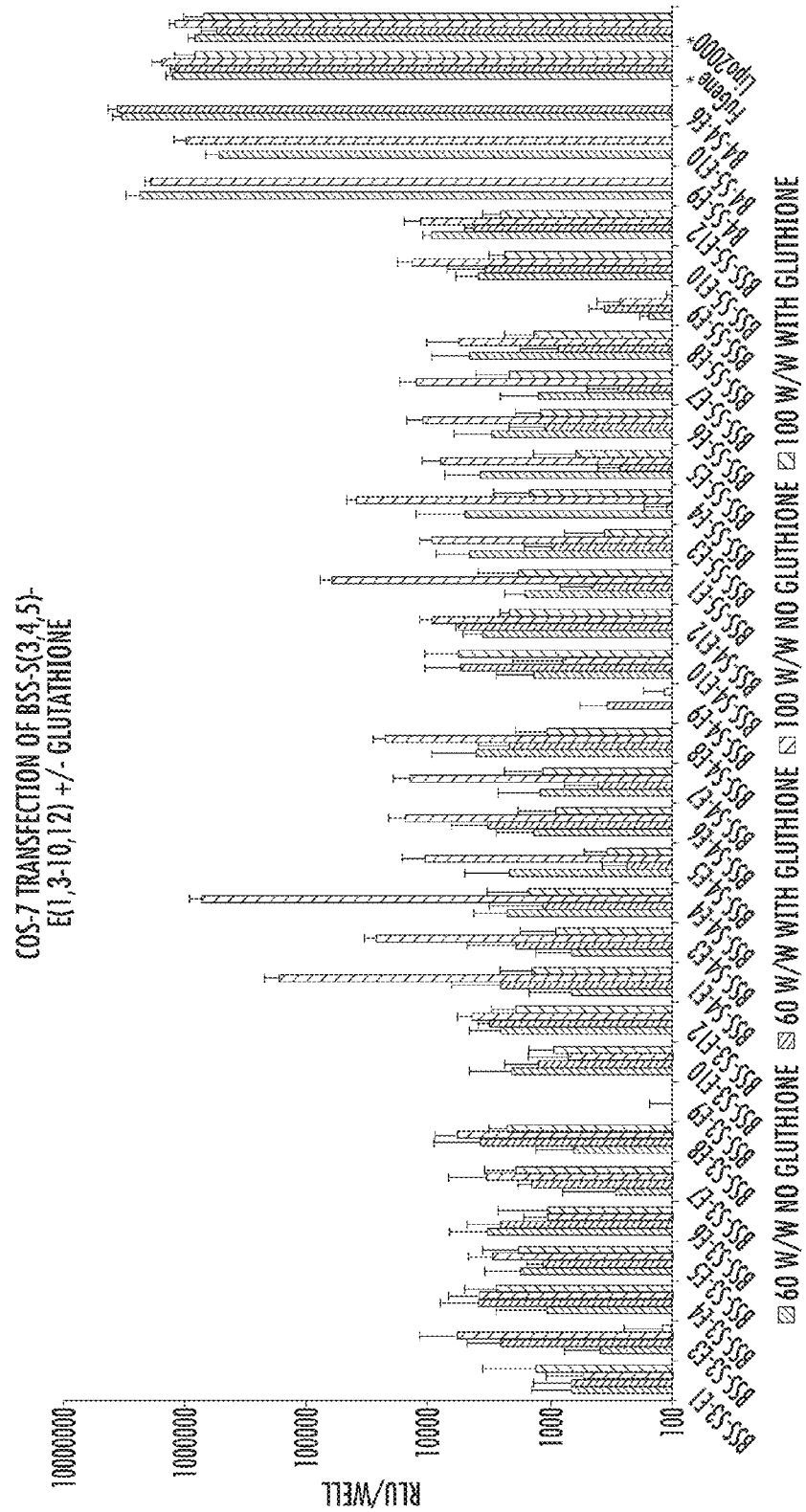
Figure 13:
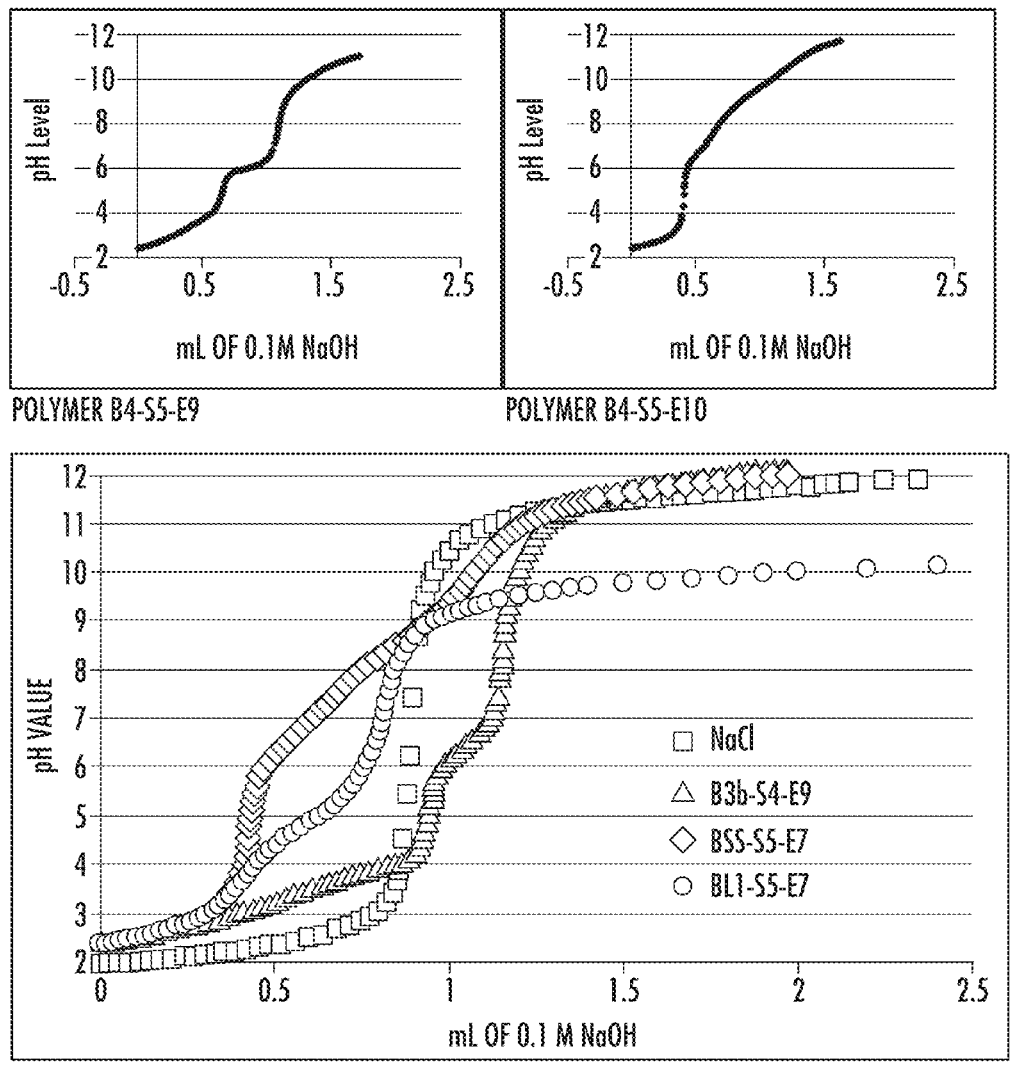
Figure 14:
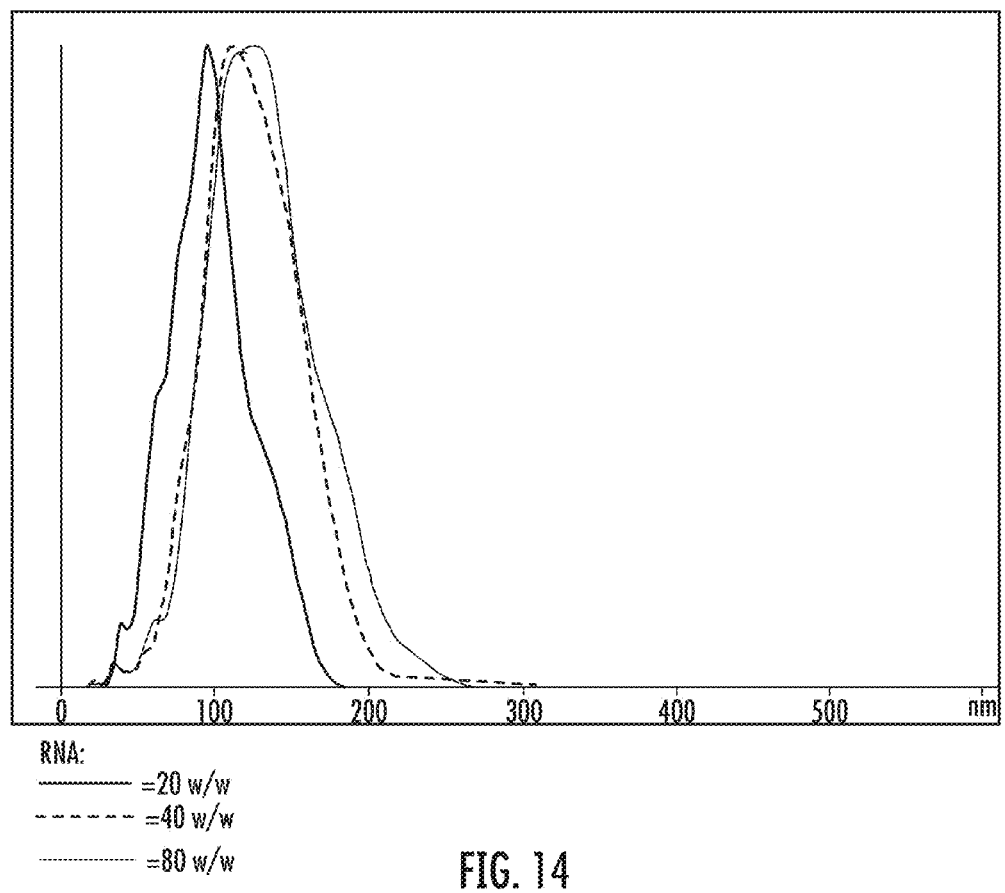
Figure 15:
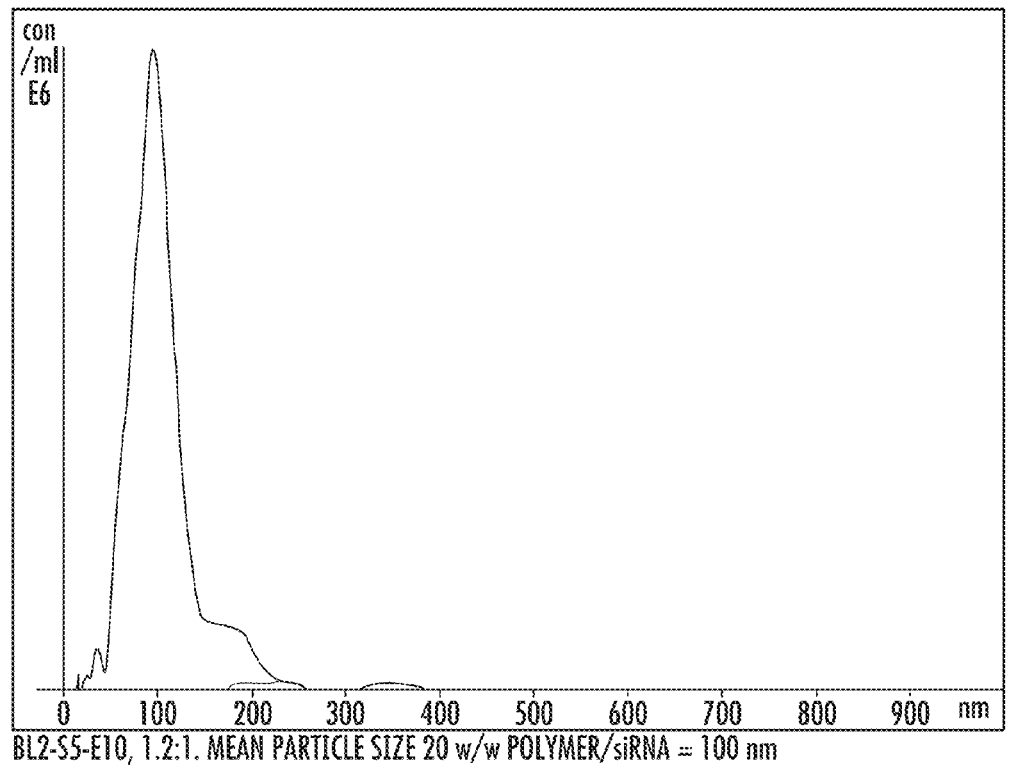
Figure 15:
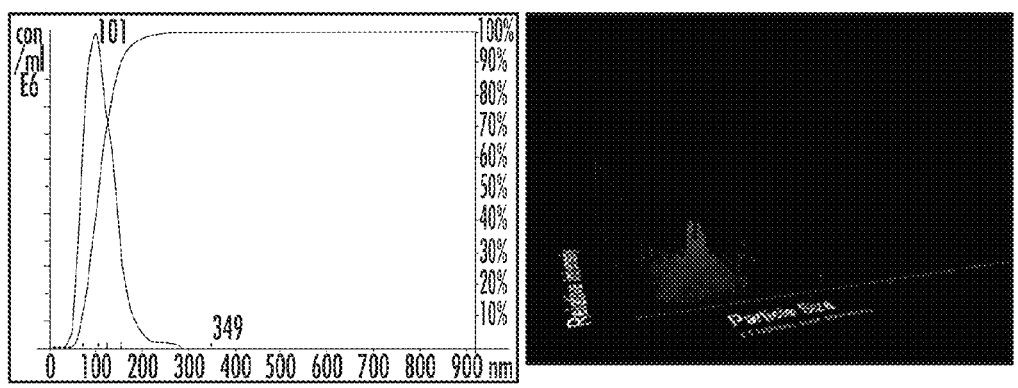
Figure 16:
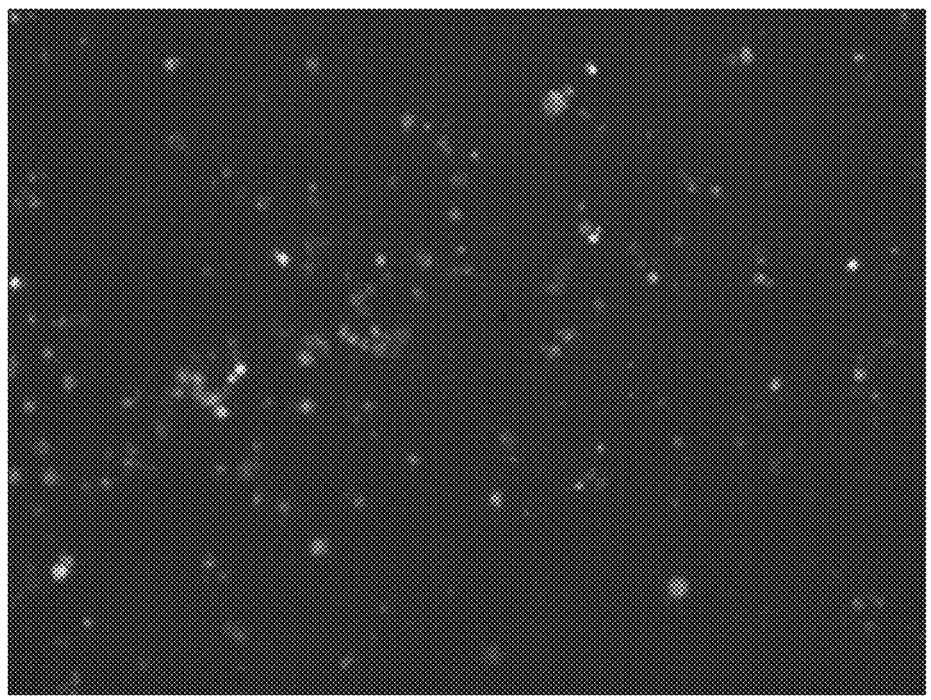
Figure 17:
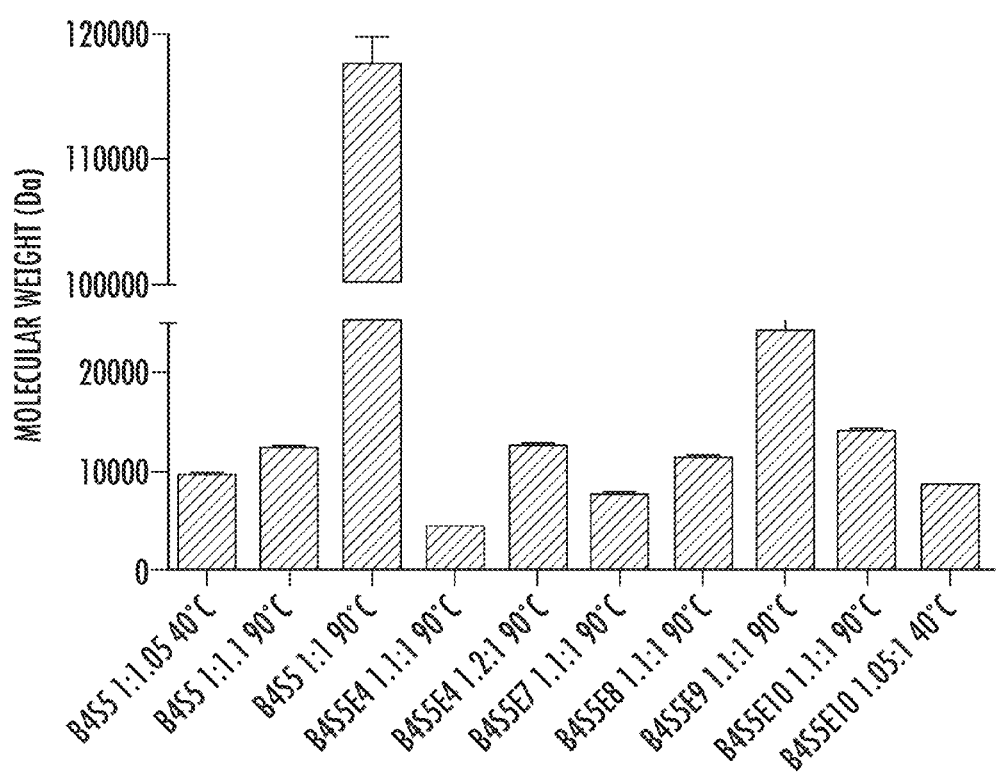

FIG. 8 shows a presently disclosed polymer (B4-S5-E10 (60 w/w)) and GBM cells by microscopy. Direct delivery of DNA/indirect delivery of RNA to glioblastoma multiforme (GBM) human brain cancer cells. The Green Fluorescent Protein (GFP) image shows that many of these cells actively transcribe and translate this DNA to generate the GFP expression. The delivered plasmid could encode various shRNA molecules that are active within the cell instead of or in addition to GFP. This is an indirect method of RNA delivery. Polymer B4-S5-E10 in human GBM cells;

FIG. 9 shows analytical data characterizing the synthesis of generic base polymer, i.e., a precursor, designated B4-S5;

FIG. 10 shows six curves from a single gel permeation chromatography run. Each bioreducible base polymer (5 mg/mL) was run with or without a reducing agent, dithiothreitol (DTT), at 5 mM concentration. The broad peak on the left for each of the polymers disappears with addition of the reducing agent which also causes an increase in the small molecular weight monomer peaks to the right of the figure;

FIG. 11 shows a competitive binding assay demonstrating that addition of glutathione to a bioreducible polymer significantly reduces the binding affinity of the polymer to DNA. This property helps the particles unpack more efficiently inside cells to release active agents and cargos. The assay compares the quenching of Yo-Pro-1:DNA complexes over various polymer concentrations;

FIG. 12 shows bioreducible, multi-component polymers that were used for gene delivery at 600 ng/well DNA. The best BSS based polymers (designated BSS-S4-E4 and BSS-S4-E1) obtained signals that were 215× and 50× higher than untreated wells, respectively. Additionally, end-capping generic base polymer B4-S5 with two reducible end groups made two new effective polymers, which combine hydrolytic degradation with disulfide reduction of the end groups. These polymers have comparable efficacy to FUGENE HD® and LIPOFECTAMINE 2000™, and other highly effective degradable polymers. The best bioreducible polymer formulations demonstrate significantly reduced transfection in the presence of 5 mM glutathione (all controls unaffected);

FIG. 13 is the titration of representative presently disclosed polymers (e.g., B4-S5-E9, B4-S5-E10, BSS-S5-E7, and the like) showing that they can buffer the pH of the endosomal compartment (pH~6) as is needed to protect drug delivery agents and facilitate endosomal rupture through the proton sponge effect. This characteristic is representative of other presently disclosed polymers, which have a range of buffering capacities. Buffering the endosome (or lack of buffering) is important to facilitate endosomal escape (or endosome targeting) and also to protect the agent being delivered;

FIG. 14 shows polymer/siRNA particle size (nm) as a function of formulation conditions (weight ratio polymer to RNA) for a representative presently disclosed polymer designated B5-S3-E9 (1.2:1 ratio for B5-S3). The formulations of the particles can be tuned to vary biophysical properties of the particle and their release;

FIG. 15 shows the particle size/biophysical characterization of polymer/siRNA nanoparticles formed by a presently disclosed polymer designated BL2-S5-E10, 1.2:1. Mean particle size 20 w/w polymer/siRNA=100 nm. The lower panels show RNA encapsulation by the presently disclosed polymers and the resulting particle size distribution. Size depends on polymer type and formulation conditions;

FIG. 16 shows direct delivery of siRNA to brain cancer cells using polymeric nanoparticles comprising a presently disclosed polymer designated B5-S3-E9. Brain cancer cells containing FITC-labeled siRNA molecules are shown as bright regions on this image;

FIG. 17 shows the molecular weights of ten B4-S5-based polymers including B4-S5-E9 and B4-S5-E10. Molecular weight is in Dalton (Da). Ratios are molar monomer ratios (B4:S5) used during polymer synthesis.

Figure 18:
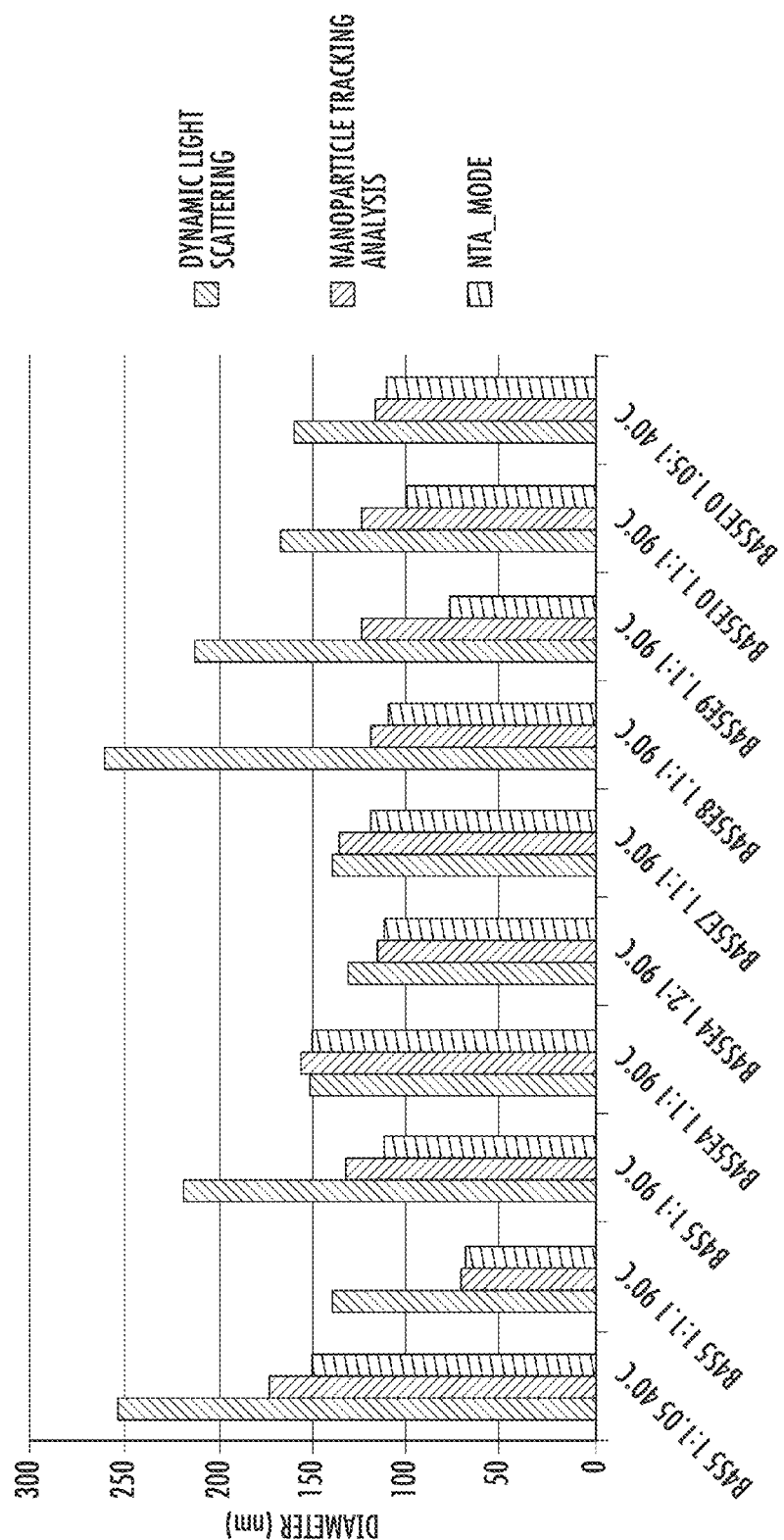
Figure 19:
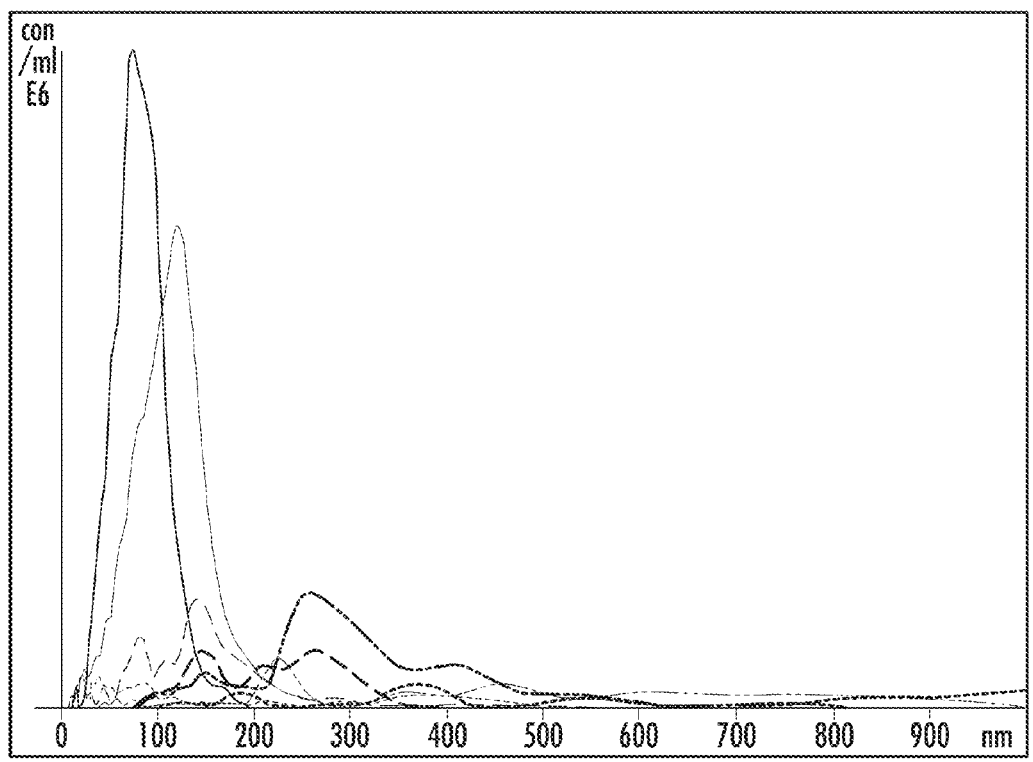
Figure 20:
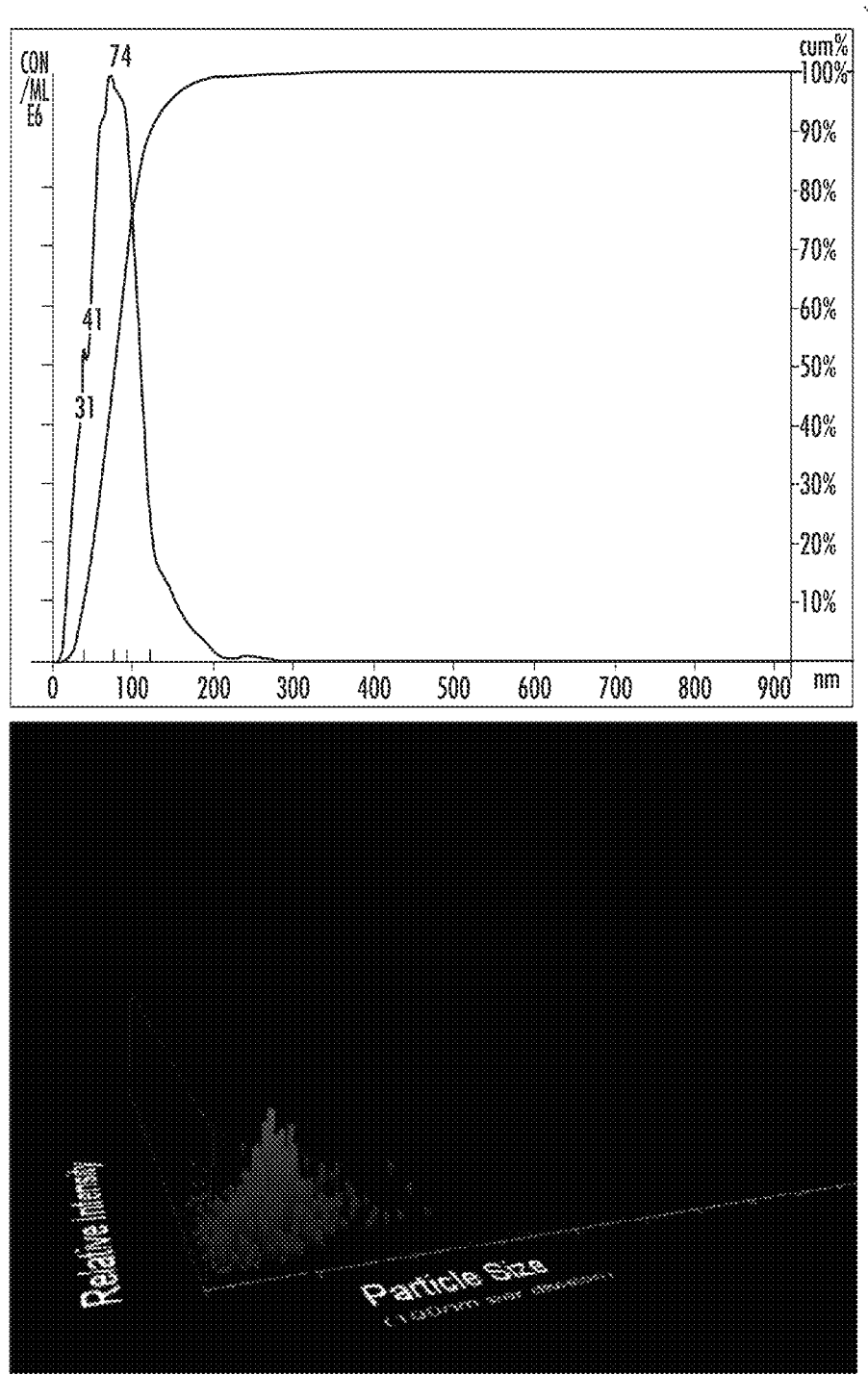
Figure 21:
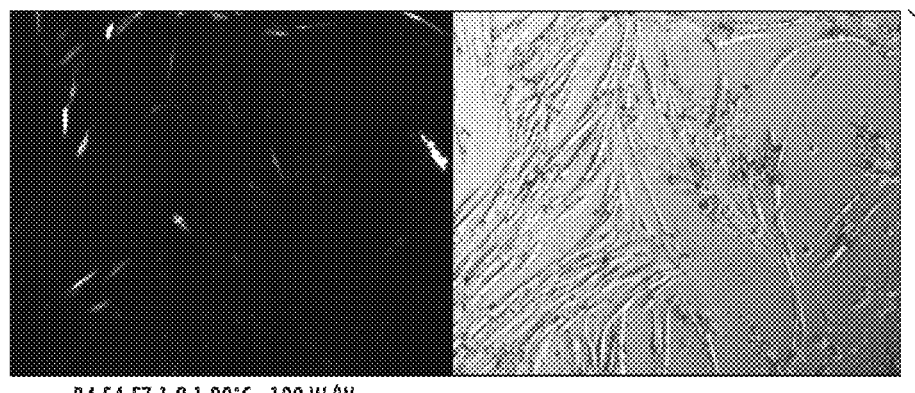
Figure 21:
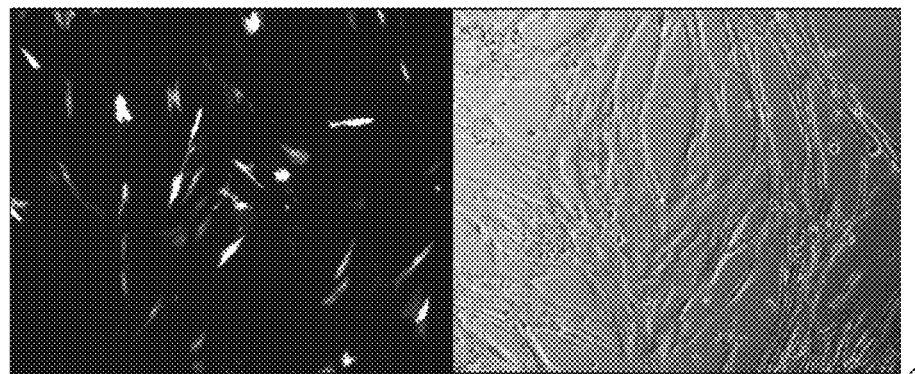
Figure 22:
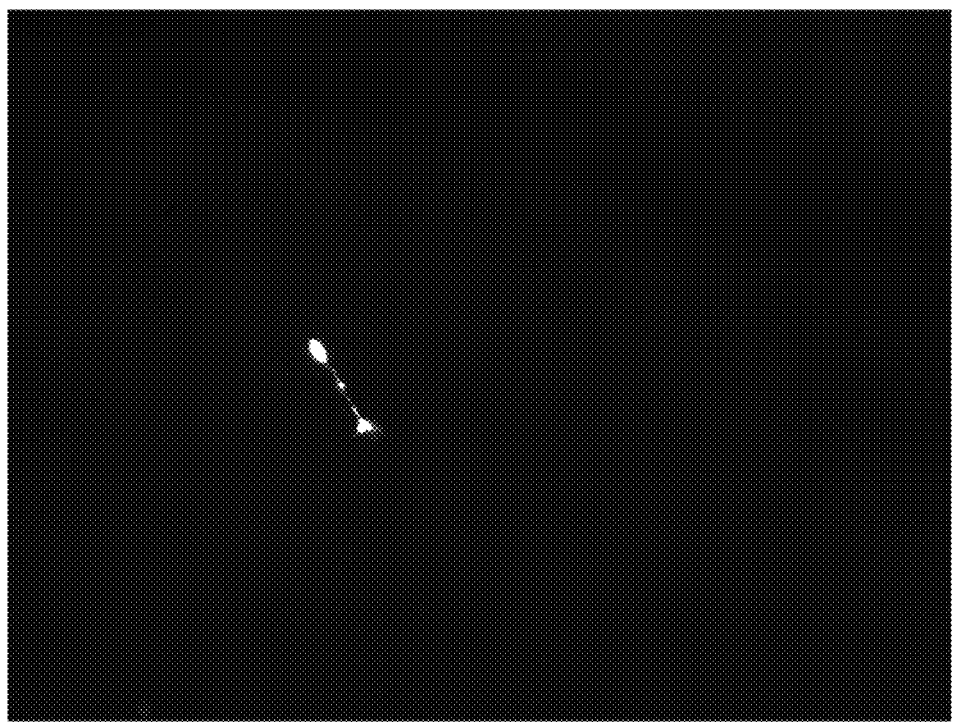
Figure 23:
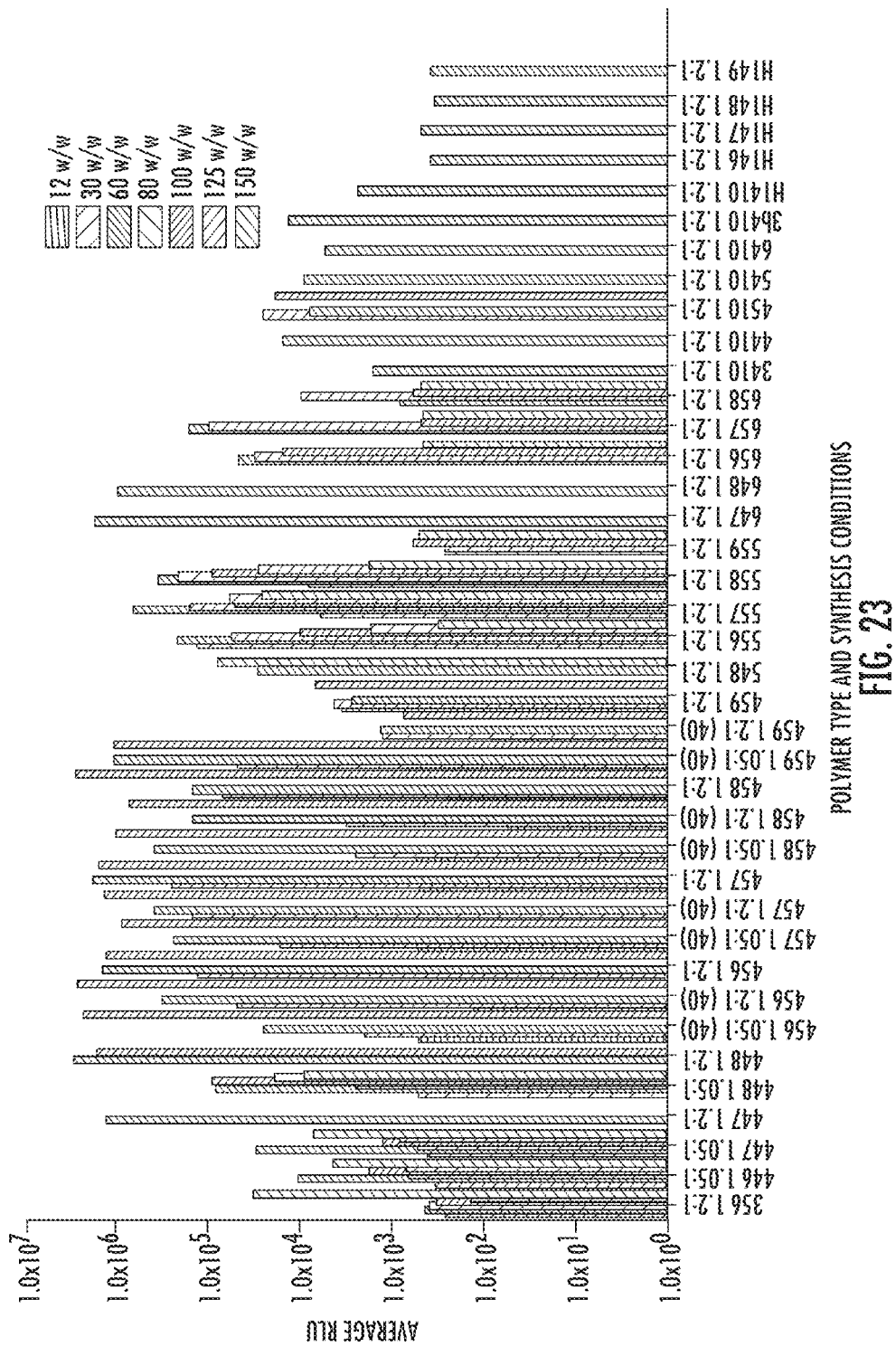
Figure 24:
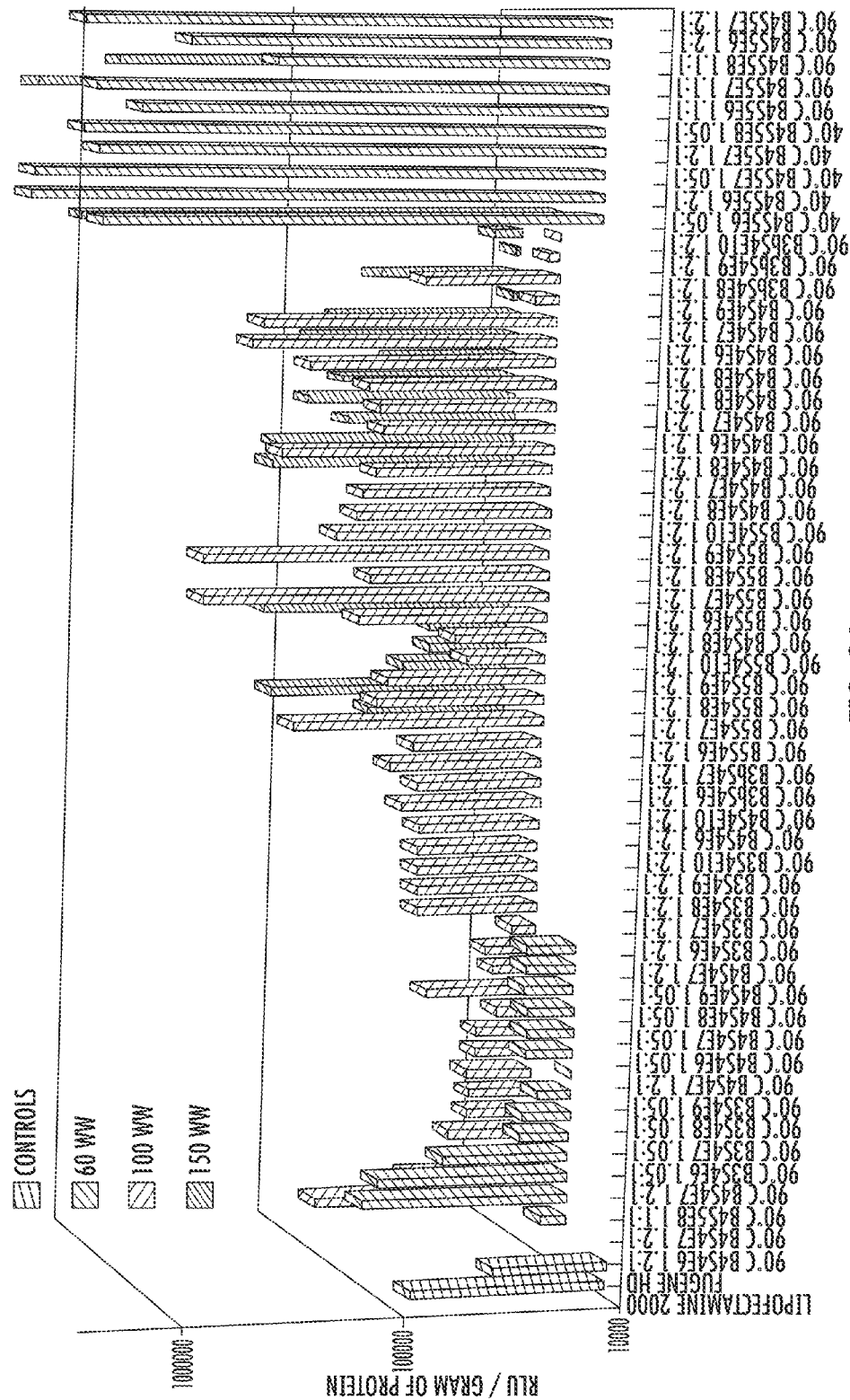
Figure 25:
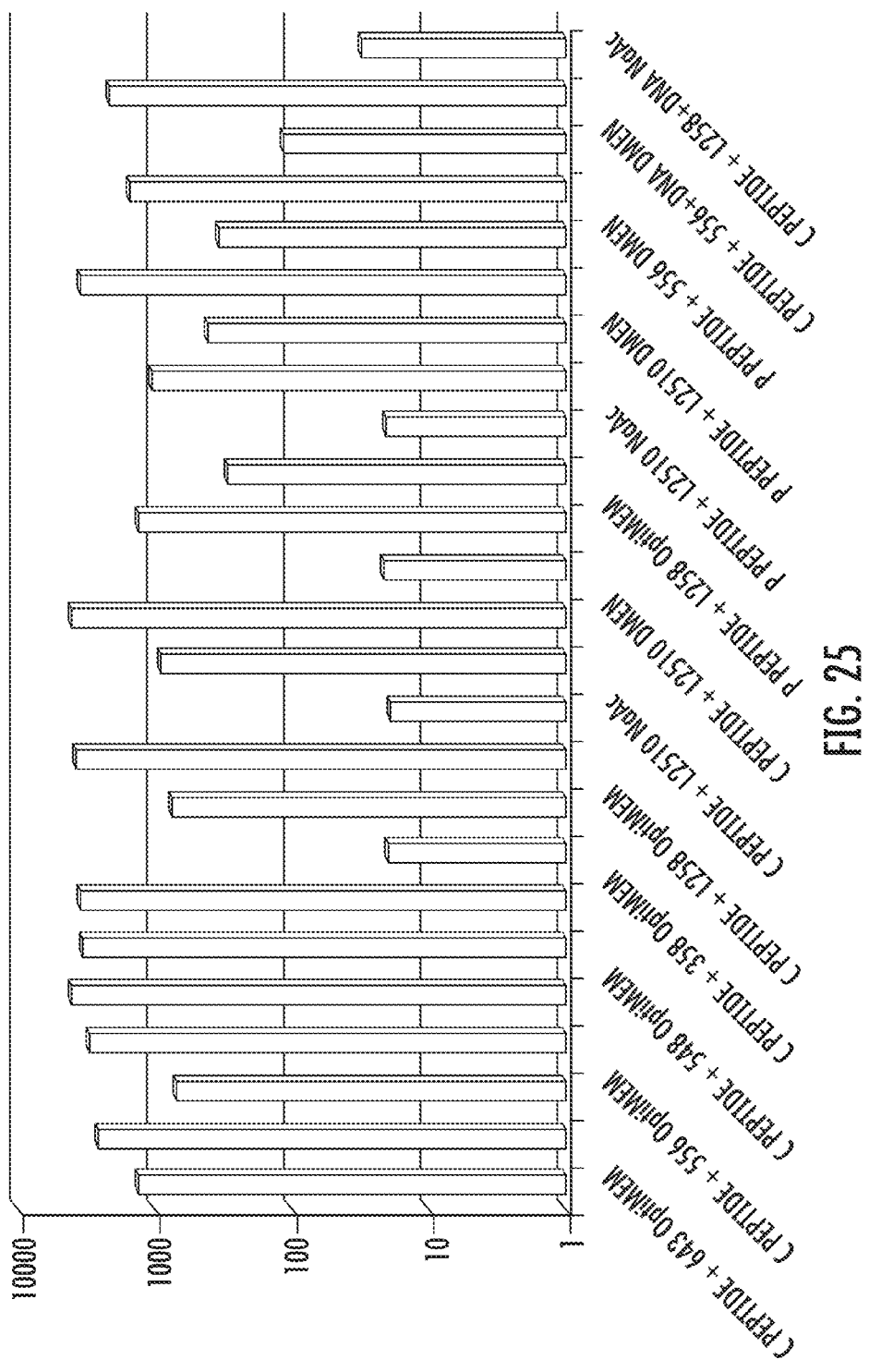

FIG. 18 shows the particle sizing data of nanoparticles formed by self-assembly of B4-S5-based polymers including B4-S5-E9 and B4-S5-E10 with enhanced green fluorescent protein (EGFP) DNA. The particles were sized using two techniques: Dynamic Light Scattering (intensity-weighted mean) and Nanoparticle Tracking Analysis (NTA). NTA was used to determine both the direct number-weighted mean and the mode;

FIG. 19 shows particle sizing data of nanoparticles formed by polymer B6-S4-E8 and a representative hydrophilic/negatively charged synthetic peptide (11-mer that includes 5 glutamic acid residues). Peak of blue curves shows particle sizes of ~100 nm for the particles when formulated at a 5:1 polymer to peptide mass ratio. Relative particle concentration for alternative formulations are also shown (Dark blue is a 1:1 ratio, Green is a 10:1 ratio);

FIG. 20 shows particle sizing data of nanoparticles formed by polymer BL1-S4-E1 and a representative hydrophobic peptide (SPWSPCSTSCGLGVSTRI). Peak of number distribution of nanoparticles is 74 nm for a polymer to peptide mass ratio of 1:1;

FIG. 21 shows transfection of IMR90s 48 hours post addition of nanoparticles. GFP expression is shown on the left panels and cell viability on the right. Polymer formulations are B4-S4-E7 1.2:1 100 w/w, 90° C. (top panels) and B5-S3-E7 1.05:1 100 w/w 90° C. (bottom panels);

FIG. 22 shows transfection of a retinal neuron with a representative polymer (B4-S4-E8 (60 w/w)). GFP is expressed brightly and morphological structures are good;

FIG. 23 shows transfection of a luciferase gene across many representative polymers. Each polymer is able to form nanoparticles that deliver genes to COS-7 cells. The polymers were synthesized at 90° C. unless indicated as 40° C. Tuning the polymer backbone monomer, side group monomer, terminal group monomer, monomer ratio during synthesis, synthesis temperature, and nanoparticle formulation ratio (w/w) each independently varies overall gene delivery efficacy;

FIG. 24 shows transfection of a luciferase gene across many representative polymers. Each polymer is able to form nanoparticles that deliver genes to primary human fibroblasts, IMR-90s. The polymers were synthesized at 90° C. unless indicated as 40° C. Tuning the polymer backbone monomer, side group monomer, terminal group monomer, monomer ratio during synthesis, synthesis temperature, and nanoparticle formulation ratio (w/w) each independently varies overall gene delivery efficacy. FIGS. 5, 6, 23, and 24, demonstrate that representative embodiments of the presently disclosed polymers also can exhibit cell-type specificity; and FIG. 25 shows polymer/peptide particle size depends on polymer structure, formulation conditions including buffer, and peptide that is being encapsulated. All sizing was conducted by dynamic light scattering and volume-averaged sizes are reported. All formulations were at 10 weight polymer to 1 weight peptide. "C" refers to peptide NGRKACLNPASPIVKKIIEKMLNS and "P" refers to peptide LRRFSTMPFMFCNINNVCNF.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

I. MULTICOMPONENT DEGRADABLE CATIONIC POLYMERS

The presently disclosed subject matter generally provides multicomponent degradable cationic polymers. In some embodiments, the presently disclosed polymers have the property of biphasic degradation. Modifications to the polymer structure can result in a change in the release of therapeutic agents, which can occur over multiple time scales. In some embodiments, the presently disclosed polymers include a minority structure, e.g., an endcapping group, which differs from the majority structure comprising most of the polymer backbone. In other embodiments, the bioreducible oligomers form block copolymers with hydrolytically degradable oligomers. In yet other embodiments, the end group/minority structure comprises an amino acid or chain of amino acids, while the backbone degrades hydrolytically and/or is bioreducible.

As described in more detail herein below, small changes in the monomer ratio used during polymerization, in combination with modifications to the chemical structure of the end-capping groups used post-polymerization, can affect the efficacy of delivery of a therapeutic agent, including, but not limited to a gene, to a target. Further, changes in the chemical structure of the polymer, either in the backbone of the polymer or end-capping groups, or both, can change the efficacy of gene delivery to a cell, e.g., a cancerous fibroblast line or a human primary fibroblast. In some embodiments, small changes to the molecular weight of the polymer or changes to the endcapping groups of the polymer, while leaving the main chain, i.e., backbone, of the polymer the same, can enhance or decrease the overall delivery of the gene to a cell. Further, the "R" groups that comprise the backbone or main chain of the polymer can be selected to degrade via different biodegradation mechanisms within the same polymer molecule. Such mechanisms include, but are not limited to, hydrolytic, bioreducible, enzymatic, and/or other modes of degradation.

In some embodiments, the presently disclosed compositions can be prepared according to Scheme 1:

Scheme 1. Representative synthesis scheme for preparing the presently disclosed cationic polymers having biphasic biodegradation.

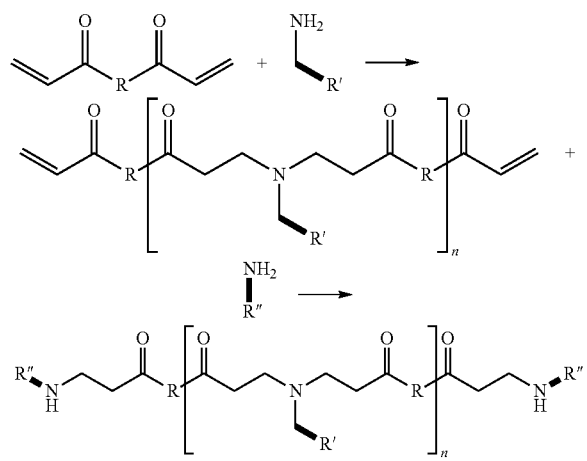

In some embodiments, at least one of the following groups R, R', and R" contain reducible linkages and, for many of the presently disclosed materials, additional modes of degradation also are present. More generally, R' can be any group that facilitates solubility in water and/or hydrogen bonding, for example, OH, $NH_2$ and SH. Representative degradable linkages include, but are not limited to:

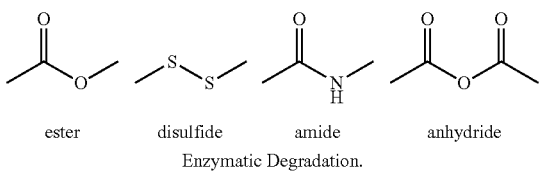

ester     disulfide     amide     anhydride

Enzymatic Degradation.

The end group structures, i.e., R" groups in Scheme 1, for the presently disclosed cationic polymers are distinct and separate from the backbone structures (R) structures, the side chain structures (R'), and end group structures of the intermediate precursor molecule for a given polymeric material.

More particularly, in some embodiments, the presently disclosed subject matter includes a compound of formula (I):

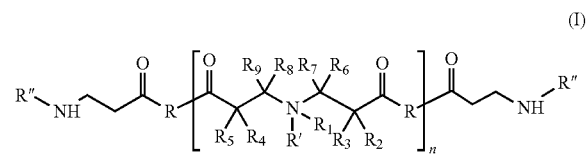

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and at least one of R, R', and R" comprise a reducible or degradable linkage, and wherein each R, R', or R" can independently be the same or different;

under the proviso that when at least one R group comprises an ester linkage of the formula —C(=O)—O— and the compound of formula I comprises a poly(beta-amino ester), then the compound of formula (I) must also comprise one or more of the following characteristics:

(a) each R group is different;
(b) each R" group is different;
(c) each R" group is not the same as any of R', $R_1$, $R_2$, $R_3$, $R_4$, $R_5$, $R_6$, $R_7$, $R_8$, and $R_9$;
(d) the R" groups degrade through a different mechanism than the ester-containing R groups, wherein the degradation of the R" group is selected from the group consisting of a bioreducible mechanism or an enzymatically degradable mechanism; and/or
(e) the compound of formula (I) comprises a substructure of a larger cross-linked polymer, wherein the larger cross-linked polymer comprises different properties from compound of formula (I).

In other embodiments, the compound of formula (I) is subject to the further proviso that if at least one R group comprises an ester linkage, then the R" groups impart one or more of the following characteristics to the compound of formula (I): independent control of cell-specific uptake and/or intracellular delivery of a particle; independent control of endosomal buffering and endosomal escape; independent control of DNA release; triggered release of an active agent; modification of a particle surface charge; increased diffusion through a cytoplasm of a cell; increased active transport through a cytoplasm of a cell; increased nuclear import within a cell; increased transcription of an associated DNA within a cell; increased translation of an associated DNA within a cell; increased persistence of an associated therapeutic agent within a cell, wherein the therapeutic agent is selected from the group consisting of DNA, RNA, a peptide or a protein.

More particularly, any poly(beta-amino ester) specifically disclosed or claimed in U.S. Pat. No. 6,998,115; U.S. Pat. No. 7,427,394; U.S. patent application publication no. US2005/0265961; and U.S. patent publication no. US2010/0036084, each of which is incorporated herein by reference in its entirety, is explicitly excluded from the presently disclosed compounds of formula (I). In particular, the poly (beta-amino ester)s disclosed in U.S. Pat. No. 6,998,115; U.S. Pat. No. 7,427,394; U.S. patent application publication no. US2005/0265961; and U.S. patent publication no. US2010/0036084 are symmetrical, i.e., both R groups as defined in formula (I) herein are the same. In certain embodiments of the presently disclosed compounds of formula (I), when at least one R comprises an ester linkage, the two R groups of formula (I) are not the same, i.e., in such embodiments, the compounds of formula (I) are not symmetrical.

In particular embodiments, the reducible or degradable linkage comprising R, R', and R" is selected from the group consisting of an ester, a disulfide, an amide, an anhydride or a linkage susceptible to enzymatic degradation, subject to the above-mentioned provisos.

Further, in some embodiments of the compound of formula (I), n is an integer from 1 to 1,000; in other embodiments, n is an integer from 1 to 100; in other embodiments, n is an integer from 1 to 30; in other embodiments, n is an integer from 5 to 20; in other embodiments, n is an integer from 10 to 15; and in other embodiments, n is an integer from 1 to 10.

In some embodiments, R" can be an oligomer as described herein, e.g., one fully synthesized primary amine-terminated oligomer, and can be used as a reagent during the second reaction step of Scheme I. This process can be repeated iteratively to synthesize increasingly complex molecules.

In other embodiments, R" can comprise a larger biomolecule including, but not limited to, poly(ethyleneglycol) (PEG), a targeting ligand, including, but not limited to, a sugar, a small molecule, an antibody, an antibody fragment, a peptide sequence, or other targeting moiety known to one skilled in the art; a labeling molecule including, but not limited to, a small molecule, a quantum dot, a nanoparticle, a fluorescent molecule, a luminescent molecule, a contrast agent, and the like; and a branched or unbranched, substituted or unsubstituted alkyl chain.

In some embodiments, the branched or unbranched, substituted or unsubstituted alkyl chain is about 2 to about 5 carbons long; in some embodiments, the alkyl chain is about 6 to about 8 carbons long; in some embodiments, the alkyl chain is about 9 to about 12 carbons long; in some embodiments, the alkyl chain is about 13 to about 18 carbons long; in some embodiments, the alkyl chain is about 19 to about 30 carbons long; in some embodiments, the alkyl chain is greater than about 30 carbons long.

In certain embodiments, both R" groups, i.e., the end groups of the polymer, comprise alkyl chains. In other embodiments, only one R" group comprises an alkyl chain. In some embodiments, at least one alkyl chain is terminated with an amino ($NH_2$) group. In other embodiments, the at least one alkyl chain is terminated with a hydroxyl (OH) group.

In some embodiments, the PEG has a molecular weight of about 5 kDa or less; in some embodiments, the PEG has a molecular weight of about 5 kDa to about 10 kDa; in some embodiments, the PEG has a molecular weight of about 10 kDa to about 20 kDa; in some embodiments, the PEG has a molecular weight of about 20 kDa to about 30 kDa; in some embodiments, the PEG is greater than 30 kDa. In certain embodiments, both R" groups comprise PEG. In other embodiments, only one R" group comprises PEG.

Further, in some embodiments, one R" group is PEG and the other R" group is a targeting ligand and/or labeling molecule as defined herein above. In other embodiments, one R" group is an alkyl chain and the other R" group is a targeting ligand and/or labeling molecule.

Representative monomers used to synthesize the presently disclosed cationic polymers include, but are not limited to, those provided immediately herein below. The presently disclosed subject matter is not limited to the representative monomers disclosed herein, but also includes other structures that one skilled in the art could use to create similar biphasic degrading cationic polymers Scheme 2. Example structures of backbone ("B" or R), side chain ("S" or R'), and end groups. ("E" or R").

B3　　1,3-propanediol diacrylate　　　B3b　　1,3-butanediol diacrylate

-continued

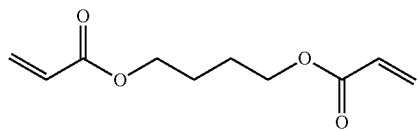
1,4-butanediol diacrylate  B4

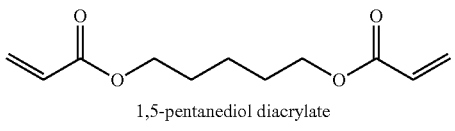
1,5-pentanediol diacrylate  B5

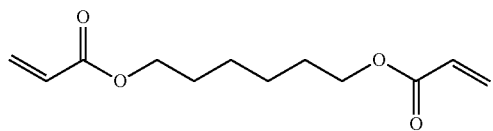
1,6-hexanediol diacrylate  B6

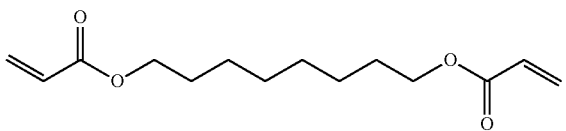
1,8-octanediol diacrylate  B8

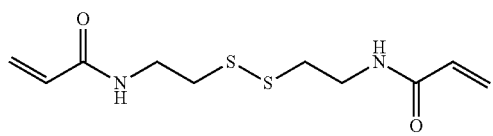
N,N′-bis(acrylyl)cystamine  BSS

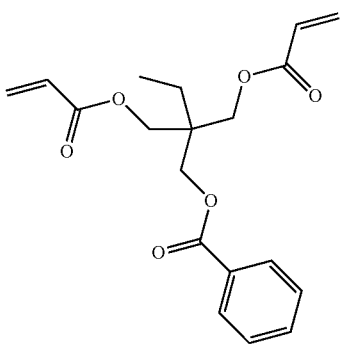
trimethylolpropane benzoate diacrylate  BL1

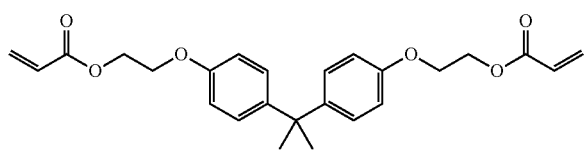
ethoxylated bisphenol A diacrylate  BL2

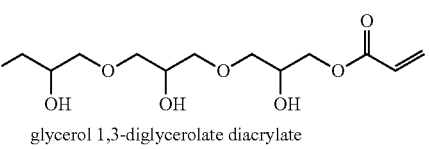
glycerol 1,3-diglycerolate diacrylate  BH1

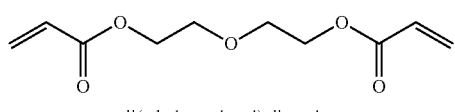
di(ethylene glycol) diacrylate  BP1

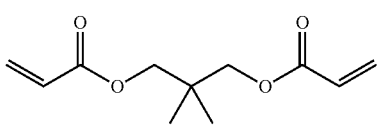
neopentyl glycol diacrylate  BP2

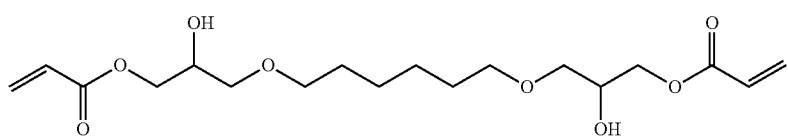
1,6-(hexanediylbis[oxy(2-hydroxy-3,1-propanediyl)] bisacrylate  BP3

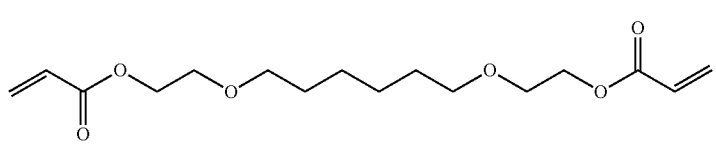
2,2′-(hexane-1,6-diylbis(oxy))bis(ethane-2,1-diyl) diacrylate  BP4

-continued

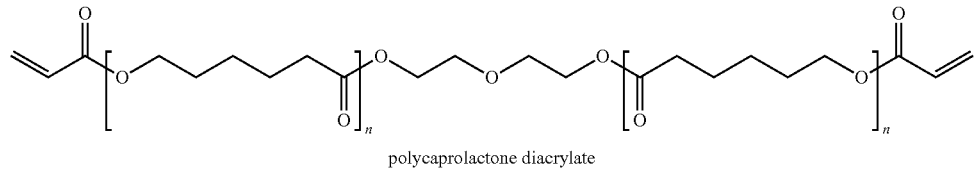
polycaprolactone diacrylate
BP5

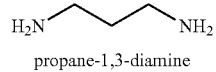
propane-1,3-diamine
E1

2,2-dimethylpropane-1,3-diamine
E2

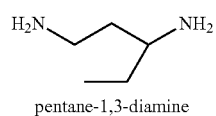
pentane-1,3-diamine
E3

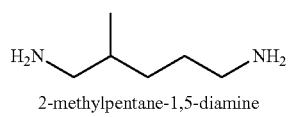
2-methylpentane-1,5-diamine
E4

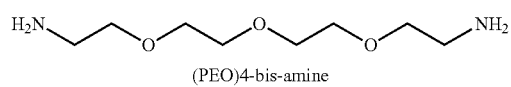
(PEO)4-bis-amine
E5

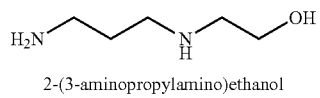
2-(3-aminopropylamino)ethanol
E6

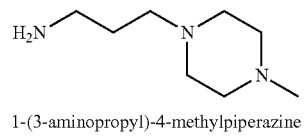
1-(3-aminopropyl)-4-methylpiperazine
E7

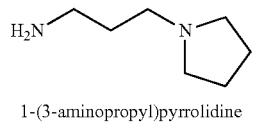
1-(3-aminopropyl)pyrrolidine
E8

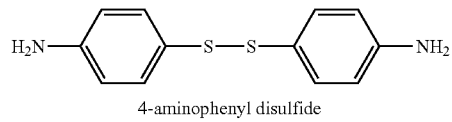
4-aminophenyl disulfide
E9

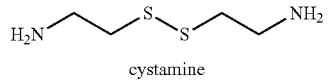
cystamine
E10

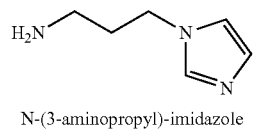
N-(3-aminopropyl)-imidazole
E11

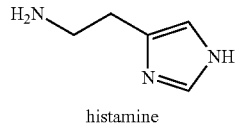
histamine
E12

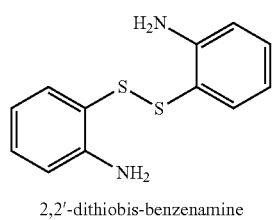
2,2'-dithiobis-benzenamine
E13

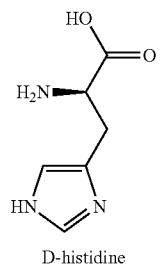
D-histidine
E14

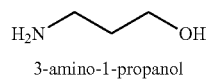
3-amino-1-propanol
S3

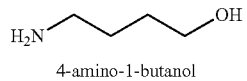
4-amino-1-butanol
S4

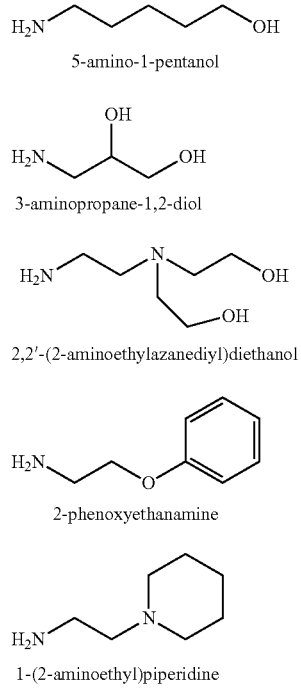

5-amino-1-pentanol (S5)

3-aminopropane-1,2-diol (S7)

2,2'-(2-aminoethylazanediyl)diethanol (S9)

2-phenoxyethanamine (S11)

1-(2-aminoethyl)piperidine (S13)

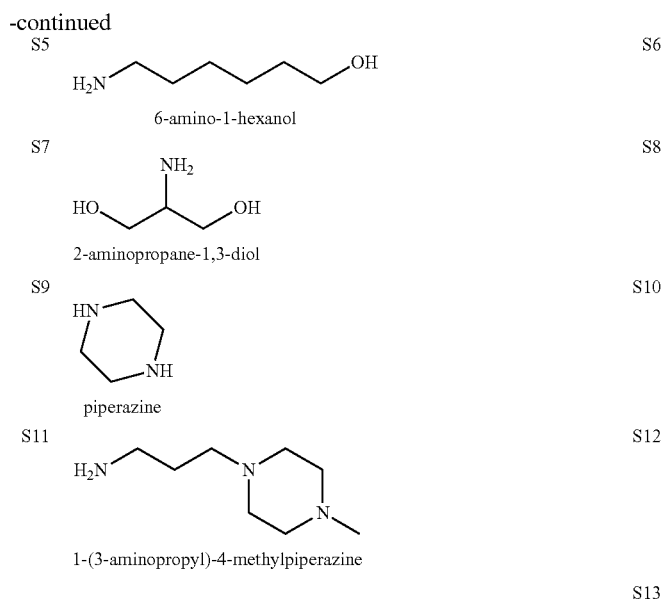

6-amino-1-hexanol (S6)

2-aminopropane-1,3-diol (S8)

piperazine (S10)

1-(3-aminopropyl)-4-methylpiperazine (S12)

In particular embodiments, as depicted in Scheme 3, the presently disclosed cationic polymers comprise a polyalcohol structure, i.e., the side chain represented by R' in Scheme 1 comprises an alcohol.

Scheme 3. Representative synthesis scheme for preparing the presently disclosed cationic polymers having an alcohol side chain.

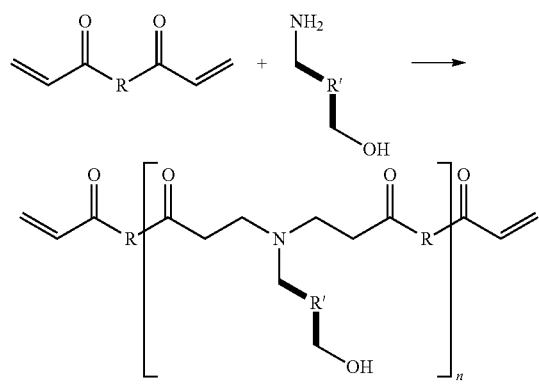

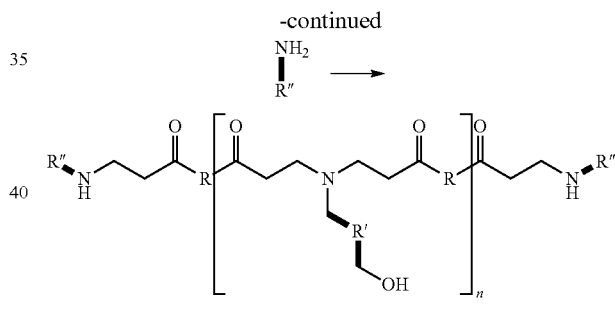

In such embodiments, the end group structures (R") and the backbone structures (R) are defined as above and the side chain must contain at least one hydroxyl (OH) group.

In yet other embodiments, the presently disclosed cationic polymer comprises a specific poly(ester amine) structure with secondary non-hydrolytic modes of degradation. In such embodiments, the cationic polymer comprises a polyester that degrades through ester linkages (hydrolytic degradation) that is further modified to comprise bioreducible groups as end (R") groups.

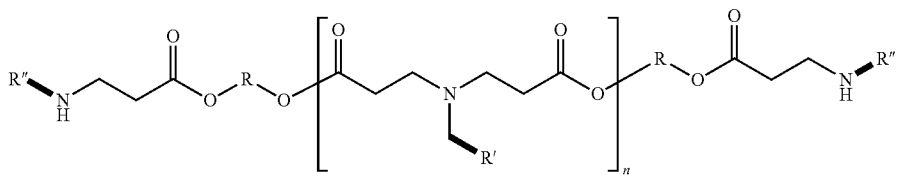

Representative bioreducible end groups in such embodiments include, but are not limited to:

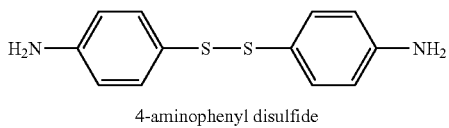

4-aminophenyl disulfide

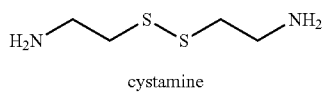

cystamine

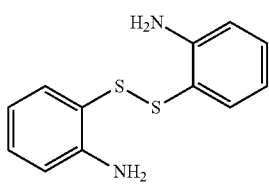

2,2'-dithiobis-benzenamine

In some embodiments, the presently disclosed cationic polymer comprises a specific poly(ester amine alcohol) structure with secondary non-hydrolytic modes of degradation. In such embodiments, the cationic polymer comprises a specific structure where a polyester that degrades through ester linkages (hydrolytic degradation) is modified to contain bioreducible groups as end groups.

In such embodiments, $R_1$ and $R_2$ are alkyl chains. In some embodiments, the alkyl chain is 1-2 carbons long; in some embodiments, the alkyl chain is 3-5 carbons long; in some embodiments, the alkyl chain is 6-8 carbons long; in some embodiments, the alkyl chain is 9-12 carbons long; in some embodiments, the alkyl chain is 13-18 carbons long; in some embodiments, the alkyl chain is 19-30 carbons long; and in some embodiments, the alkyl chain is greater than 30 carbons long Suitable non-reducible amino R" groups for such embodiments include, but are not limited to:

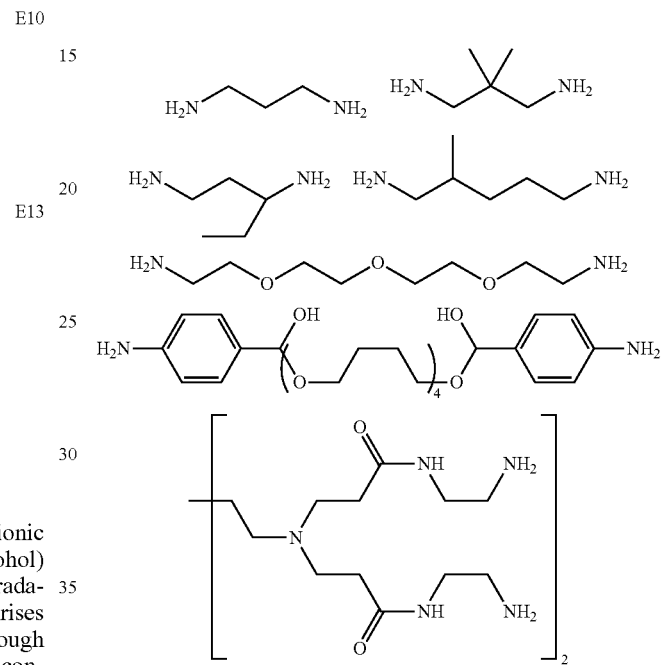

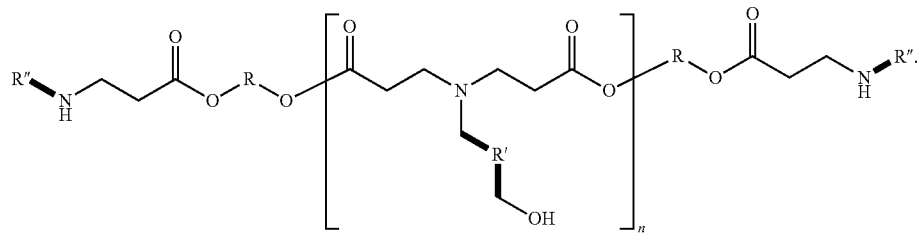

In yet other embodiments, the presently disclosed cationic polymer comprises a specific poly(amido amine) structure having disulfide linking groups in the polymer backbone and an independent, non-reducible amine contacting group at the terminal ends of the polymer.

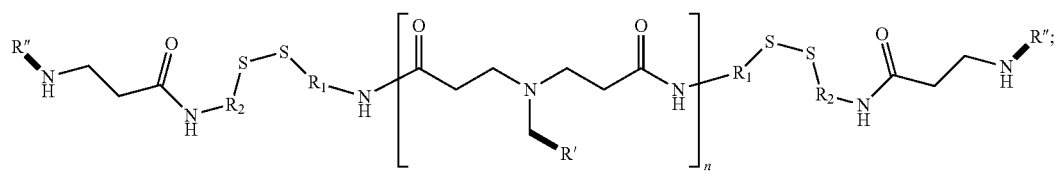

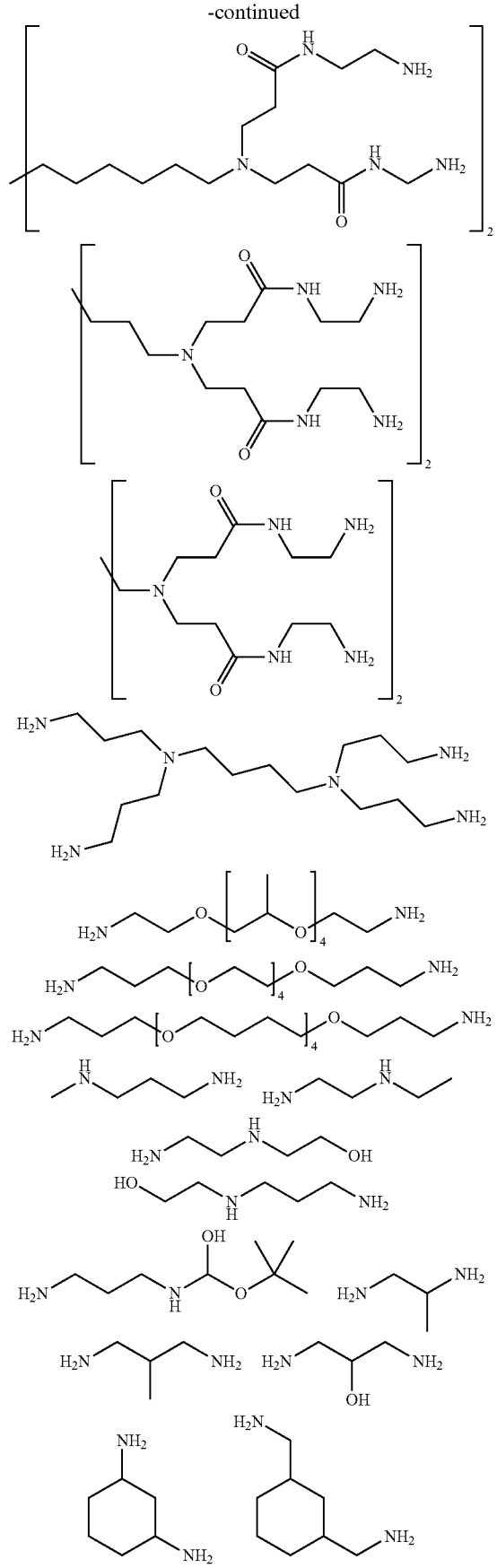
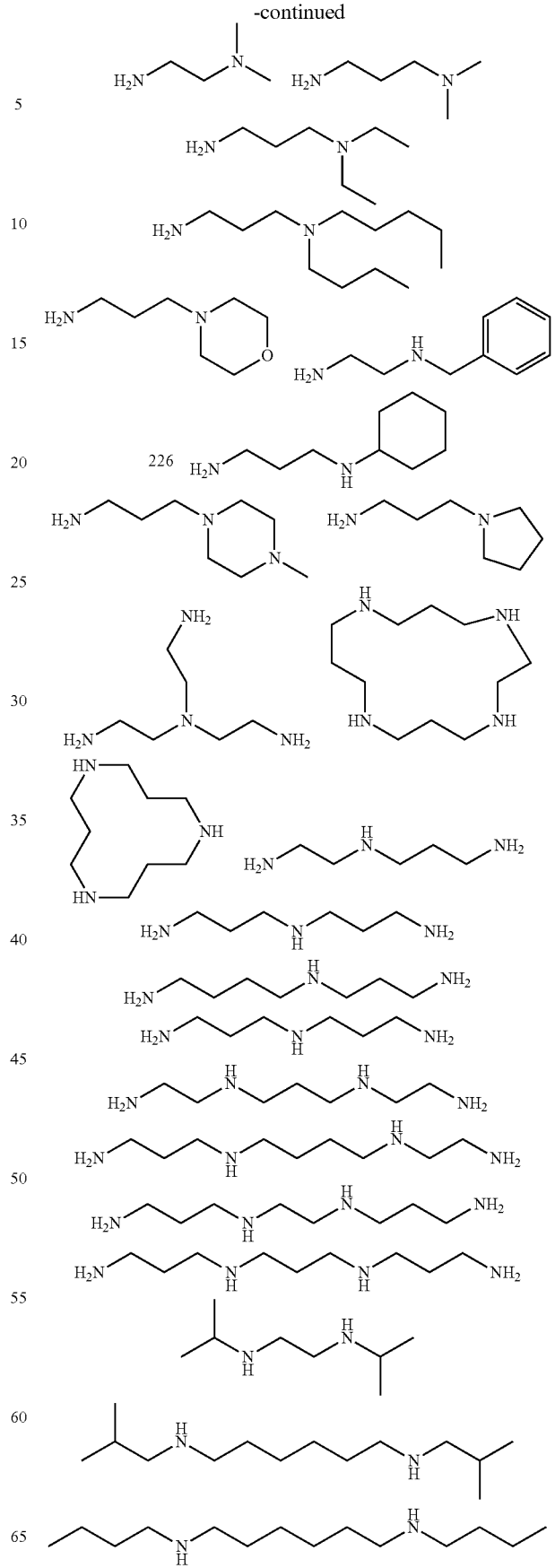

-continued

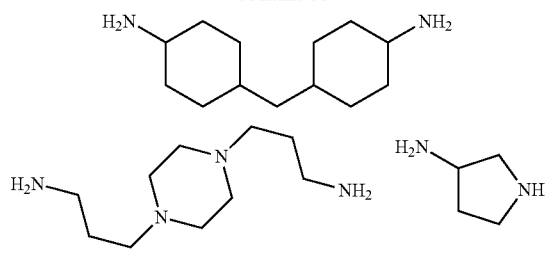

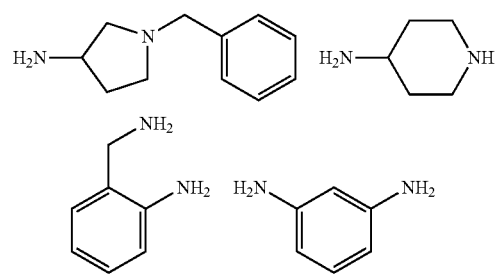

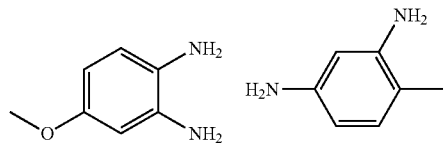

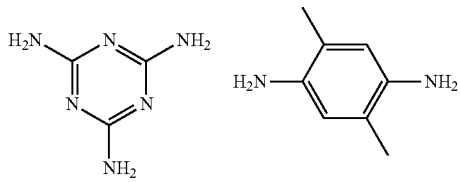

-continued

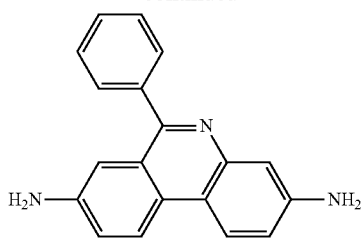

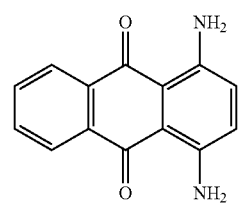

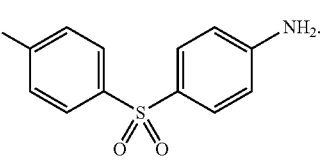

In other embodiments, the presently disclosed cationic polymers comprise a specific poly(amido amine alcohol) structure having disulfide linking groups in the polymer backbone and an independent non-reducible amine contacting group at the terminal ends of the polymer.

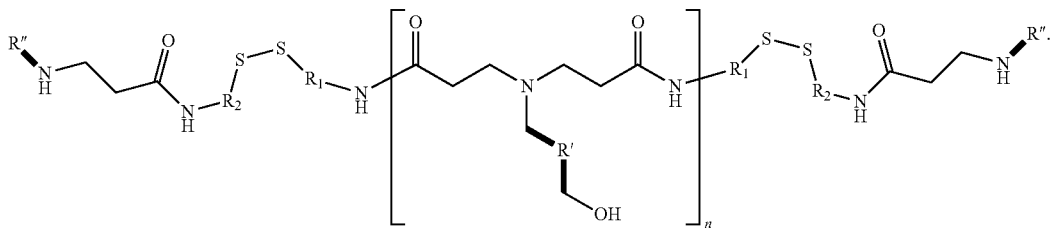

-continued

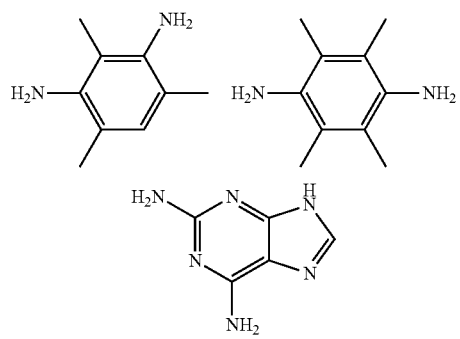

In yet other embodiments, the presently disclosed cationic polymer comprises a copolymer of representative oligomers as described hereinabove. Such embodiments include, but are not limited to, a poly(amido amine) structure having disulfides in the polymer backbone and an independently degradable (non-reducible) group at at least one end of the polymer. Such embodiments also include using a cross-linker to add bioreducible linkages to hydrolytically degradable materials and also provide for higher molecular weight materials. A representative example of this embodiment, along with suitable monomers is as follows:

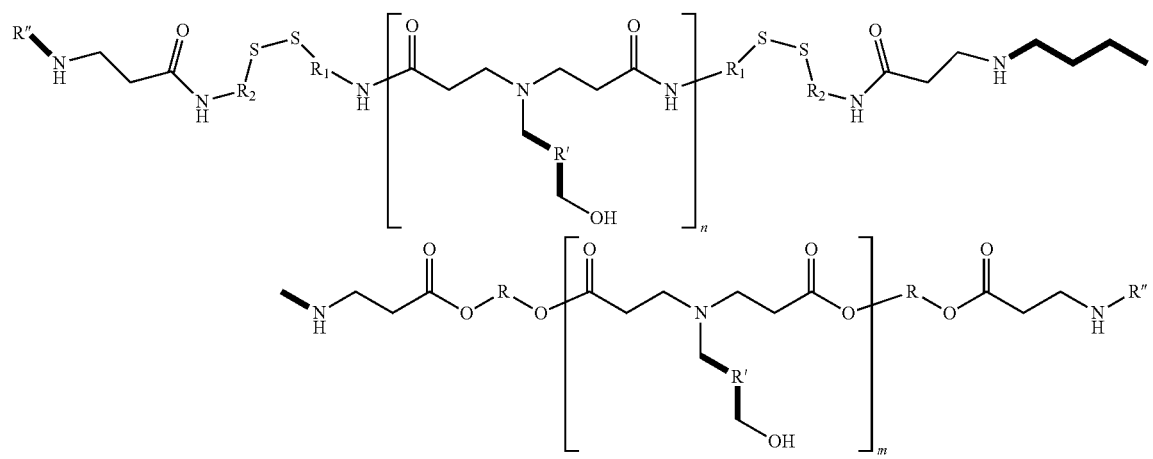
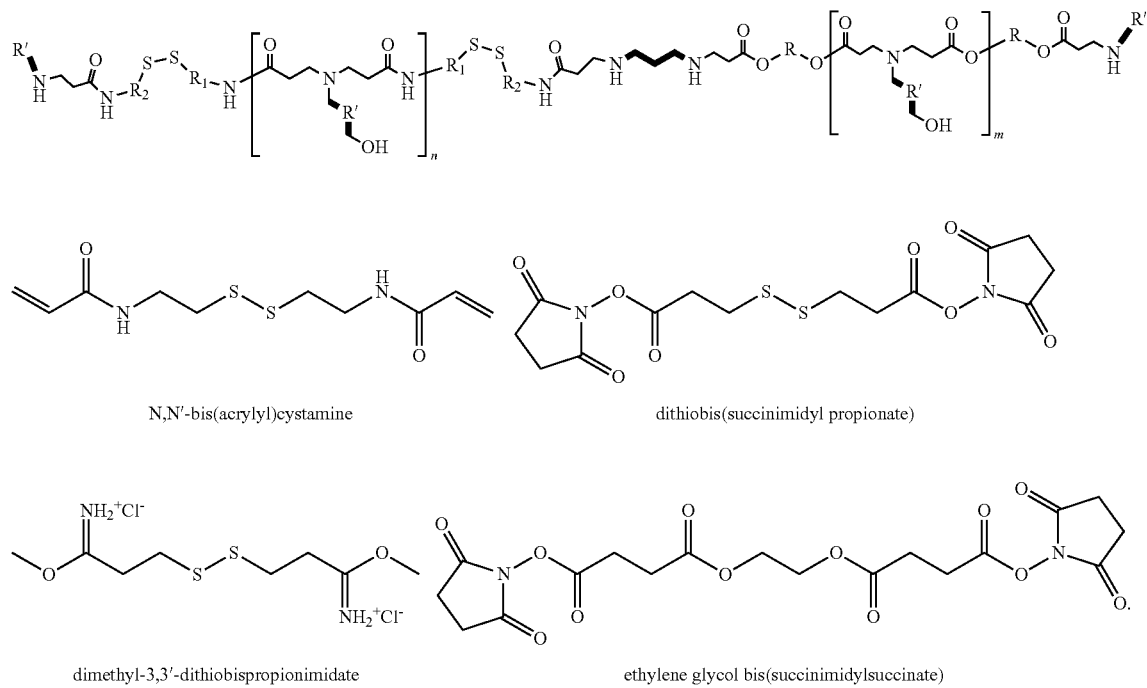
In particular embodiments, the presently disclosed polymer is selected from the group consisting of:
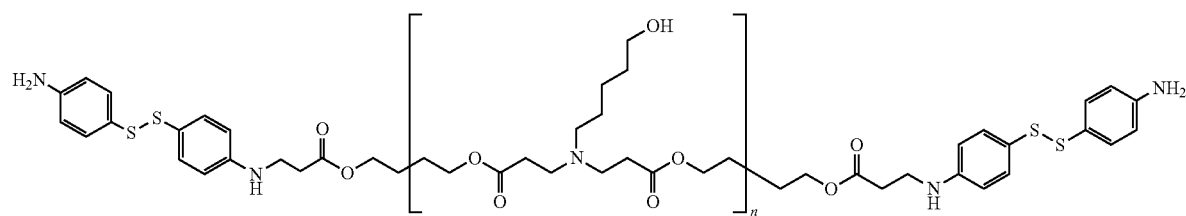

-continued
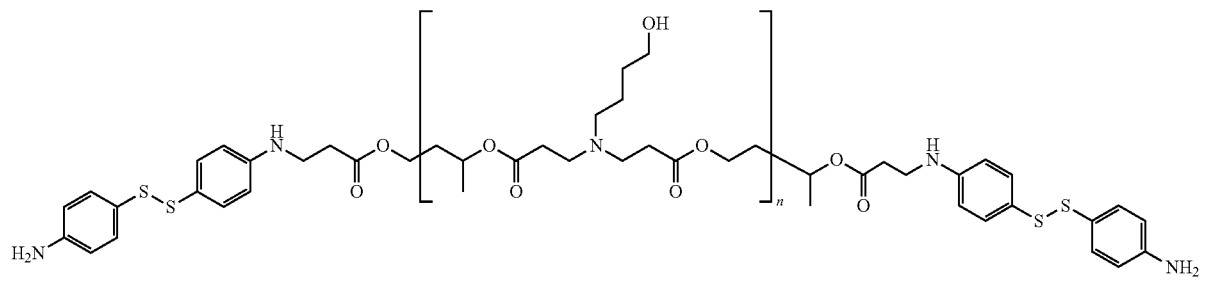
B3b-S4-E9
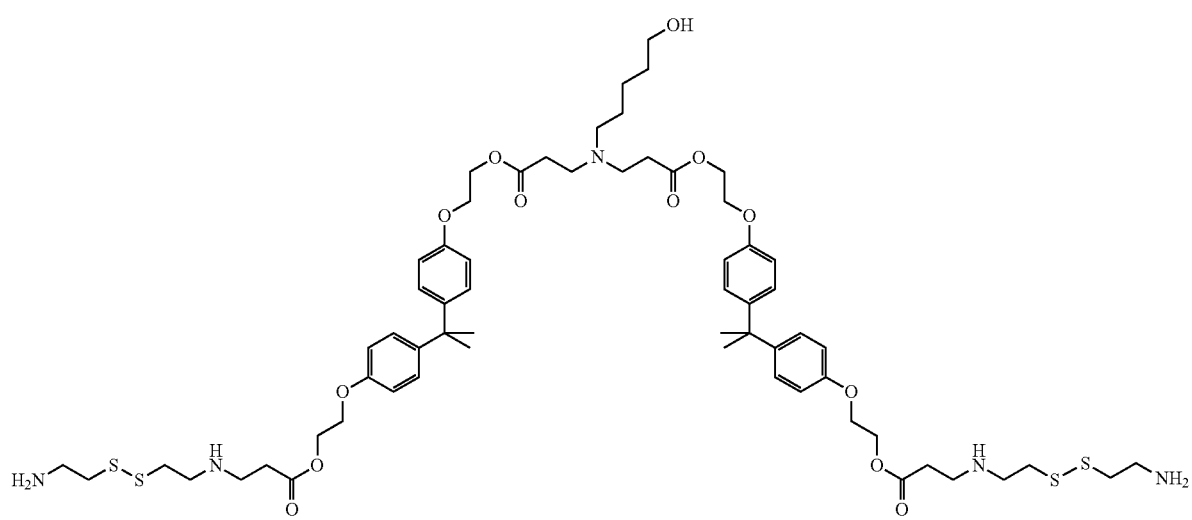
SL2-S5-E10
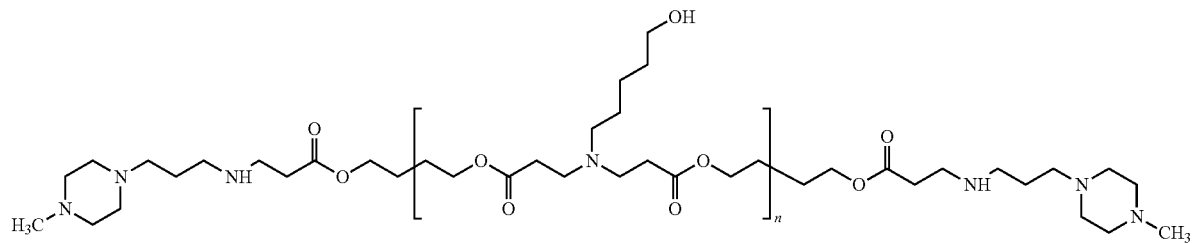
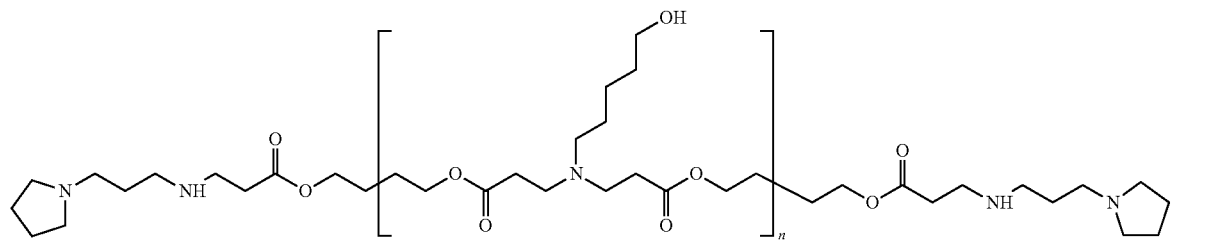
B3-S6-E7
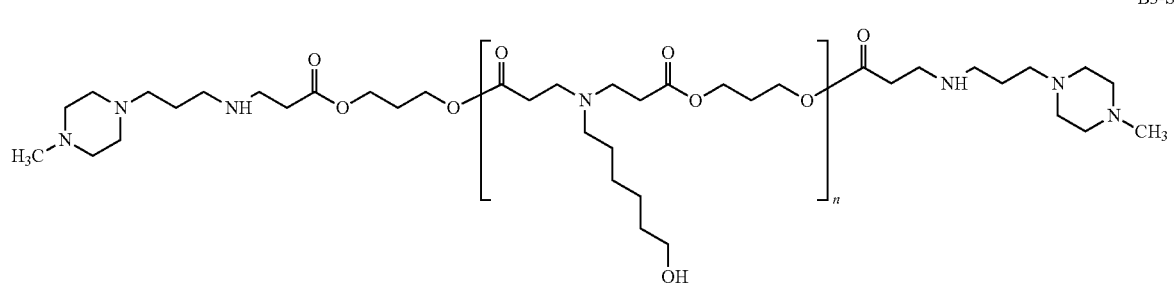

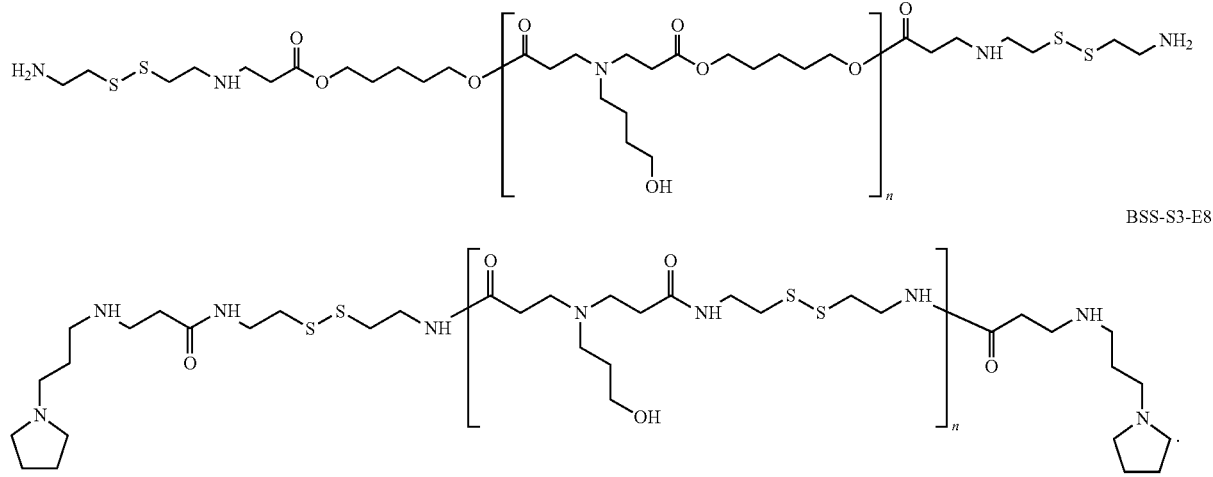

Further aspects of the presently disclosed subject matter include: (a) the R substituent groups that make up the presently disclosed polymers degrade via different biodegradation mechanisms within the same polymer. These biodegradation mechanisms can include hydrolytic, bioreducible, enzymatic, and/or other modes of degradation; (b) the ends of the polymer include a minority structure that differs from the majority structure that comprises most of the polymer backbone; (c) in several embodiments, the side chain molecules contain hydroxyl (OH)/alcohol groups.

In some embodiments: (a) the backbone is bioreducible and the end groups of the polymer degrade hydrolytically; (b) the backbone degrades hydrolytically and the end groups are bioreducible; and (c) hydrolytically degradable oligomers are cross-linked with a bioreducible cross-linker; (d) bioreducible oligomers form block copolymers with hydrolytically degradable oligomers; and (e) the end group/minority structure comprises an amino acid or chain of amino acids, whereas the backbone degrades hydrolytically and/or is bioreducible.

One way to synthesize the presently disclosed materials is by the conjugate addition of amine-containing molecules to acrylates or acrylamides. This reaction can be done neat or in a solvent, such as DMSO or THF. Reactions can take place at a temperature ranging from about room temperature up to about 90° C. and can have a duration from about a few hours to about a few weeks. The presently disclosed methods can be used to create linear or branched polymers. In some embodiments, the molecular weight (MW) has a range from about 1 kDa to about 5 kDa, in other embodiments, the MW has a range from about 5 kDa to about 10 kDa, in other embodiments the MW has a range from about 10 kDa to about 15 kDa, in other embodiments, the MW has a range from about 15 kDa to about 25 kDa, in other embodiments, the MW has a range from about 25 kDa to about 50 kDa, and in other embodiments, the MW has a range from about 50 kDa to about 100 kDa. In other embodiments, the polymer forms a network, gel, and/or scaffold of apparent molecular weight greater than 100 kDa.

II. APPLICATIONS OF MULTICOMPONENT DEGRADABLE CATIONIC POLYMERS

The presently disclosed subject matter provides the synthesis and characterization of a library of materials that are potentially useful for varied aspects of biomedical engineering. The presently disclosed polymers can be applied in any field where polymers have been found useful including, but not limited to, drug delivery and nucleic acid delivery. Accordingly, in some embodiments, the presently disclosed polymers provide for efficient intracellular delivery of therapeutic agents, such as nucleic acids, proteins, and the like, into cells. Thus, the presently disclosed polymers are well suited for the efficient delivery of DNA for non-viral gene delivery applications.

More particularly, the presently disclosed materials are useful for drug and gene delivery due, in part, to one or more of the following aspects: (a) an ability to bind and encapsulate cargos including, but not limited to, DNA, siRNA, peptides, and proteins; (b) an ability to facilitate uptake of the cargos into a range of cell types, with differential cell-type specificity. Being able to tune delivery to certain cell types based on small molecule changes to the ends of the polymers are one aspect of the presently disclosed subject matter; (c) an ability to promote endosomal escape to protect the cargos from degradation and enhance delivery to the cytoplasm or alternatively, an ability to direct delivery to the endosome or other compartments; (d) the materials are bioreducible, which enables triggered intracellular drug release of a given cargo to be tuned to promote optimal delivery to the target cell type of interest. Some of these polymers degrade only through reducible linkages. Other polymers have multiple modes of degradation and degrade unevenly. For example, certain linkages are broken when the material moves from an oxidative to a reducing environment, other linkages are broken due to the presence of water, and the rates of degradation can be further tuned by other molecules that act as catalysts; (e) the materials are not cytotoxic; and (f) the materials have a large potential for structural diversity.

Accordingly, in some embodiments, the presently disclosed biodegradable, cationic polymers can be used to deliver one or more therapeutic agents, biomolecules or small molecules to a cell, tissue, and/or organism either in vitro or in vivo. Representative therapeutic agents, biomolecules or small molecules include, but are not limited to, DNA, RNA (siRNA, miRNA, isRNA, agRNA, smRNA, and the like), nucleic acids, peptides, proteins, hydrophobic drugs, and small molecules.

Such embodiments can be used to treat various conditions or diseases including, but not limited to, cancer, including brain cancer (including Glioblastoma Multiforme), lung cancer, and other cancers; cardiovascular diseases; infectious diseases; ophthalmic diseases, including age-related macular degeneration. The presently disclosed polymers also can be used as a genetic vaccine or as artificial antigen presenting cells; as an adjuvant; as an immunosuppressant; as an immune system modulator; as agents for cell targeting; for enhancement of crops; enhancement of animals; and other therapeutic use in humans.

In some embodiments, the presently disclosed polymers are put together as a kit for the delivery of an agent, a nucleic acid, DNA, or RNA to a specific cell line or to any non-specified type of cell. In further embodiments, the presently disclosed polymers can be put together as a kit for the delivery of agents to specific cells to generate induced pluripotent stem cells. In some embodiments, the presently disclosed polymers can be put together as a kit for the delivery of agents to stem cells to control their growth, differentiation, and/or development.

The presently disclosed biomaterials (linear or branched oligomers, polymers, or cross-linked polymers) also can be useful for other applications, including, but not limited to, coatings for particles or devices via electrostatic or covalent interactions with the particles or surfaces. Such devices include, but are not limited to, nanoparticles, microparticles, stents, stent-like devices, and the like. Such coated devices also could be included in kits for screening or assay development.

Accordingly, in some embodiments, the presently disclosed polymers can be used to coat surfaces for biomedical applications or environmental applications, including, but not limited to, coating devices such as stents, stent-like devices, implants, or other biomedical or drug delivery devices. In some embodiments, multilayered coatings comprising 1-10 polymer layers; in some embodiments, 11-20 polymer layers; in some embodiments, 21-30 polymer layers; in some embodiments, 31-50 polymer layers; in some embodiments, 51-100 polymer layers; and in some embodiments, greater than 100 polymer layers.

In some embodiments, the presently disclosed polymers can be used as cosmetic products. In other embodiments, the presently disclosed polymers can be used as dental products In certain embodiments, the degradation products or the presently disclosed polymers are bioactive. In some embodiments, the degradation products are drugs and/or pro-drugs. In other embodiments, the degradation products facilitate organelle targeting. In yet other embodiments, the degradation products facilitate nuclear targeting.

In certain embodiments, nanoparticles formed through the presently disclosed procedures that encapsulate active agents (such as DNA, siRNA, peptide, and proteins) are themselves encapsulated into a larger microparticle or device. In some embodiments, this larger structure is degradable and in other embodiments it is not degradable and instead serves as a reservoir that can be refilled with the nanoparticles. These microparticles and/or devices can be constructed with any biomaterials and methods that one skilled in the art would be aware. In some embodiments they can be constructed with multi-component degradable cationic polymers as described herein. In other embodiments, they can be constructed by FDA approved biomaterials, including, but not limited to, poly(lactic-co-glycolic acid) (PLGA). In the case of PLGA and the double emulsion fabrication process as an example, the nanoparticles are part of the aqueous phase in the primary emulsion. In the final PLGA microparticles, the nanoparticles will remain in the aqueous phase and in the pores/pockets of the PLGA microparticles. As the microparticles degrade, the nanoparticles will be released, thereby allowing sustained release of the nanoparticles.

In certain embodiments, the nanoparticle targeting (through biomaterial selection, nanoparticle biophysical properties, and/or a targeting ligand) will be combined with transcriptional targeting. Transcriptional targeting includes designing a promoter so that the delivered nanoparticles carrying a nucleic acid cargo are only active in the cells or tissue types of interest. In one particular example applied to treating brain cancer, combinations of different genetic cargos and/or particles are co-delivered simultaneously to deliver nucleic acids that both: (1) induce apoptosis (genes for tumor necrosis factor-related apoptosis-inducing ligand (TRAIL), p53, and the like) and (2) cause differentiation of cancer stem cells (Bone morphogenetic protein 4 (BMP-4) DNA, Glycogen synthase kinase 3beta shRNA/siRNA, and the like). These nucleic acids are driven by brain cancer specific promoters, such as Nestin and Sox-2 for brain cancer stem cells and Glial fibrillary acid protein (GFAP) for glia.

In some embodiments, the presently disclosed subject matter also includes a method of using and storing the polymers and particles described herein whereby a cryoprotectant (including, but not limited to, a sugar) is added to the polymer and/or particle solution and it is lyophilized and stored as a powder. Such a powder is designed to remain stable and be reconstituted easily with aqueous buffer as one skilled in the art could utilize.

III. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formulae I-X are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

A named "R" or group will generally have the structure that is recognized in the art as corresponding to a group having that name, unless specified otherwise herein. For the purposes of illustration, certain representative "R" groups as set forth above are defined below.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom. Representative alkyl groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, and the like, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propyne, 3-hexyne, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, alkenyl, alkynyl, aryl, substituted aryl, aralkyl, hydroxyl, alkoxyl, aryloxyl, aralkyloxyl, carboxyl, acyl, halo, haloalkyl, nitro, alkoxycarbonyl, aryloxycarbonyl, aralkoxycarbonyl, acyloxyl, amino, alkylamino, dialkylamino, trialkylamino, acylamino, aroylamino, carbamoyl, cyano, alkylcarbamoyl, dialkylcarbamoyl, carboxyaldehyde, carboxyl, alkoxycarbonyl, carboxamide, arylthio, alkylthio, alkylene, thioalkoxyl, and mercapto.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The terms "heteroaryl" and "aromatic heterocycle" and "aromatic heterocyclic" are used interchangeably herein and refer to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole. The heteroaryl ring can be fused or otherwise attached to one or more heteroaryl rings, aromatic or non-aromatic hydrocarbon rings, or heterocycloalkyl rings. A structure represented generally by the formula:

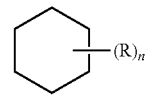

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

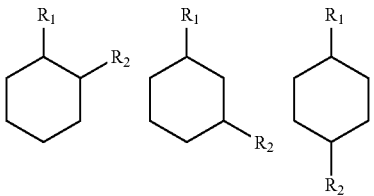

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

Further, as used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 μm). In such embodiments, the particle also can be referred to as a "microparticle. Thus, the term "microparticle" includes particles having at least one dimension in the range of about one micrometer (μm), i.e., $1 \times 10^{-6}$ meters, to about 1000 μm. The term "particle" as used herein is meant to include nanoparticles and microparticles.

It will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. In particular embodiments, the presently disclosed nanoparticles have a spherical shape.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

"Peptide" or "protein": A "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

A. Polymer Synthesis 1,4-butanediol diacrylate (Alfa Aesar), 5-amino-1-pentanol (Alfa Aesar), 1-(3-aminopropyl)-4-methylpiperazine (Lancaster), 1-(3-aminopropyl)pyrrolidine (Acros Organics), 4-aminophenyl disulfide (Sigma-Aldrich), dimethyl sulfoxide (Sigma-Aldrich), 25 kDa polyethylenimine (Sigma-Aldrich), and LIPOFECTAMINE 2000™ (Invitrogen) were used as received.

Polymers were synthesized using a two-step procedure that is described in FIG. 1. Acrylate-terminated poly(1,4-butanediol diacrylate-co-5-amino-1-pentanol) was first synthesized at two different acrylate monomer to amine monomer molar ratios, 1.05:1 and 1.2:1. For the 1.05:1 ratio, 3,532 mg of 1,4-butanediol diacrylate (17.8 mmol) was added to 1,754 mg of 5-amino-1-pentanol (17.0 mmol) and for the 1.2:1 ratio, 3,532 mg of 1,4-butanediol diacrylate (17.8 mmol) with 1,533 mg of 5-amino-1-pentanol (14.8 mmol). Reactions took place in DMSO (500 mg/mL) in glass vials in the dark under magnetic stirring for 48 hrs at 40° C.

As a second step, three amine-containing small molecules were individually conjugated to the ends of each polymer post-polymerization. Reactions were performed by mixing 321 mg of poly(1,4-butanediol diacrylate-co-5-amino-1-pentanol) in DMSO (500 mg/mL) with 800 µL of 0.25-M amine solution. Excess amine is used to fully end-modify the base polymer. Reactions were performed in 1.5 mL tubes in a multi-tube vortexer with constant agitation for 24 hours at room temperature. Polymers were stored at −20° C. with desiccant until use. Polymers were analyzed by gel permeation chromatography using a Waters Breeze System and 3 Styragel Columns (7.8×300 mm) in series: HR 1, HR 3, and HR 4. The eluent was 95% THF/5% DMSO/0.1 M piperidine and ran at 1 mL/min.

B. Cell Culture

COS-7 and IMR-90 cells (ATCC, Manassas, Va.) were grown following ATCC recommended protocols and reagents. COS-7s were grown in Dulbecco's Modified Eagle's Medium (DMEM, ATCC) supplemented with 10% fetal bovine serum (ATCC) and 100 units/mL of penicillin and streptomycin (Invitrogen). IMR-90s were grown in Eagle's Minimum Essential Medium (EMEM, ATCC) supplemented with 10% fetal bovine serum (ATCC) and 100 units/mL of penicillin and streptomycin. Cells were subcultured upon confluence and IMR-90s were used prior to passage eight.

C. Gene Delivery Assays

Cells were plated in white 96-well plates at 15,000 cells in 100 µL per well and allowed to adhere overnight. CMV-Luc DNA (Elim Biopharmaceuticals, Hayward, Calif.) was diluted in 25-mM sodium acetate (pH=5) to 0.06 mg/mL. Polymers at 100 mg/mL in DMSO were diluted in 25 mM sodium acetate buffer to concentrations that generate the varying polymer to DNA weight ratios (e.g., 20, 40, 60, and 100). One hundred microliters of diluted polymer solution was mixed vigorously with 100 µL of DNA solution in a 96-well plate using a multichannel pipette. After 10 minutes wait time, 20 µL of each formulation was added to the cells that contained 100 µL of complete media per well. Particles were incubated with the cells for four hours and then removed with a 12-channel aspirator wand. Warm, complete media was added to the cells (100 µL/well) and they were allowed to grow for two days at 37° C. and 5% $CO_2$.

Polyethylenimine/DNA particles were formed in a similar manner to the other polymers, except that they were formed at a w/w ratio of 1 (N/P~8) in 150-mM NaCl solution as has been previously described. See O. Boussif, et al., *Proc. Natl. Acad. Sci. USA* 92:7297-301 (1995); M. M. O. Sullivan, et al., *Gene Ther.* 10:1882-1890 (2003).

LIPOFECTAMINE 2000™ was used following the manufacturer instructions. Forty-eight hours post transfection, gene expression was measured using Bright-Glo luminescence assay kits (Promega), a Synergy 2 multilabel plate reader (Biotek), and a one second read time per well. Protein content per well was measured using the BCA protein assay kit (Pierce) and the Synergy 2 plate reader to measure absorbance at 562 nm.

D. Representative Embodiments

Base acrylate-terminated polymers were synthesized via the conjugate addition of 5-amino-1-pentanol to an excess of 1,4-butanediol diacrylate in a manner similar to that previously described, but at a lower temperature and for a longer reaction time while being dissolved in DMSO. See J. J. Green, et al., *Adv. Mater.* 19:2836-2842 (2007); G. T. Zugates, et al., *Mol. Ther.* 15:1306-1312 (2007).

Polymerizations were performed at molar ratios of 1.05:1 and 1.2:1 at 40° C. for 48 hrs. Subsequently, the polymers were end-modified by conjugate addition of 1-(3-aminopropyl)-4-methylpiperazine (Poly 1), 1-(3-aminopropyl)pyrrolidine (Poly 2), or 4-aminophenyl disulfide (Poly 3) to the base polymers at room temperature for 24 hrs (FIG. 1). Polymers were analyzed by gel permeation chromatography as shown in Table 1. For the 1.2:1 molar ratio, polymers had a Mw of approximately 6 kDa. At a 1.05:1 molar ratio, the molecular weight was higher, a Mw having a range from about 6.5 kDa to about 8.5 kDa. Gene delivery particles were formed in buffer through self-assembly between the cationic polymers and anionic DNA.

TABLE 1

| | Polymer Molecular Weight | | | |
|---|---|---|---|---|
| | Ratio | $M_n$ | $M_w$ | PDI |
| Poly 1 | 1.05:1 | 5415 | 7696 | 1.42 |
| | 1.2:1 | 4580 | 6124 | 1.34 |
| Poly 2 | 1.05:1 | 4249 | 6459 | 1.52 |
| | 1.2:1 | 3943 | 5714 | 1.45 |
| Poly 3 | 1.05:1 | 5680 | 8521 | 1.50 |
| | 1.2:1 | 3547 | 5448 | 1.54 |

At lower weight ratios (20 and 40 w/w), polymeric particles formed with polymers synthesized at a ratio of 1.05:1 were generally more efficient for gene delivery than the same polymers formed at 1.2:1. This result is likely due to the higher MW of these polymers. In some cases, these changes were dramatic. For example, for Poly 1 at 20 w/w, the 1.05:1 ratio is more than 10-fold as effective as the 1.2:1 ratio with COS-7 cells and 400-fold more effective for IMR-90s (FIG. 2).

Interestingly, the difference in MW between these two polymers is only approximately 1.5 kDa. At higher weight ratios (e.g., 60 w/w and 100 w/w), however, this trend is not observed and the effectiveness of both polymer synthesis conditions is comparable. The one exception to this trend is Poly 2, which has comparable delivery between the two synthesis ratios at 60 w/w and 100 w/w in COS-7 cells, but in IMR-90 cells, only the 1.05:1 ratio polymer is effective at any weight ratio tested. Thus, these results indicate that small changes to MW could tune delivery properties to alter cell-type specificity.

Certain end-modifying groups also appeared to show cell-type specificity. For example, Poly 3 at 60 w/w or 100 w/w has very high gene delivery to the COS-7 cancerous fibroblasts, but very poor delivery to the IMR-90 human primary fibroblasts. In comparison to LIPOFECTAMINE 2000™, Poly 3 (1.2:1 ratio and 60 w/w) exhibits twice the gene expression in COS-7 cells, but over 200-fold less expression in IMR-90s. For transfection of IMR-90s, Poly 1 or Poly 2 at a polymerization ratio of 1.05:1 and polymer to DNA weight ratio of 100 were the most effective. These conditions enabled transfection of human primary fibroblasts in serum-containing media at 8- to 10-fold the levels of LIPOFECTAMINE 2000™. LIPOFECTAMINE 2000™ is a leading commercially available lipid-based transfection reagent and the presently disclosed polymers can achieve comparable or higher delivery to both cancerous and primary cell types. Compared to 25 kDa branched polyethylenimine, a leading off-the-shelf gene delivery polymer, the presently disclosed polymers are up to 2 to 3 orders of magnitude more effective. In all cases, cells remained viable and comparable to untreated controls as determined by visual inspection and relative levels of protein content per well through the BCA assay.

Small molecule amine containing end-groups were chosen to increase DNA binding affinity compared to acrylate terminated polymers and to potentially improve endosomal release of the particles (Poly 1 and Poly 2) or bioreducible release of the DNA (Poly 3). Because these small structural modifications also lead to a significant change in cell-type specificity, the end-group also might play an important role in directing particle uptake.

Example 2

A. Polymer Synthesis

Monomers (BSS, S3, S4, S5, E1, E2, E3, E4, E5, E6, E7, E8, E9, E10, E11, E12) and controls (LIPOFECTAMINE 2000™ and FUGENE HD®) were used as received from vendor. Polymers were synthesized using a two-step procedure. Acrylamide-terminated base polymer (N,N'-bis(acrylyl)cystamine-co-4-amino-1-butanol etc.) was first synthesized at monomer 1:1 molar ratios in a 9:1 methanol:water mixture. Reactions took place in glass vials in the dark under nitrogen atmosphere with magnetic stirring for 5 days at 60° C. After 5 days, 10% additional BSS was added to leave all polymers acrylamide terminated. After 2 more days, reactions were removed from the oven and precipitated in ether. As a second step, amine-containing small molecules (E1-E12) were individually conjugated to the ends of each polymer. Excess amine is used to fully end-modify the base polymer. Reactions were performed in 1.5 mL tubes in a multi-tube vortexer with constant agitation for 48 hours at room temperature. Polymers were stored at −20° C. with desiccant until use.

Other polymers were synthesized using a two-step procedure. Polymers such as acrylate-terminated poly(1,4-butanediol diacrylate-co-5-amino-1-pentanol) were first synthesized at up to 7 different acrylate monomer to amine monomer molar ratios from 1.4:1 to 1:1.4 (FIG. 9). Reactions took place in DMSO (500 mg/mL) in glass vials in the dark under magnetic stirring for 48 hrs at 40° C. or neat at 90° C. for 24 hours. Polymers were analyzed by gel permeation chromatography using a Waters Breeze System and 3 Styragel Columns (7.8×300 mm) in series: HR 1, HR 3, and HR 4. The eluent was 95% THF/5% DMSO/0.1 M piperidine and ran at 1 mL/min.

B. Cell Culture

COS-7 cells (ATCC, Manassas, Va.) were grown following ATCC recommended protocols and reagents. COS-7s were grown in Dulbecco's Modified Eagle's Medium (DMEM, ATCC) supplemented with 10% fetal bovine serum (ATCC) and 100 units/mL of penicillin and streptomycin (Invitrogen).

C. Gene Delivery Assays

Cells were plated in white 96-well plates at 15,000 cells in 100 µL per well and allowed to adhere overnight. CMV-Luc DNA (Elim Biopharmaceuticals, Hayward, Calif.) was diluted in 25-mM sodium acetate (pH=5) to 0.06 mg/mL. Polymers at 100 mg/mL in DMSO were diluted in 25 mM sodium acetate buffer to concentrations that generate the varying polymer to DNA weight ratios (e.g., 20, 40, 60, and 100). One hundred microliters of diluted polymer solution was mixed vigorously with 100 µL of DNA solution in a 96-well plate using a multichannel pipette. After 10 minutes wait time, 20 µL of each formulation was added to the cells that contained 100 µL of complete media per well. Particles were incubated with the cells for four hours and then removed with a 12-channel aspirator wand. Warm, complete media was added to the cells (100 µL/well) and they were allowed to grow for two days at 37° C. and 5% $CO_2$.

LIPOFECTAMINE 2000™ (Invitrogen) and FUGENE HD® (Roche) were used following the manufacturer instructions. Forty-eight hours post transfection, gene expression was measured using Bright-Glo luminescence assay kits (Promega), a Synergy 2 multilabel plate reader (Biotek), and a one second read time per well. Protein content per well was measured using the BCA protein assay kit (Pierce) and the Synergy 2 plate reader to measure absorbance at 562 nm.

D. Binding Assay

Yo-Pro-1 is a carbocyanine nucleic acid stain that competitively binds to DNA against the polymer. By measuring the fluorescence of Yo-Pro-1 in DNA with exposure to different concentrations of polymer, we generated a quenching curve of Yo-Pro-1 vs. polymer concentration. Binding affinity was determined by fitting to the McGhee and von Hippel model of non-specific binding of large ligands to a one-dimensional homogenous lattice using MATLAB.

E. Representative Embodiments

Gel permeation chromatography data (FIG. 10) highlights how the polymers created are bioreducible. They had higher molecular weight initially, but when each bioreducible polymer (5 mg/mL) was run with or without a reducing agent, dithiothreitol (DTT), at 5 mM concentration, their molecular weight dramatically changed to the constituent monomers. The broader peak at earlier time points for each of the polymers disappears with addition of the reducing agent and there is a concomitant increase in small molecular weight monomers at later time points of the run.

Competitive binding assays (FIG. 11) show how addition of glutathione, a reducing agent, to a representative bioreducible polymer significantly reduces the binding affinity of the polymer to DNA. This property enables the nanoparticles to release their bioactive agent or cargo more efficiently inside cells. When the polymer has weak DNA binding affinity, Yo-Pro-1 binds DNA strongly and emits a strong fluorescent signal. However, when the polymer binds DNA with high affinity, it displaces the Yo-Pro-1 dye and prevents this fluorescent signal. The same polymer, BSS-S4-E8, is shown before and after incubation with glutathione at 0 hrs and at 24 hrs. The 24 hr glutathione incubated curve shows that polymer-DNA binding is dramatically reduced compared to both the 0 hr glutathione sample and the 24 hr glutathione-free sample. Inside a cell, such a polymer would have strong DNA binding in extracellular oxidizing environments, but low DNA binding and efficient DNA release in the cytoplasm of the cell that is a reducing environment.

Transfection efficacy of select bioreducible polymers are shown in FIG. 12. All polymers were transfected at 600 ng/well DNA. The best BSS based polymers (designated BSS-S4-E4 and BSS-S4-E1) obtained signals that were 215× and 50× higher than untreated wells, respectively. Additionally, end-capping generic base polymer B4-S5 with two reducible end groups made two new effective polymers, which combine hydrolytic degradation with disulfide reduction of the end groups. These polymers have comparable efficacy to FUGENE HD® and LIPOFECTAMINE 2000™, and leading degradable polymers. The best bioreducible polymer formulations demonstrate significantly reduced transfection in the presence of 5 mM glutathione (all controls unaffected);

By both GPC data and a competitive binding assay, the presently disclosed subject matter demonstrates that these polymers allow for triggered release in the presence of a reducing environment. In these conditions, the presently disclosed polymers have a triggered decreased in polymer molecular weight and reduced nanoparticle binding. Combined with the relative reducing environment of the cytoplasm, these results demonstrate that the bioreducible function could facilitate nanoparticle unpacking in the cytoplasm. The COS-7 transfection data show that small changes to the structure of the base polymer and to the end-groups drastically alter the ability of the polymer to transfect cells. The presently disclosed polymers have comparable transfection efficacy to leading commercially available transfection agents such as LIPOFECTAMINE 2000™ and FUGENE HD®. In addition, the effectiveness of B4-S5-E9 and E10 shows that adding bioreducible functionality to a hydrolytically degradable polymer via change in polymer terminal group is a useful method for improving cargo release.

Example 3

A. Materials and Polymer Synthesis

Monomers were purchased from commercial vendors including the following: 1,4-butanediol diacrylate (B4) (Alfa Aesar), 5-amino-1-pentanol (S5) (Alfa Aesar), 2-methylpentane-1,5-diamine (E4), 1-(3-aminopropyl)-4-methylpiperazine (E7), 1-(3-aminopropyl)pyrrolidine (E8), 4-aminophenyl disulfide (E9), cystamine (E10), dimethyl sulfoxide (Sigma-Aldrich), FUGENE HD® (Roche), and LIPOFECTAMINE 2000™ (Invitrogen) and were used as received. Other materials included Dulbecco's modified Eagle's medium and Dulbecco's modified Eagle's medium/F12 (Invitrogen), FBS, and 1% v/v penicillin/streptomycin (Sigma P0781). A two-step polymer synthesis scheme was used. Acrylate-terminated poly(1,4-butanediol diacrylate-co-5-amino-1-pentanol) base polymer (B4S5) was first synthesized at different acrylate monomer to amine monomer molar ratios, including 1:1.1, 1:1.05, 1:1, 1.05:1, 1.1:1 and 1.2:1. As an example, to prepare the base polymer with 1.05:1 ratio, 3532 mg of 1,4-butanediol diacrylate (17.8 mmol) was added to 1754 mg of 5-amino-1-pentanol (17.0 mmol). The monomers were reacted in the dark by magnetic stirring in glass scintillation vials in dimethyl sulfoxide (DMSO) at 500 mg/mL. The base polymers at 1:1.05 and 1.05:1 monomer ratios were synthesized by stirring at 40° C. for 48 hours. The base polymers at the other monomer ratios were synthesized by stirring at 90° C. for 24 hours. In the second step, the diacrylate terminated base polymers were endcapped with amine-containing small molecules E4, E7, E8, E9 and E10. End-capping reactions were performed in 1.5 mL tubes by adding 320 μL of 0.5 M amine solution in DMSO to 480 μL of the base polymer dissolved in DMSO. Polymers were stored at −20° C. with desiccant until use. Polymers were analyzed by gel permeation chromatography using a Waters Breeze System and 3 Styragel Columns (7.8×300 mm) in series: HR 1, HR 3, and HR 4. The eluent was 95% THF/5% DMSO/0.1 M piperidine and ran at 1 mL/min.

B. Cell Culture

Epithelial cells were cultured at 37° C. and 5% $CO_2$ in Dulbecco's modified Eagle's medium/F12 with 10% FBS and 1% v/v penicillin/streptomycin (Sigma P0781). After polymer transfection cells were washed twice with 1 mL DMEM and finally incubated in fresh EPH4 media for 48 hours post transfection. COS-7 and IMR-90 cells (ATCC, Manassas, Va.) were grown following ATCC recommended protocols and reagents. COS-7s were grown in Dulbecco's Modified Eagle's Medium (DMEM, ATCC) supplemented with 10% fetal bovine serum (ATCC) and 100 units/mL of penicillin and streptomycin (Invitrogen). IMR-90s were grown in Eagle's Minimum Essential Medium (EMEM, ATCC) supplemented with 10% fetal bovine serum (ATCC) and 100 units/mL of penicillin and streptomycin. Cells were subcultured upon confluence and IMR-90s were used prior to passage eight. Similarly, Glioblastoma multiforme (GBM) brain cancer cells, retinal neurons, and other cell lines were grown by standard procedures as utilized by one skilled in the art.

C. Gene Delivery Assays

For high throughput transfection screening, Eph4 cells were plated at two different cell densities, 150,000 cells/mL and 170,000 cells/mL in 96-well plates in 100 μL media and allowed to adhere overnight. CMV Luc DNA (Elim Biopharmaceuticals, Hayward, Calif.) was diluted in 25 mM sodium acetate (pH=5) to varying concentrations of 0.06 mg/mL, 0.12 mg/mL and 0.18 mg/mL to respectively vary the DNA dose per well, 0.6 μg/well, 1.2 μg/well and 1.8 μg/well. Polymer stock solutions at 100 mg/mL in DMSO were diluted in the sodium acetate buffer (25 mM, pH=5) to concentrations required to generate two different polymer to DNA weight ratios (wt/wt), 60 wt/wt and 100 wt/wt. 100 μL of diluted polymer solution was mixed vigorously with 100 μL of DNA solution in a 96-well plate using a multichannel pipette. The particles were allowed to self-assemble for 10 minutes, following which 20 μL of each formulation was added to the cells containing 100 μL of complete media per well in quadruplicate. The cells were incubated with the particles for four hours and then the particles were aspirated with a 12-channel aspirator wand. 100 μL/well of complete media was added to the cells and they were allowed to grow for two days at 37° C. and 5% $CO_2$. FUGENE HD® and LIPOFECTAMINE 2000™ were used according to the manufacturer instructions. Two days post transfection the CMV-Luc gene expression was measured using Bright-Glo luminescence assay kit (Promega) and a Synergy 2 multi-label plate reader (Biotek) with a one second read time per well. The BCA protein assay kit (Pierce) was used to determine the protein content per well in the Synergy 2 plate reader by measuring the absorbance at 562 nm. The effect of polymer structure, DNA dose, polymer to DNA wt/wt ratio and cell density on transfection efficiency was studied.

For the scale-up transfections for flow-cytometry studies, cells were plated at 150,000 cells/mL in 24-well plates with 500 μL media per well and were allowed to adhere overnight. The eGFP DNA (Elim Biopharmaceuticals, Hayward, Calif.) was diluted in 25 mM sodium acetate (pH=5) to a concentration of 0.12 mg/mL to get a DNA dose per well of 6 μg/well. Polymer stock solutions at 100 mg/mL in DMSO were diluted in the sodium acetate buffer (25 mM, pH=5) to concentration required to generate polymer to DNA weight ratio of 60 wt/wt. 110 μL of diluted polymer solution was mixed vigorously with 110 μL of DNA solution in an eppendorf tube. After allowing the particle to self-assemble for 10 minutes, 100 μL of each formulation was added to the cells in each well of the 24-well plate in duplicates. Again after an incubation period of 4 hours, the particles were aspirated and 500 μL of fresh media was added to each well. The cells were allowed to grow in the incubator at for two days at 37° C. and 5% $CO_2$. FUGENE HD® was prepared by following the manufacturer 24-well plate protocol.

After two days, the cells were harvested from the 24-well plate for fluorescence expression quantification using flow cytometry analysis. The media was aspirated from each well, followed by a wash with 500 μL PBS (Gibco) and then 200 μL of 0.05% trypsin/EDTA was added to each well. The cells were trypsinized for approximately 5 to 10 minutes at 37° C. 500 μL of complete media with serum was added to each well to neutralize the trypsin. The cell suspension was transferred to a 1.5 mL eppendorf tube and was centrifuged in a microcentrifuge at 1000 rpm for 5 minutes. After aspirating the supernatant, the cell pellet was washed twice with PBS and eventually resuspended in 500 μL of buffer containing PBS, 1:20 fetal bovine serum and 1:200 parts propidium iodide (PI). The tube containing the final cell suspension was kept on ice prior to flow cytometry analysis using the FACScan flow cytometry scanner (Flow Cytometry Facility, Johns Hopkins School of Medicine). The flow cytometry results were analysed using the FlowJo software (Tree Star, Inc.). The untreated control sample (with no GFP, no PI) was analyzed to set the gating for the intact cell population in the forward vs. side scatter dot plot and the propidium iodide only control (no GFP) was used to gate the live cell and dead cell population. The results were quantified as % GFP positive cells/live cells.

Mammary epithelial cultures were prepared as previously described (A. J. Ewald, et al., "Collective Epithelial Migration and Cell Rearrangements Drive Mammary Branching Morphogenesis," Dev Cell. vol. 14(4) pp. 570-581, April 2008). Briefly, glands were minced and tissue was shaken for 30 min at 37° C. in a 50 mL collagenase/trypsin solution in DMEM/F12 (GIBCO-BRL), 0.1 g trypsin (GIBCO-BRL), 0.1 g collagenase (Sigma C5138), 5 mL fetal calf serum, 25 μL of 10 μg/mL insulin, and 50 μL of 50 μg/mL gentamicin. The collagenase solution was centrifuged at 1500 rpm for 10 min, dispersed through 10 mL DMEM/F12, centrifuged at 1500 rpm for 10 min, and then resuspended in 4 mL DMEM/F12+40 μL DNase (2U/μL) (Sigma). The DNase solution was shaken by hand for 2-5 min, then centrifuged at 1500 rpm for 10 min. Organoids were separated from single cells through four differential centrifugations (pulse to 1500 rpm in 10 mL DMEM/F12).

Similar to the Eph4 transfection protocol, 110 μL of 0.12 mg/mL eGFP DNA was mixed with 110 μL of diluted polymer in an eppendorf tube to obtain a 60 wt/wt ratio of polymer to DNA. After a 10 min waiting time for particle self-assembly, 100 μL of formulation was added to each organoid well in duplicates per condition. The cells were incubated with the particles for 4 hours, and then the mammary epithelial fragments were collected into eppendorf tubes coated with 2.5% BSA in PBS solution and isolated by centrifugation at 90 g for 2 min. Each condition was washed twice with 1 mL DMEM/F12 media followed by centrifugation step to remove residue polymer. Each condition was resuspended in 100 μL Matrigel [~200 organoids/100 mL] in a non-treated 24-well plate (Falcon #351147) on 37° C. heat block for 5 min. and followed by 20 min. in a 5% CO$_2$ incubator. Finally, 500 μL branching media (DMEM/F12, 1% v/v insulin, transferrin, selenium [Sigma] and 1% v/v penicillin/streptomycin [100× stock]) with 2.5 nM FGF2 [Sigma F0291]) was added to each well. GBM and other cell lines followed the same protocols for transfection and FACS analysis.

D. Representative Embodiments

This example highlights how small structural changes to constituent monomers and process changes during synthesis can tune properties of the polymers, the nanoparticles, they form, and their delivery efficacy. In particular, specific tuning of these multi-component cationic polymers enable changes to cell-type specificity, something that is non-obvious, but very important to the uses of these polymers. Three dimensional cultures, including mammary organoids culture are difficult and transfection efficacy levels are typically low. Yet, the multicomponent polymers described here are able to deliver genes non-virally to these three-dimensional constructs. For example, FIG. 3 demonstrates that genes encoding green fluorescent protein are delivered to primary cells in three-dimensional organoids by the presently disclosed polymer designated B4-S5-E9 (also referred to herein as Poly 3). FIG. 4 shows that the disulfide end-group, designated herein as E9, can make biphasic polymer designated B4-S5-E9 more effective than other polymers such as those designated as B4-S5-E7 or B4-S5-E8, which have difference end groups designated E7 and E8 herein, at transfecting primary cells in three-dimensional organoids. In two-dimensional epithelial culture (EPH4 cells), gene delivery of the presently disclosed polymers designated B4-S5-E10 is also high to as compared to commercially available reagent FUGENE HD® (shown in FIG. 6, % GFP positive as determined by FACS). With the same molecular structure, gene delivery efficacy can also depend strongly on the synthesis conditions used (monomer ratio and temperature).

These multicomponent gene delivery polymers are useful for other cell types as well and choice of structural elements tunes efficacy between cell types. FIG. 5 shows gene delivery with a series of presently disclosed polymers comparable to FUGENE HD® in (top) H146 and (bottom) H446 lung cancer cells. FIG. 7 demonstrates the ability of a presently disclosed polymer designated B4-S5-E10 (60 w/w) for transfecting Glioblastoma Multiforme (GBM) cells as measured by flow cytometry and Green Fluorescent Protein (GFP) expression. FIG. 8 shows this same polymeric nanoparticle formulation with GBM cells by microscopy. Gene delivery and cell viability of polymer B4-S4-E7 with IMR90 cells is shown in FIG. 21. This figure shows transfection of IMR90s 48 hrs post addition of nanoparticles. GFP expression is shown on the left panels and cell viability on the right. These human primary cells are transfected highly while remaining fully viable. FIG. 22 shows transfection of a retinal neuron with a representative polymer B4-S4-E8. GFP is expressed brightly and morphological structures are good. A broader view of the drug and gene delivery capability of the polymer library described herein is shown in FIG. 23. This figure shows transfection of a luciferase gene across many representative polymers in COS-7 cells. Each polymer is able to form nanoparticles that deliver genes to COS-7 cells. The polymers were synthesized at 90° C. unless indicated as 40° C. Tuning the polymer backbone monomer, side group monomer, terminal group monomer, monomer ratio during synthesis, synthesis temperature, and nanoparticle formulation ratio (w/w) each independently varies overall gene delivery efficacy. FIG. 24 shows transfection of a luciferase gene across many representative polymers in IMR-90 cells. Each polymer is able to form nanoparticles that deliver genes to primary human fibroblasts, IMR-90s. The polymers were synthesized at 90° C. unless indicated as 40° C. Tuning the polymer backbone monomer, side group monomer, terminal group monomer, monomer ratio during synthesis, synthesis temperature, and nanoparticle formulation ratio (w/w) each independently varies overall gene delivery efficacy. Through comparative evaluation of these many experiments and figures, it is clear that these multicomponent polymers described can be designed to either show cell-type specificity towards specific cells or be highly effective for the transfer of nucleic acids intracellularly across a wide range of cells. This example demonstrates the many uses of these materials in vitro as reagents and promisingly suggests their therapeutic utility when used in vivo as one skilled in the art could do through either intravenous, intradermal, subcutaneous, intramuscular, and/or intraperitoneal injection, implantation, or other means.

Importantly, this example also shows that properties of the polymers can be tuned to increase delivery efficacy. Due to the different steps in gene delivery, changes to multicomponent gene delivery can improve efficacy the following ways: improving protection/encapsulation of a cargo, improving cellular uptake and cell-specific uptake, control of endosomal buffering and endosomal escape, independent control of DNA release, triggered release of an active agent, modification of particle surface charge, increased diffusion through the cytoplasm, active transport through the cytoplasm, increased nuclear import within the cell, and increased transcription and translation of delivered nucleic acids. Changes to cell-specific delivery have been described in this example above and changes to DNA release and triggered release have been described herein in Example 2. To improve protection/encapsulation of a cargo, the molecular weight can be tuned through three different mechanisms: changing the monomer ratio, changing the reaction temperature and time, adding a cross-linking agent. A range of molecular weights formed with base polymer B4-S5 is shown in FIG. 9 as an example. How these molecular weights can be further tuned by selection of terminal group and/or cross-linker is shown in FIG. 17. Varying these conditions as well as formulation conditions (polymer to DNA mass ratio, mixing rate, buffer composition, and incubation time) can tune nanoparticle size as well. Nanoparticle size is shown in FIG. 18 where the nanoparticles formed by self-assembly of B4-S5-based polymers including B4-S5-E9 and B4-S5-E10 with enhanced green fluorescent protein (EGFP) DNA. The particles were sized using two techniques: Dynamic Light Scattering (intensity-weighted mean) and Nanoparticle Tracking Analysis (NTA). NTA was used to determine both the direct number-weighted mean and the mode. Nanoparticles shown in this example are nanoparticles in the useful range for intracellular delivery sized from approximately 50 nm to 250 nm. By tuning the formulation conditions (polymer to DNA mass ratio, mixing rate, buffer composition, and incubation time), these particles also can be made smaller or larger in size up to micron sized particles. The size of the particles can tune the transport of the particles though the cell. Alteration of the polymer terminal group can also change the nanoparticle's charge, affecting uptake and transport through the cell. Through changes to the multicomponent structure of the polymers herein, the compartment of delivery, endosomal buffering, and escape from the endosome to the cytoplasm can also be tuned. FIG. 13 shows the titration of representative presently disclosed polymers (e.g., B4-S5-E9, B4-S5-E10, BSS-S5-E7, etc.) showing that they can buffer the pH of the endosomal compartment (pH~6) as is needed to protect drug delivery agents and facilitate endosomal rupture through the proton sponge effect. This characteristic is representative of other presently disclosed polymers, which have a range of buffering capacities. Buffering the endosome (or lack of buffering) is important to facilitate endosomal escape (or endosome targeting) and also to protect the agent being delivered. Finally, multicomponent cationic polymers, like those described herein, can have degradation products that themselves aid in nuclear import and transcription and translation of delivered nucleic acids.

Example 4

A. Materials and Polymer Synthesis

Monomers were purchased from commercial vendors. A two-step polymer synthesis scheme was used. Acrylate-terminated polymer was first synthesized at different acrylate monomer to amine monomer molar ratios, including 1:1.1, 1:1.05, 1:1, 1.05:1, 1.1:1 and 1.2:1. The monomers were reacted in the dark by magnetic stirring in glass scintillation vials in dimethyl sulfoxide (DMSO) at 500 mg/mL. The base polymers at 1:1.05 and 1.05:1 monomer ratios were synthesized by stirring at 40° C. for 48 hours. The base polymers at the other monomer ratios were synthesized by stirring at 90° C. for 24 hours. In the second step, the diacrylate terminated base polymers were endcapped with amine-containing small molecules E1 and E8. Endcapping reactions were performed in 1.5 mL tubes by adding 320 µL of 0.5 M amine solution in DMSO to 480 µL of the base polymer dissolved in DMSO. Polymers were stored at −20° C. with desiccant until use. Polymers were analyzed by gel permeation chromatography using a Waters Breeze System and 3 Styragel Columns (7.8×300 mm) in series: HR 1, HR 3, and HR 4. The eluent was 95% THF/5% DMSO/0.1 M piperidine and ran at 1 mL/min. Particle size was measured by dynamic light scattering on a Malvern Zetasizer Nano ZS (volume averaged size) or by Nanoparticle Tracking Analysis on a Nanosight LM10 (number averaged size). Materials for microparticle formulation include PLGA: 502H and PLGA 503H (Boehringer Ingelheim Chemicals) or MW=55,000 65:35 (Sigma), Dichloromethane (ACS reagent grade, Sigma), Trifluoroethanol (ACS reagent grade, Sigma), Bovine serum albumin (BSA) (Sigma A9056), Docusate sodium (Sigma D1685), 5% poly(vinyl alcohol) (Polysciences), and Phosphate Buffered Saline (PBS) (Invitrogen).

B. Representative Embodiments

If a hydrophilic peptide/protein is to be encapsulated, a hydrophilic polymer is chosen as the multicomponent material. If a hydrophobic peptide/protein is to be encapsulated than a hydrophobic polymer is chosen. Backbone, side chain, and terminal group can be modified to increase the hydrophobic or hydrophilic character of the polymer as has been described. The peptide/protein to be encapsulated is first dissolved in a suitable solvent such as DMSO or PBS. Then, it is combined with the polymer in sodium acetate (NaAc). This solution is then diluted with either: sodium acetate, OptiMem, DMEM, PBS, or water depending on particle size desired. The solution in vortexed to mix and then left to incubate for 5-15 min for particle assembly to take place. A third component that is amphipathic or that is multivalent (like DNA) was sometimes added to facilitate particle formation and to form tertiary particles.

FIG. 19 shows particle sizing data of nanoparticles formed by polymer B6-S4-E8 and a representative hydrophilic/negatively charged synthetic peptide (11-mer that includes 5 glutamic acid residues). Peak of blue curves shows particle sizes of ~100 nm for the particles when formulated at a 5:1 polymer to peptide mass ratio. Relative particle concentration for alternative formulations are also shown (Dark blue is a 1:1 ratio, Green is a 10:1 ratio). Particles self assemble at these mass ratios by vortexing in 25 mM NaAc buffer (pH=5) or in a more diluted buffer ranging up to pH=7. Size is by number as measured by Nanoparticle Tracking Analysis. FIG. 20 shows particle sizing data of nanoparticles formed by polymer BL1-S4-E1 and a representative hydrophobic peptide (SPWSPCST-SCGLGVSTRI). Peak of number distribution of nanoparticles is 74 nm for a polymer to peptide mass ratio of 1:1. Size is by number as measured by Nanoparticle Tracking Analysis. FIG. 25 shows polymer/peptide particle size depends on polymer structure, formulation conditions including buffer, and peptide that is being encapsulated. All sizing was conducted by dynamic light scattering and volume-averaged sizes are reported. All formulations were at 10 weight polymer to 1 weight peptide. "C" refers to peptide NGRKACLNPASPIVKKIIEKMLNS and "P" refers to peptide LRRFSTMPFMFCNINNVCNF. Thus a range of peptide structures and sizes can be incorporated by multicomponent polymers as described herein. By tuning polymer structure and formulation conditions, particle size can be tuned from ~10 nm to ~100 nm and to ~1000 nm sizes. Each of these biodegradable particle formulations can be added to cells for intracellular and/or extracellular delivery of the encapsulated peptide or similarly injected into animals or patients.

The nanoparticles formed through these procedures that encapsulate active agents (such as DNA, siRNA, peptide, and proteins) can themselves be encapsulated into a larger microparticle or device. This larger structure can be degradable and can also be not degradable and instead serves as a reservoir that can be refilled with the nanoparticles. Any biomaterial can be used for this larger structure. In the case of PLGA as an example, one method of encapsulation is the double emulsion technique described as following: Aqueous Phase (Prepare sterile): 250 µL PBS, 2.25 mg BSA, 250 µg peptide nanoparticles; Organic Phase: 5 mL Dichloromethane, 200 mg PLGA, Homogenizer Phase: 1% PVA in 50 mL water; Final PVA Solution: 0.5% PVA in 100 mL water. To form the Double Emulsion, the first step is forming a primary emulsion with a sonicator (the nanoparticles are in the aqueous phase of this emulsion), the second step is immediately forming a secondary emulsion with a homogenizer, and the third step is adding the homogenized solution to a 0.5% PVA solution under magnetic stirring. The solvent is left to evaporate in a chemical hood and then the particles are collected following cycles of centrifuging and washing with water. The final particles are lyophilized for 2 days and stored as a powder at −20 C with desiccant. As the microparticles degrade, the nanoparticles will be released allowing sustained release of the nanoparticles. In other applications, the peptide or protein can be directly coated onto the particle rather than encapsulated within it or may be encapsulated by cross-linked polymers to form a gel or scaffold. In other applications, the nanoparticle and/or microparticles formed can be further modified by coating with the polyelectrolyte polymers described herein.

Example 5

A. Materials and Polymer Synthesis

Monomers were purchased from commercial vendors. A two-step polymer synthesis scheme was used. Acrylate-terminated polymer was first synthesized at different acrylate monomer to amine monomer molar ratios, including 1:1.1, 1:1.05, 1:1, 1.05:1, 1.1:1 and 1.2:1. The monomers were reacted in the dark by magnetic stirring in glass scintillation vials in dimethyl sulfoxide (DMSO) at 500 mg/mL. The base polymers at 1:1.05 and 1.05:1 monomer ratios were synthesized by stirring at 40° C. for 48 hours. The base polymers at the other monomer ratios were synthesized by stirring at 90° C. for 24 hours. In the second step, the diacrylate terminated base polymers were endcapped with amine-containing small molecules E1 and E8. Endcapping reactions were performed in 1.5 mL tubes by adding 320 µL of 0.5 M amine solution in DMSO to 480 µL of the base polymer dissolved in DMSO. Polymers were stored at −20° C. with desiccant until use. Polymers were analyzed by gel permeation chromatography using a Waters Breeze System and 3 Styragel Columns (7.8×300 mm) in series: HR 1, HR 3, and HR 4. The eluent was 95% THF/5% DMSO/0.1 M piperidine and ran at 1 mL/min. Particle size was measured by dynamic light scattering on a Malvern Zetasizer Nano ZS (volume averaged size) or by Nanoparticle Tracking Analysis on a Nanosight LM10 (number averaged size).

B. Representative Embodiments

These multicomponent cationic polymers can be used for the delivery of nucleic acids such as RNA in addition to their role as delivery agents for DNA. FIG. 14 shows polymer/siRNA particle size (nm) as a function of formulation conditions (weight ratio polymer to RNA) for a representative presently disclosed polymer designated B5-S3-E9 (1.2:1 ratio for B5-S3). The formulations of the particles can be tuned to vary biophysical properties of the particle and their release. FIG. 15 shows the particle size/biophysical characterization of polymer/siRNA nanoparticles formed by a presently disclosed polymer designated BL2-S5-E10, 1.2:1. Mean particle size 20 w/w polymer/siRNA=100 nm. The lower panels show RNA encapsulation by the presently disclosed polymers and the resulting particle size distribution. Size depends on polymer type and formulation conditions. These particles can be used for intracellular or extracellular delivery by simply adding them to cells or by injecting them in animals or patients. As one example FIG. 16 shows direct delivery of siRNA to brain cancer cells using polymeric nanoparticles comprising a presently disclosed polymer designated B5-S3-E9. Brain cancer cells containing FITC-labeled siRNA molecules are shown as bright regions on this image. FIG. 7 demonstrates the ability of a presently disclosed polymer designated B4-S5-E10 (60 w/w) for transfecting Glioblastoma Multiforme (GBM) cells as measured by flow cytometry and Green Fluorescent Protein (GFP) expression and FIG. 8 shows a presently disclosed polymer (B4-S5-E10 (60 w/w)) and GBM cells by microscopy. Direct delivery of DNA/indirect delivery of RNA shows that many of these cells actively transcribe and translate this DNA to generate the GFP expression. The delivered plasmid could encode various shRNA molecules that are active within the cell instead of or in addition to GFP. This is an indirect method of RNA delivery in addition to the direct method as demonstrated with siRNA. In delivering RNA instead of DNA, important design considerations are: different polymer structures, different formulation condition including a lower polymer to nucleic acid weight ratio, and in some cases the addition of a third component that has multivalent characteristics.

In some applications, the particles described above can be combined with nanoparticle targeting (through biomaterial selection, nanoparticle biophysical properties, and/or a targeting ligand) and transcriptional targeting. Transcriptional targeting includes designing a promoter so that the delivered nanoparticles carrying a nucleic acid cargo are only active in the cells or tissue types of interest. In one example to brain cancer: Combinations of different genetic cargos and/or particles are co-delivered simultaneously to deliver nucleic acids that both 1) induce apoptosis (genes for tumor necrosis factor-related apoptosis-inducing ligand (TRAIL), p53, etc) and 2) cause differentiation of cancer stem cells (Bone morphogenetic protein 4 (BMP-4) DNA, Glycogen synthase kinase 3beta shRNA/siRNA, etc.). These nucleic acids are driven by brain cancer specific promoters such as Nestin and Sox-2 for brain cancer stem cells and Glial fibrillary acid protein (GFAP) for glia.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

T. G. Park, J. H. Jeong, and S. W. Kim, "Current status of polymeric gene delivery systems," *Advanced Drug Delivery Reviews*, vol. 58, pp. 467-486, mL 7 2006.

D. W. Pack, A S. Hoffman, S. Pun, and P. S. Stayton, "Design and development of polymers for gene delivery," *Nature Reviews Drug Discovery*, vol. 4, pp. 581-593, mL 2005.

M. C. Pedroso de Lima, S. Simoes, P. Pires, H. Faneca, and N. Duzgunes, "Cationic lipid-DNA complexes in gene delivery: from biophysics to biological applications," *Advanced Drug Delivery Reviews*, vol. 47, pp. 277-94, Apr. 25, 2001.

O. Boussif, F. Lezoualc'h, M. A Zanta, M. D. Mergny, D. Schennan, B. Demeneix, and J. P. Behr, "A versatile vector for gene and oligonucleotide transfer into cells in culture and in vivo: polyethylenimine," *Proc Natl Acad Sci USA*, vol. 92, pp. 7297-301, Aug. 1, 1995.

N. D. Sonawane, F. C. Szoka, and A S. Verkrnan, "Chloride accumulation and swelling in endosomes enhances DNA transfer by polyamine-DNA polyplexes," *Journal of Biological Chemistry*, vol. 278, pp. 44826-44831, Nov. 7, 2003.

A. Akinc, M. Thomas, A. M. Klibanov, and R. Langer, "Exploring polyethylenimine-mediated DNA transfection and the proton sponge hypothesis," *Journal of Gene Medicine*, vol. 7, pp. 657663, May 2005.

D. Putnam, C. A Gentry, D. W. Pack, and R. Langer, "Polymer-based gene delivery with low cytotoxicity by a unique balance of side-chain tennini," *Proc Natl Acad Sci USA*, vol. 98, pp. 1200-5, Jan. 30, 2001.

S. M. Moghimi, P. Symonds, J. C. Murray, A C. Hunter, G. Debska, and A Szewczyk, "A two-stage poly(ethylenimine)-mediated cytotoxicity: implications for gene transfer/therapy," *Mol Ther*, vol. 11, pp. 990-5, June 2005.

J. J. Green, D. G. Anderson, and R. Langer, "A combinatorial polymer library yields insights into the field of non-viral gene delivery," *Accounts of Chemical Research*, vol. 41, pp. 749-759, 2007.

D. M. Lynn and R. Langer, "Degradable poly(beta-amino esters): Synthesis, characterization, and self-assembly with plasmid DNA," *J Am Chem Soc*, vol. 122, pp. 10761-10768, 2000.

D. G. Anderson, A. Akinc, N. Hossain, and R. Langer, "Structure/property studies of polymeric gene delivery using a library of poly (beta-amino esters)," *Molecular Therapy*, vol. 11, pp. 426-34, March 2005.

A. Akinc, D. M. Lynn, D. G. Anderson, and R. Langer, "Parallel synthesis and biophysical characterization of a degradable polymer library for gene delivery," *Journal of the American Chemical Society*, vol. 125, pp. 5316-23, May 7, 2003.

J. J. Green, J. Shi, E. Chiu, E. S. Leshchiner, R. Langer, and D. G. Anderson, "Biodegradable polymeric vectors for gene delivery to human endothelial cells," *Bioconjugate Chemistry*, vol. 17, pp. 1162-1169, 2006.

A Akinc, D. G. Anderson, D. M. Lynn, and R. Langer, "Synthesis of poly(beta-amino ester)s optimized for highly effective gene delivery," *Bioconjugate Chemistry*, vol. 14, pp. 979-988, SEPOCT 2003.

J. J. Green, G. T. Zugates, N. C. Tedford, Y. Huang, L. G. Griffith, D. A Lauffenburger, J. A Sawicki, R. Langer, and D. G. Anderson, "Combinatorial modification of degradable polymers enables transfection of human cells comparable to adenovirus," *Advanced Materials*, vol. 19, pp. 2836-2842, 2007.

G. T. Zugates, W. Peng, A Zumbuehl, S. Jhunjhunwala, Y. H. Huang, R. Langer, J. A Sawicki, and D. G. Anderson, "Rapid Optimization of Gene Delivery by Parallel End-modification of Poly(beta-amino ester)s," *Mol Ther*, vol. 15, pp. 1306-1312, 2007.

M. A Gosselin, W. J. Guo, and R. J. Lee, "Efficient gene transfer using reversibly cross-linked low molecular weight polyethylenimine," *Bioconjugate Chemistry*, vol. 12, pp. 989-994, November-December 2001.

M. L. Forrest, J. T. Koerber, and D. W. Pack, "A degradable polyethylenimine derivative with low toxicity for highly efficient gene delivery," *Bioconjug Chem*, vol. 14, pp. 934-40, September-October 2003.

L. V. Christensen, C. W. Chang, W. J. Kim, S. W. Kim, Z. Zhong, C. Lin, J. F. Engbersen, and J. Feijen, "Reducible poly(amido ethylenimine)s designed for triggered intracellular gene delivery," *Bioconjugate Chemistry*, vol. 17, pp. 1233-40, September-October 2006.

C. Lin, C. J. Blaauboer, M. M. Timoneda, M. C. Lok, M. van Steenbergen, W. E. Hennink, Z. Zhong, J. Feijen, and J. F. Engbersen, "Bioreducible poly(amido amine)s with oligoamine side chains: synthesis, characterization, and structural effects on gene delivery," *Journal of Controlled Release*, vol. 126, pp. 166-74, Mar. 3, 2008.

J. Yu, M. A Vodyanik, K. Smuga-Otto, J. Antosiewicz-Bourget, J. L. Frane, S. Tian, J. Nie, G. A Jonsdottir, V. Ruotti, R. Stewart, Slukvin, II, and J. A Thomson, "Induced pluripotent stem cell lines derived from human somatic cells," *Science*, vol. 318, pp. 1917-20, Dec. 21, 2007.

M. M. O. Sullivan, J. J. Green, and T. M. Przybycien, "Development of a novel gene delivery scaffold utilizing colloidal gold-polyethylenimine conjugates for DNA condensation," *Gene Therapy*, vol. 10, pp. 1882-1890, October 2003.

A. J. Ewald, A. Brenot, M. Duong, B. S. Chan, and Z. Werb, "Collective Epithelial Migration and Cell Rearrangements Drive Mammary Branching Morphogenesis" *Dev Cell.* vol. 14(4) pp. 570-581, April 2008.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I), wherein the compound of formula (I) has the following structure:

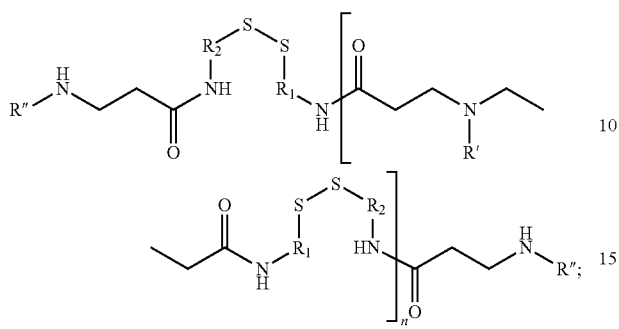

wherein:
n is an integer from 1 to 10,000;
each $R_1$ and $R_2$ are each independently $C_1$-$C_{30}$ alkylene chains;
each R' independently comprises a functional group selected from the group consisting of —OH, —$NH_2$ and —SH; and
each R" independently comprises a non-reducible amino group independent from R' or —C—R' and wherein R' is selected from the group consisting of:

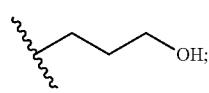 (S3)

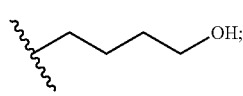 (S4)

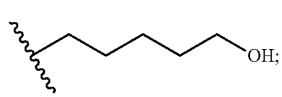 (S5)

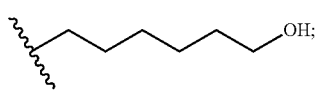 (S6)

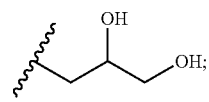 (S7)

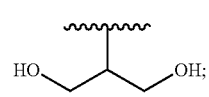 (S8)

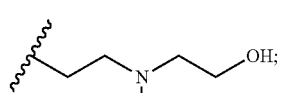 (S9)

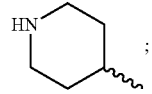 (S10)

-continued

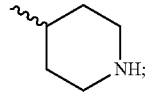 (S10)

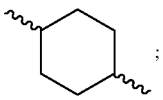 (S10)

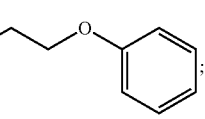 (S11)

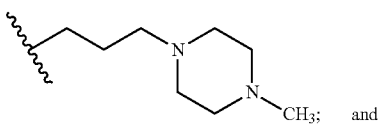 (S12)

and (S13)

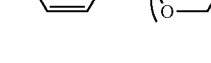

2. The compound of claim 1, wherein n is an integer selected from the group consisting of: an integer from 1 to 1,000; an integer from 1 to 100; an integer from 1 to 30; an integer from 5 to 20; an integer from 10 to 15; and an integer from 1 to 10.

3. The compound of claim 1, wherein the non-reducible R" group is selected from the group consisting of:

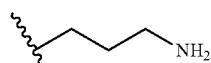 

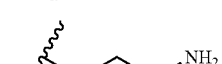 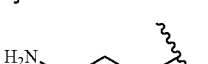

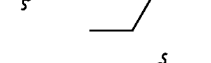 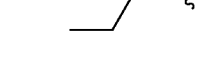

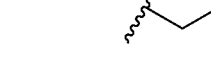 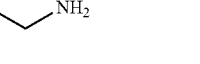

 

 

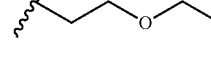 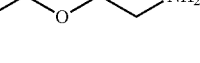

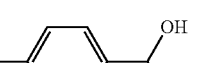 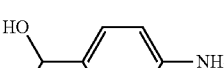

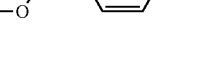

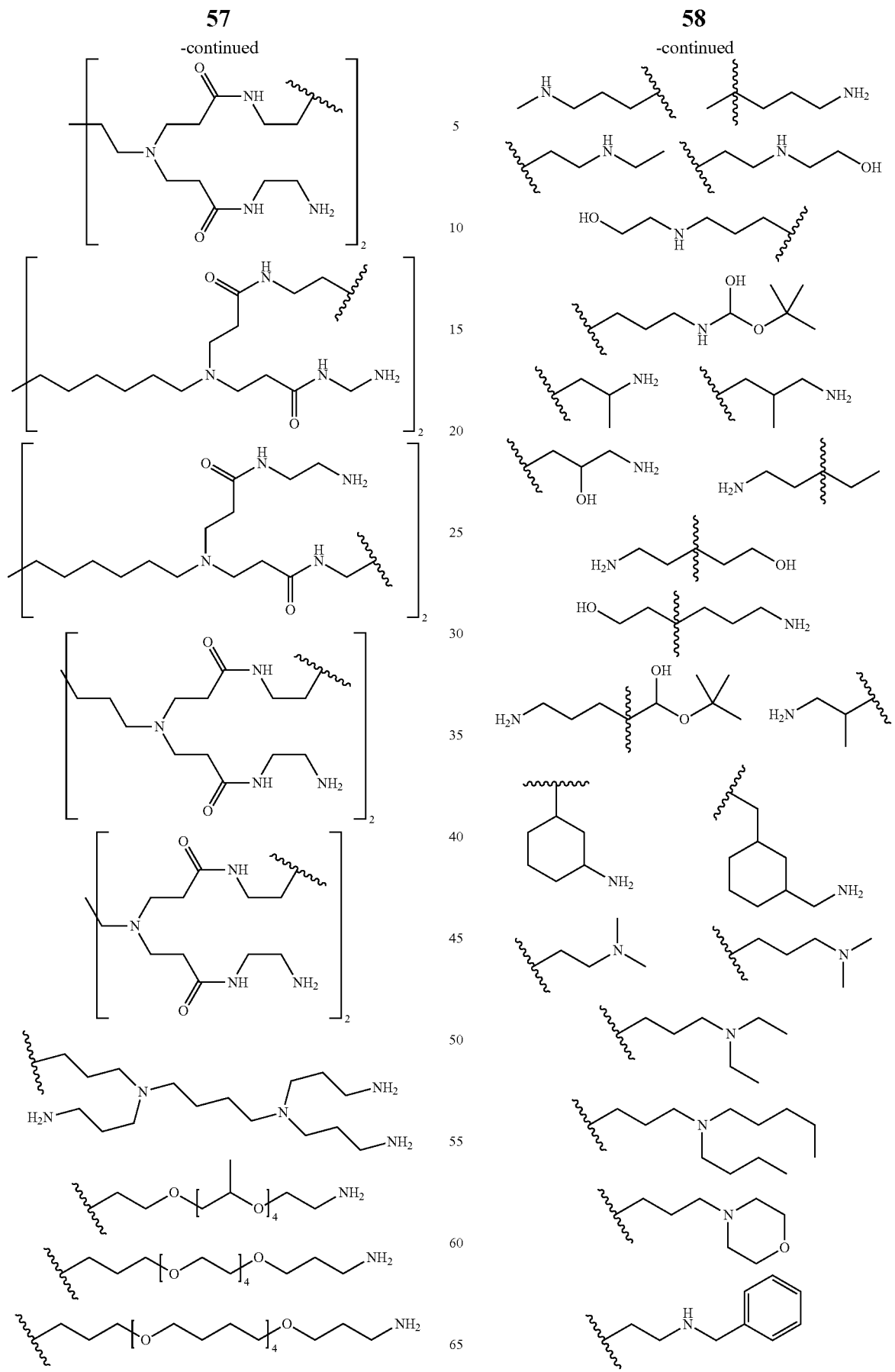

59
-continued
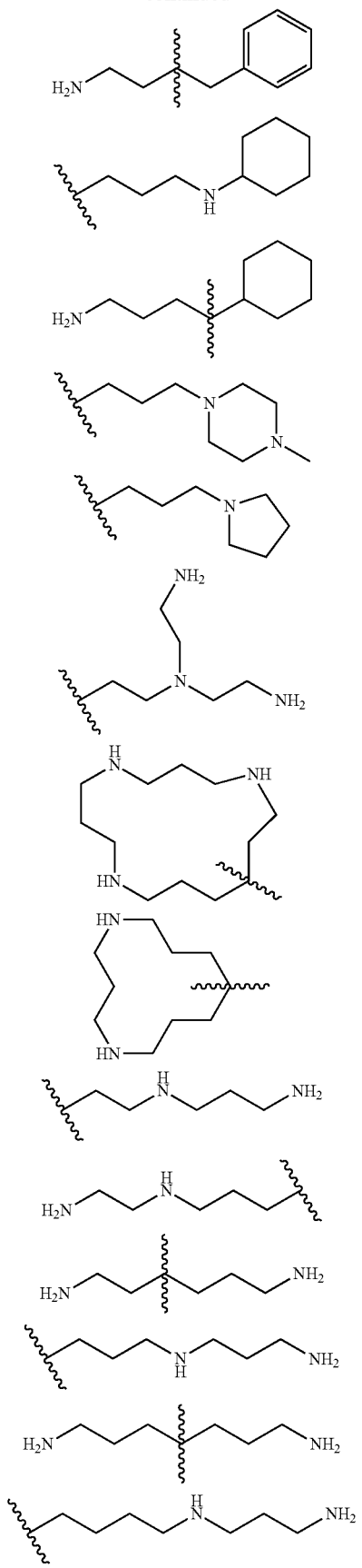
60
-continued
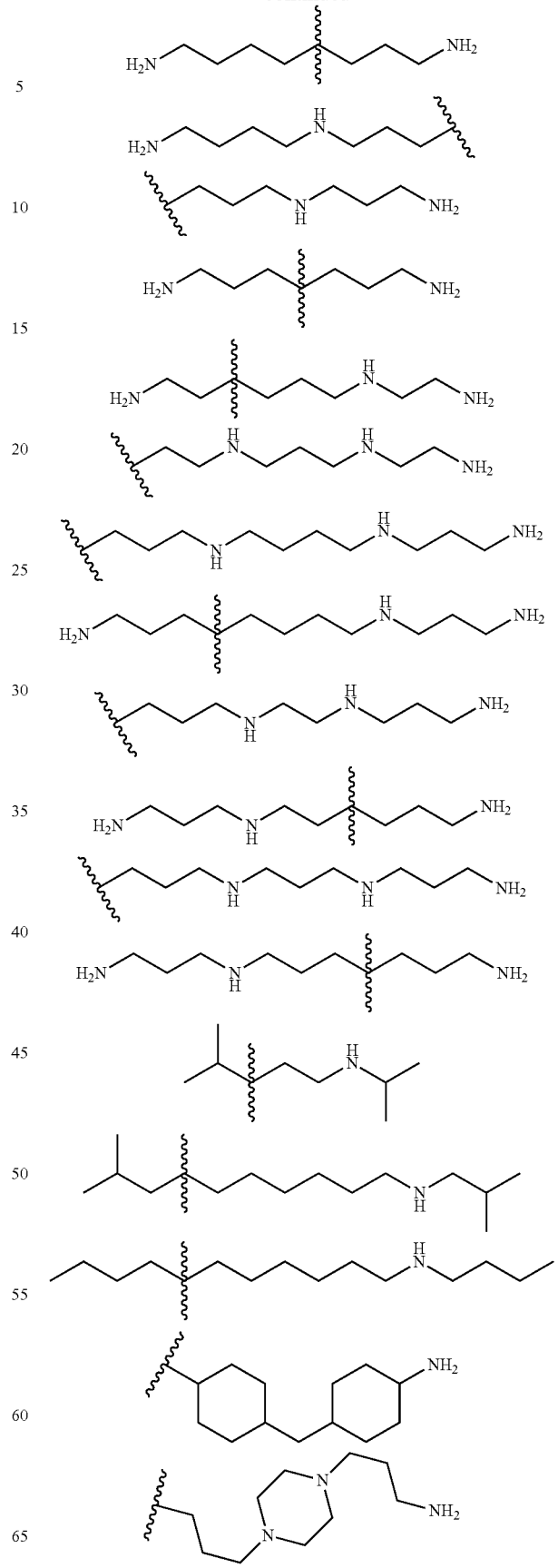

61
-continued

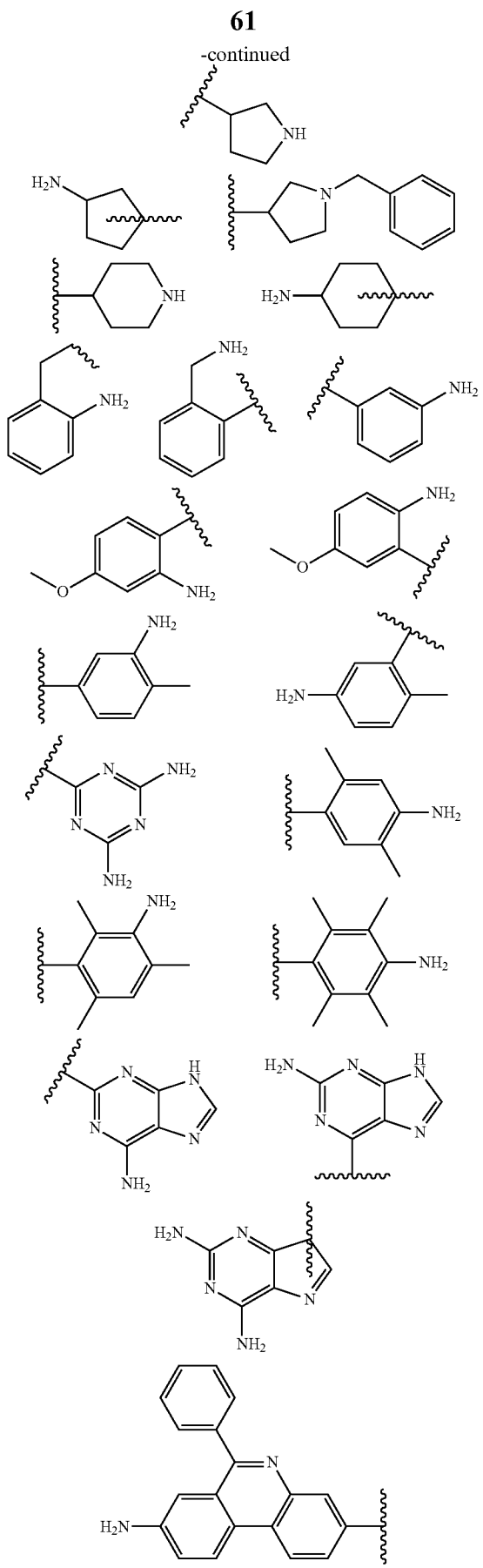

62
-continued

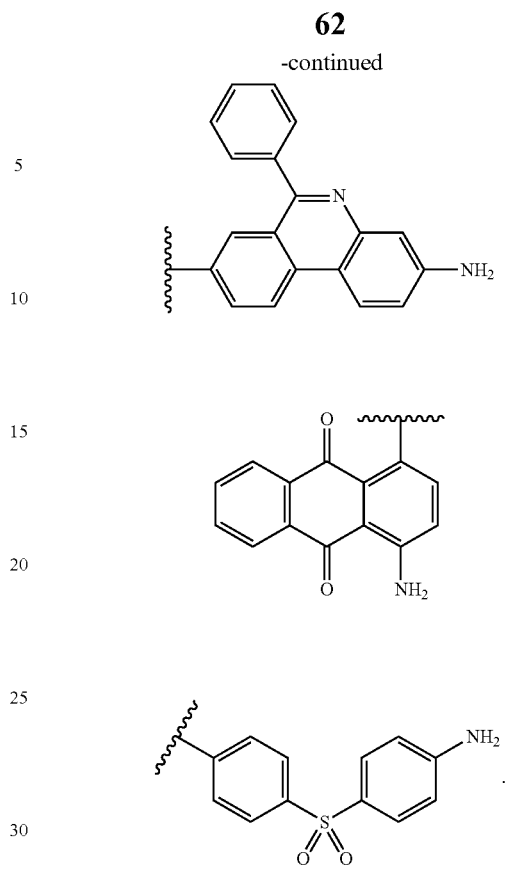

4. A pharmaceutical composition comprising a compound of claim 1.

5. The pharmaceutical composition of claim 4 further comprising a therapeutic agent.

6. The pharmaceutical composition of claim 5, wherein the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug.

7. The pharmaceutical composition of claim 4 further comprising a nanoparticle or microparticle comprising a compound of formula (I).

8. A pharmaceutical composition comprising a compound of claim 3.

9. The pharmaceutical composition of claim 8 further comprising a therapeutic agent.

10. The pharmaceutical composition of claim 9, wherein the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug.

11. The pharmaceutical composition of claim 8 further comprising a nanoparticle or microparticle comprising a compound of formula (I).

12. A compound of formula (I), wherein the compound of formula (I) has the following structure:

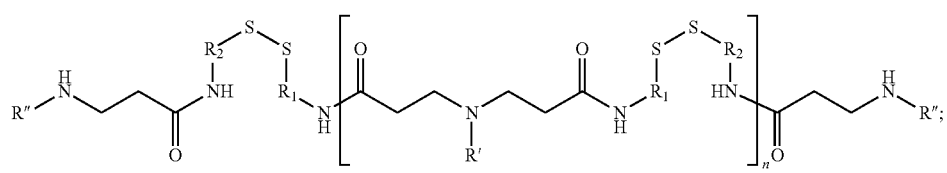

wherein:
  n is an integer from 1 to 10,000;
  each $R_1$ and $R_2$ are each independently $C_1$-$C_{30}$ alkylene chains;
  each R' independently comprises a functional group selected from the group consisting of —OH, —$NH_2$ and —SH; and
  each R" independently comprises a non-reducible amino group independent from R' or —C—R', wherein the non-reducible R" group is selected from the group consisting of:

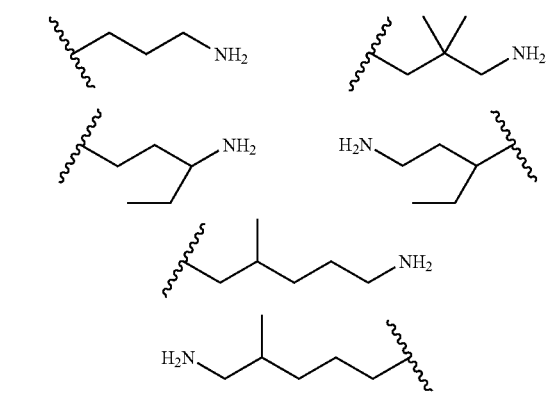

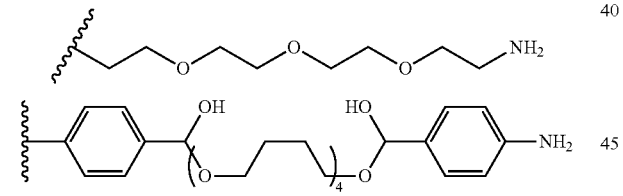

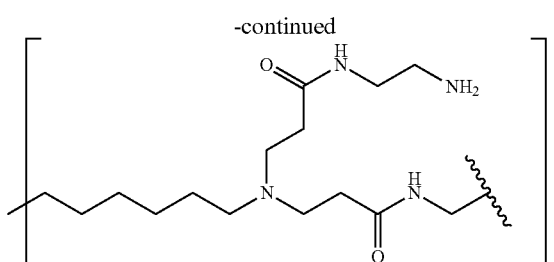

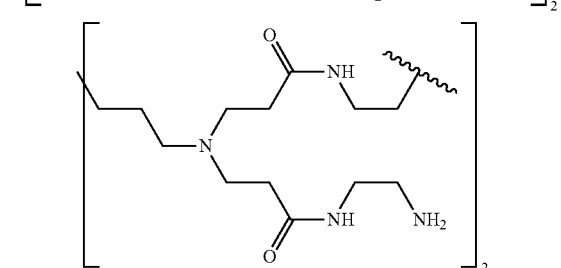

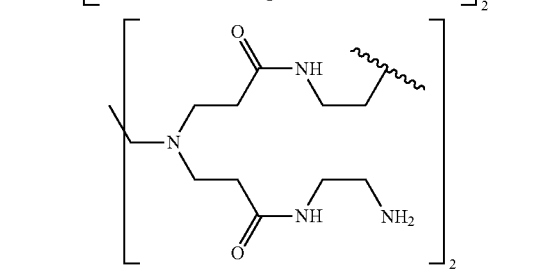

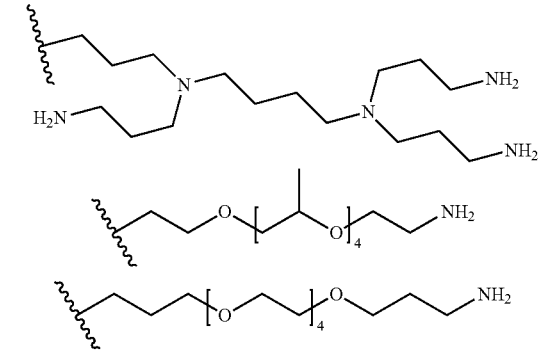

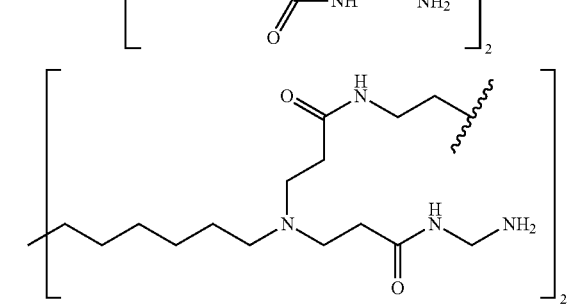

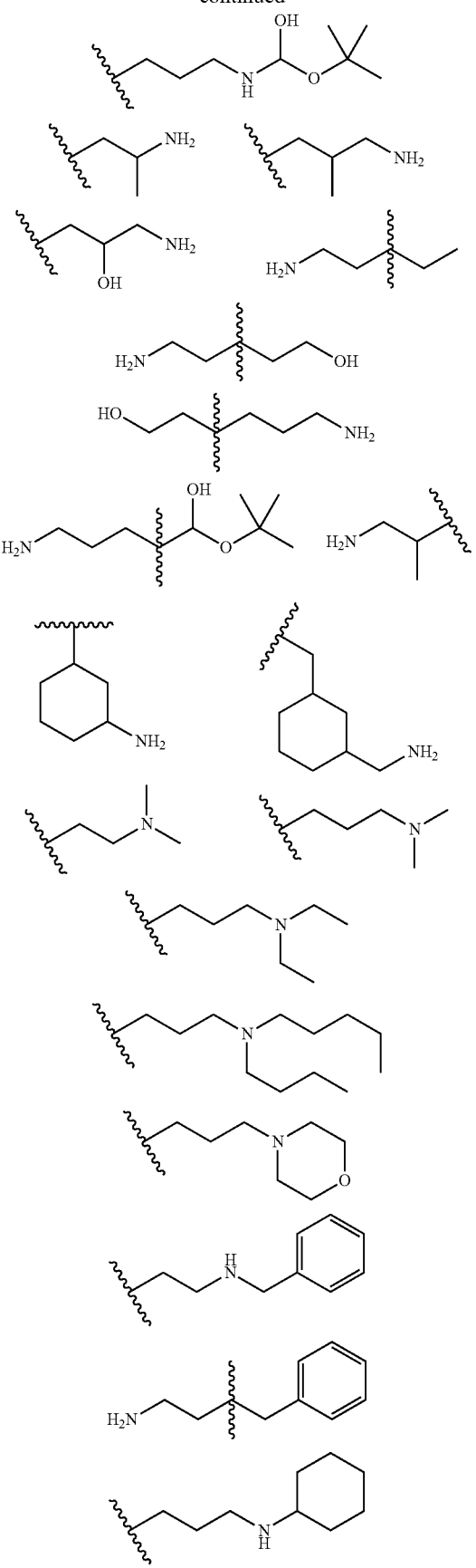
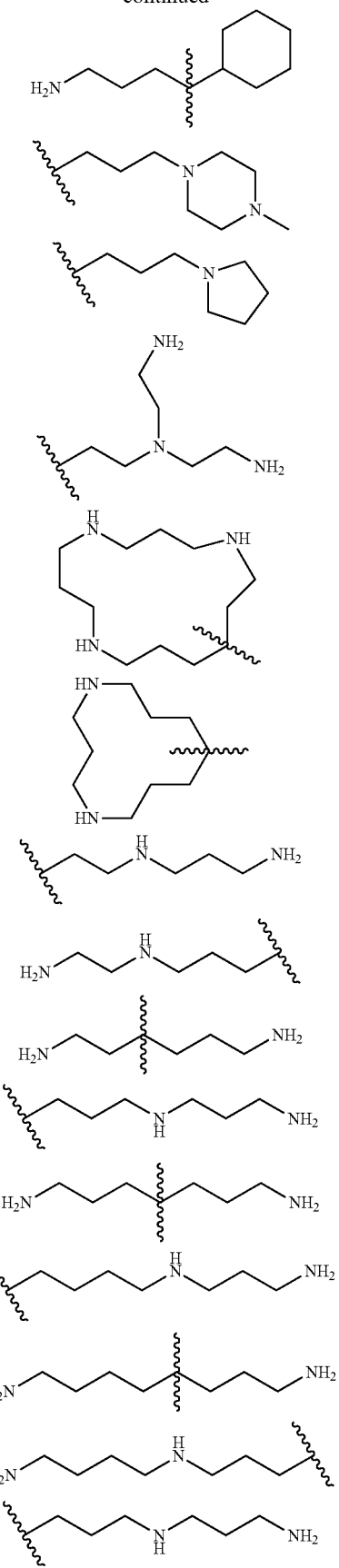

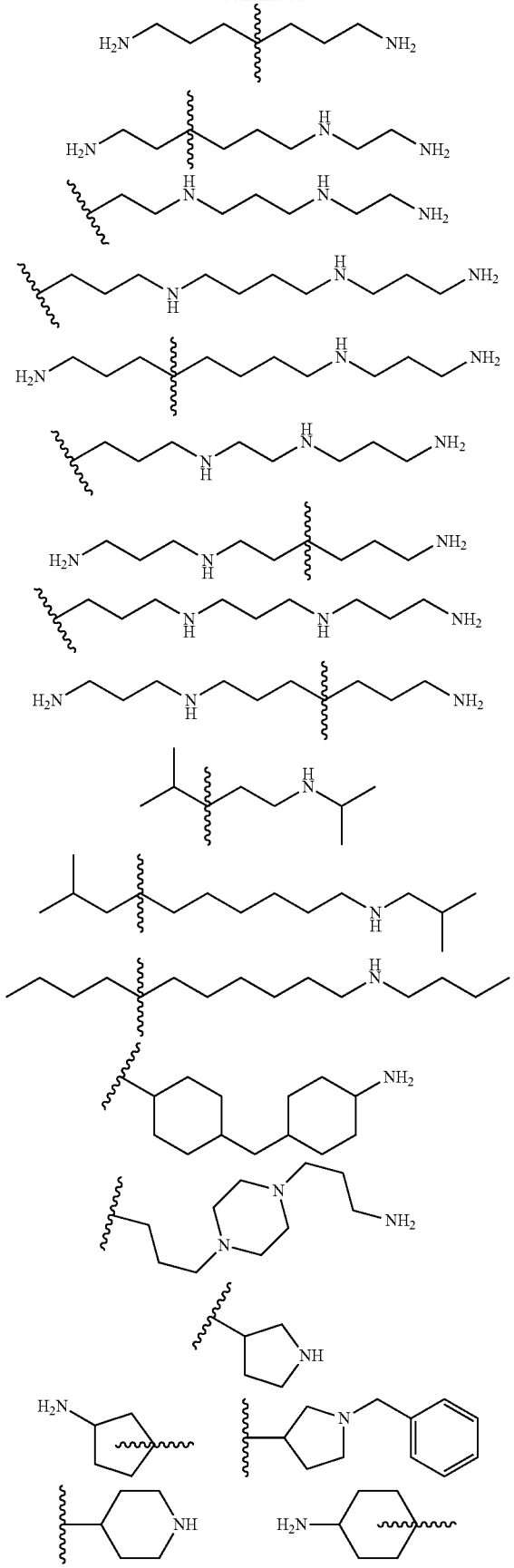
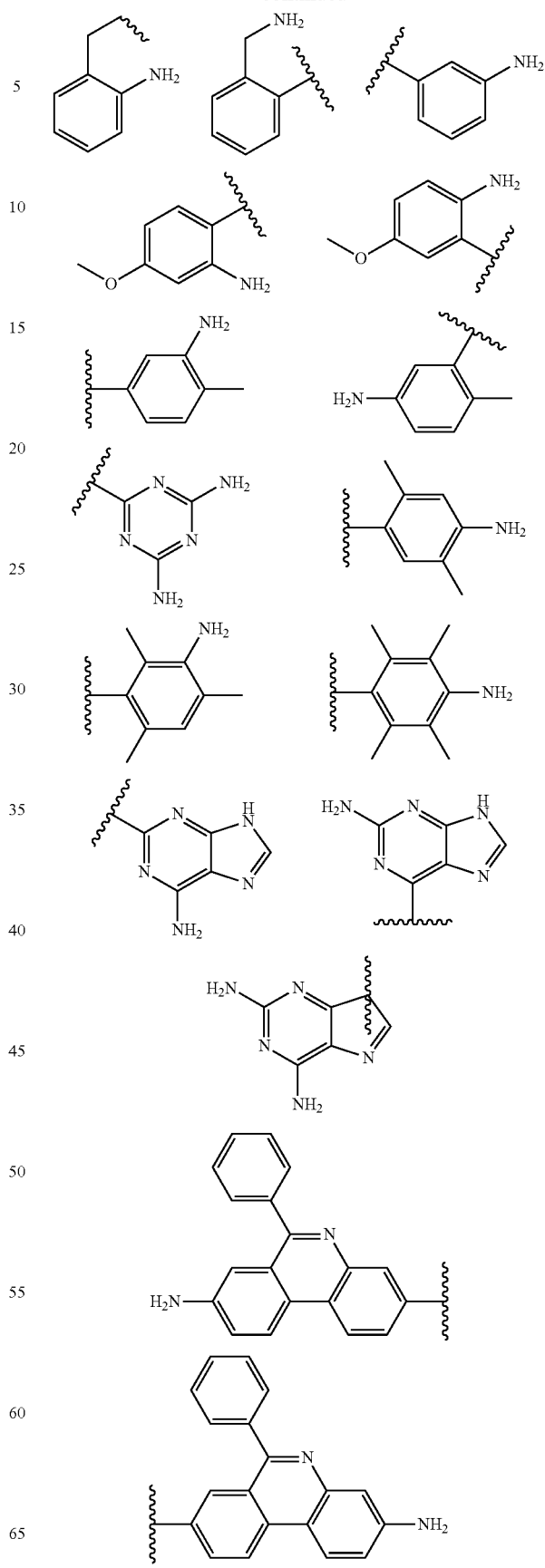

-continued

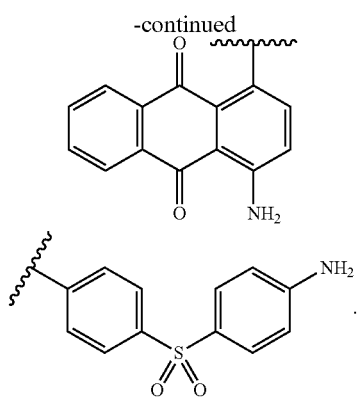

13. The compound of claim 12, wherein n is an integer selected from the group consisting of: an integer from 1 to 1,000; an integer from 1 to 100; an integer from 1 to 30; an integer from 5 to 20; an integer from 10 to 15; and an integer from 1 to 10.

14. A pharmaceutical composition comprising a compound of claim 12.

15. The pharmaceutical composition of claim 14 further comprising a therapeutic agent.

16. The pharmaceutical composition of claim 15, wherein the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug.

17. The pharmaceutical composition of claim 14 further comprising a nanoparticle or microparticle comprising a compound of formula (I).

* * * * *